United States Patent
Martina et al.

(10) Patent No.: US 7,632,854 B2
(45) Date of Patent: Dec. 15, 2009

(54) AMINOINDAZOLE DERIVATIVES ACTIVE AS KINASE INHIBITORS, PROCESS FOR THEIR PREPARATION AND PHARMACEUTICAL COMPOSITIONS COMPRISING THEM

(75) Inventors: Katia Martina, Torre Pellice (IT); Wolfgang Brill, Cesate (IT)

(73) Assignee: Pfizer Italia S.r.l., Rome (IT)

( * ) Notice: Subject to any disclaimer, the term of this patent is extended or adjusted under 35 U.S.C. 154(b) by 668 days.

(21) Appl. No.: 10/990,866

(22) Filed: Nov. 17, 2004

(65) Prior Publication Data

US 2006/0106083 A1    May 18, 2006

(51) Int. Cl.
*A61K 31/415* (2006.01)
*C07D 231/10* (2006.01)

(52) U.S. Cl. .................................. 514/403; 548/373.1

(58) Field of Classification Search .............. 548/373.1; 514/403
See application file for complete search history.

(56) References Cited

U.S. PATENT DOCUMENTS 6,620,831 B2 *   9/2003   Lee et al. .................... 514/372

* cited by examiner

*Primary Examiner*—Golam M. M. Shameem
*Assistant Examiner*—Susannah Chung
(74) *Attorney, Agent, or Firm*—Scully, Scott, Murphy & Presser, P.C.

(57) ABSTRACT

Compounds which are indazole derivatives and pharmaceutically acceptable salts thereof, together with pharmaceutical compositions comprising them, as well as combinatorial libraries of indazole derivatives, as set forth in the specification, are disclosed; these compounds or compositions may be useful in the treatment of diseases caused by and/or associated with an altered protein kinase activity such as cancer, cell proliferative disorders, Alzheimer's disease, viral infections, auto-immune diseases and neurodegenerative disorders.

6 Claims, No Drawings

AMINOINDAZOLE DERIVATIVES ACTIVE AS KINASE INHIBITORS, PROCESS FOR THEIR PREPARATION AND PHARMACEUTICAL COMPOSITIONS COMPRISING THEM

CROSS REFERENCE TO RELATED APPLICATIONS

The present application claims benefit of U.S. Provisional Application No. 60/381,092 filed May 17, 2002.

BACKGROUND OF THE INVENTION

1. Field of the Invention

The present invention relates to aminoindazole derivatives active as kinase inhibitors and, more in particular, it relates to 3-aminoindazoles and derivatives thereof, to a process for their preparation, to pharmaceutical compositions comprising them and to their use as therapeutic agents, particularly in the treatment of diseases linked to disregulated protein kinases.

2. Discussion of Background

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

SUMMARY OF THE INVENTION

It is an object of the invention to provide compounds which are useful in therapy as agents against a host of diseases caused by and/or associated to a disregulated protein kinase activity.

It is another object to provide compounds which are endowed with multiple protein kinase inhibiting activity.

The present inventors have now discovered that the compounds of the invention, hereinafter shortly referred to as aminoindazole derivatives, are endowed with multiple protein kinase inhibiting activity and are thus useful in therapy in the treatment of diseases associated with disregulated protein kinases.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs in the regulation of cellular proliferation, these compounds are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

The compounds of the invention can be useful in the treatment of Alzheimer's disease, as suggested by the fact that cdk5 is involved in the phosphorylation of tau protein (J. Biochem., 117, 741-749, 1995).

The compounds of this invention, as modulators of apoptosis, may also be useful in the treatment of cancer, viral infections, prevention of AIDS development in HIV-infected individuals, autoimmune diseases and neurodegenerative disorders.

The compounds of this invention may be useful in inhibiting tumor angiogenesis and metastasis.

The compounds of the invention are useful as cyclin dependent kinase (cdk) inhibitors and also as inhibitors of other protein kinases such as, for instance, protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, VEGF-R, PI3K, weel kinase, Src, Abl, Akt, ILK, MK-2, IKK-2, Cdc7, Nek, and thus be effective in the treatment of diseases associated with other protein kinases.

DETAILED DESCRIPTION OF THE INVENTION

Several indazoles and aminoindazoles are known in the art as synthetic or chemical intermediates, as polymer stabilizers, as therapeutic agents and even as protein kinase inhibitors.

As an example, some alkylamino-indazoles are disclosed in U.S. Pat. No. 28,939 (reissue of U.S. Pat. No. 3,133,081) by Smithkline Co., as endowed with muscle relaxant and analgesic activity; among them are 3-methylamino-5-trifluoromethyl-indazole and 3-diethylamino-5-trifluoromethyl-indazole.

Cyclic N,N'-urea derivatives bearing 3-aminoindazole groups are disclosed in Bioorg. Med. Chem. Lett. (1998), 8 (7), 715-720 as HIV protease inhibitors.

Diaryl-urea derivatives are disclosed either as p38 kinase inhibitors useful in the treatment of diseases other than cancer, as well as for treating cancerous cell growth mediated by RAF kinase, in WO 99/32111 and WO 99/32106 by Bayer Co; among the compounds specifically exemplified therein is N-[4-[(pyridyl-4-yl)oxy]phenyl]-N'-[6-chloro-(indazol-3-yl)]-urea.

Imidazopyridine derivatives further substituted by aryl moieties, e.g. by indazolyl-aminocarbonyl-phenyl, are disclosed as platelet-activating factor (PAF) antagonists in WO 91/17162 by Pfizer Ltd.

Indazole compounds further substituted in position 3 by groups other than amino or derivatives thereof are disclosed in WO 01/02369 by Agouron Pharmaceuticals Inc., as possessing protein kinase inhibitory activity.

Mercapto-cyanoacryloylamino- or alkylthio-cyanoacryloyl-amino-heterocycles are discloses as being useful in the treatment of disorders associated with increased cell growth in U.S. Pat. No. 5,714,514 by Hoechst.

1-Acylamino-3-(N-arylsulfonyl-N-alkoxyamino)-2-hydroxy-propane derivatives, wherein the aryl moiety also comprises indazole groups, are disclosed as HIV aspartyl protease inhibitors in WO 99/65870 by Vertex Pharmaceuticals Inc.

Quinolylamino- and quinazolylamino-indazoles are disclosed in WO 97/03069 by Glaxo Group Ltd. as possessing protein tyrosine kinase inhibitory activity.

Arylamino-indazoles further substituted in position 5 by heterocyclic rings are disclosed in WO 95/28400 by Glaxo Group Ltd. as possessing selective 5-HT1 agonist activity; the said compounds are thus reported to be useful in the treatment of migraine.

Some other specific indazole derivatives are known as therapeutic agents: in particular, 3-[3-(morpholin-4-yl)propionylamino]-indazole, 3-(N,N,-diethylamino)-propylamino-5-methoxy-indazole, 3-[(3-methyl)morpholin-4-yl]-propylamino-5-methoxy-indazole 3-(N,N,-diethylamino)-propylamino-5-methyl-indazole and 3-[(3-methyl)morpholin-4-yl]-propylamino-5-methyl-indazole are disclosed as possessing analgesic and anti-inflammatory activity [see U.S. Pat. No. 4,751,302 and JP-A-60061569 by Asahi Chemical Industry]; 3-[(2-hydroxyphenyl)carbonylamino]-indazole is disclosed as antimicrobial agent [see Pharmazie (1990), 45 (6), 441-2].

Several other indazoles, mainly disclosed as chemical intermediates or for purposes other than therapeutic, e.g. polymer stabilizers, bleaching agents, dyes and the like, are known in the art.

Among them are: 3-(ethoxycarbonylamino)-indazole [see Chemical Abstracts 92 (1980):215400]; 3-acetylamino-indazole and 3-benzoylamino-indazole [see J. Org. Chem. (1996), 61 (24), 8397-8401]; 3-butyrylamino-indazole, 3-[(4-chlorophenyl)carbonylamino]-indazole, 3-[(4-methyl-phenyl) carbonylamino]indazole and 3-[(3,3-diphenyl)propionylamino]indazole [see Acta Chim. Hung. (1990), 127 (6), 795-802]; 3-[(3,5-dimethyl-isoxazol-4-yl)carbonylamino]-indazole [see J. Heterocyl. Chem. (1974), 11 (4), 623-6]; 3-[(4-nitrophenyl)carbonylamino]-indazole and 3-(phenylacetylamino)-indazole [see J. Chem. Soc., Perkin Trans. 1 (1982), (3), 759-66]; 3-[(2-aminophenyl)carbonylamino]-indazole and 3-[(2-nitrophenyl)carbonylamino]-indazole [Heterocyles (1996), 43 (11), 2385-2396]; 3-[(4-chloro-2-nitrophenyl)carbonyl-amino]-indazole, 3-[(2-amino-4-chlorophenyl)carbonylamino]-indazole, 3-[(2-amino-5-chlorophenyl)carbonylamino]-indazole and 3-[(3-chloro-6-nitrophenyl)carbonylamino]-indazole [see Arch. Pharm. (1999), 332 (9), 317-320]; 3-(acetylamino)-5-amino-indazole [see U.S. Pat. No. 3,316,207 by Farbwerke Hoechst A.G.]; 3-dimethylamino-5-trifluoromethyl-indazole [see DE-A-2458965 by Bayer A.G.]; 3-phenylamino-6-methyl-indazole, 3-phenylamino-, 3-(4-chloro)phenylamino-, 3-(4-methyl)phenylamino-, 3-(3-methyl)phenylamino- and 3-(4-aminosulfonyl)phenylamino-5-methyl-indazole [see Chemical Abstracts 78 (1973): 136158]; 3-[(1-hydroxy-2-methyl)-2-propyl]amino-6,7-dimethoxy-indazole [see U.S. Pat. No. 4,864,032 by Ortho Pharmaceutical Co.].

Sulfonylaminoindazoles and, more particularly, long chain alkyloxyphenylsulfonylamino-indazoles are disclosed as cyan dye forming compounds in JP-A-08022109, by Heisei.

In addition, 3-aminoindazole derivatives, either unsubstituted or substituted at the phenyl moiety by alkoxy, aryloxy, arylaklyoxy groups and the like, are disclosed as protein kinase inhibitors in the co-pending U.S. patent application Ser. No. 09/962,162 (filed in Sep. 26, 2001, in the name of Pharmacia & Upjohn S.p.A.) which is herewith incorporated by reference.

Accordingly, the present invention provides a method for treating diseases caused by and/or associated with an altered protein kinase activity, by administering to a mammal in need thereof an effective amount of a compound represented by formula (I)

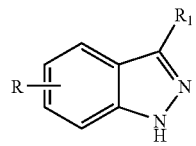

(I)

wherein

R is, in position 5 or 6 of the indazole ring, a halogen atom or an optionally substituted group selected from straight or branched $C_2$-$C_6$ alkenyl, $C_2$-$C_6$ alkynyl, or aryl with from 0 to 3 heteroatoms selected from S, O and N;

$R_1$ is an optionally substituted group selected from —N=CH—$NR_aR_b$, —NHCOR', —NHCONR'R", —NHSO$_2$R' or —NHCOOR';

$R_a$ and $R_b$ are, each independently, hydrogen or a straight or branched $C_1$-$C_6$ alkyl group;

R' and R" are, each independently, hydrogen or an optionally substituted group selected from straight or branched $C_1$-$C_6$ alkyl, $C_2$-$C_6$ alkenyl or alkynyl, $C_3$-$C_6$ cycloalkyl or cycloalkyl $C_1$-$C_6$ alkyl, aryl or aryl $C_1$-$C_6$ alkyl wherein aryl is as above defined; or a 5 or 6 membered heterocyclyl or heterocyclyl $C_1$-$C_6$ alkyl; or, when taken together with the nitrogen atom to which they are attached, R' and R" may form an optionally substituted 4 to 7 membered heterocycle, optionally containing an additional heteroatom selected from S, O or N;

or isomers, tautomers, carriers, prodrugs, and pharmaceutically acceptable salts thereof.

In a preferred embodiment of the method described above, the disease caused by and/or associated with an altered protein kinase activity is selected from the group consisting of cancer, cell proliferative disorders, Alzheimer's disease, viral infections, auto-immune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis glomerulonephritis and post-surgical stenosis and restenosis.

In addition, the method object of the present invention, also provides tumor angiogenesis and metastasis inhibition.

The present invention further provides a compound represented by formula (I)

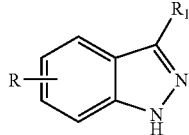

(I)

wherein

R is, in position 5 or 6 of the indazole ring, a halogen atom or an optionally substituted group selected from straight or branched $C_2$-$C_6$ alkenyl, $C_2$-$C_6$ alkynyl, or aryl with from 0 to 3 heteroatoms selected from S, O and N;

$R_1$ is an optionally substituted group selected from —N=CH—$NR_aR_b$, —NHCOR', —NHCONR'R", —$NHSO_2R'$ or —NHCOOR';

$R_a$ and $R_b$ are, each independently, hydrogen or a straight or branched $C_1$-$C_6$ alkyl group;

R' and R" are, each independently, hydrogen or an optionally substituted group selected from straight or branched $C_1$-$C_6$ alkyl, $C_2$-$C_6$ alkenyl or alkynyl, $C_3$-$C_6$ cycloalkyl or cycloalkyl $C_1$-$C_6$ alkyl, aryl or aryl $C_1$-$C_6$ alkyl wherein aryl is as above defined, or a 5 or 6 membered heterocyclyl or heterocyclyl $C_1$-$C_6$ alkyl; or, when taken together with the nitrogen atom to which they are attached, R' and R" may form an optionally substituted 4 to 7 membered heterocycle, optionally containing an additional heteroatom selected from S, O or N;

or isomers, tautomers, carriers, prodrugs, and pharmaceutically acceptable salts thereof.

Unless otherwise specified, when referring to the compounds of formula (I) per se as well as to any pharmaceutical composition thereof or to any therapeutic method of treatment comprising them, the present invention includes all of the hydrates, solvates, complexes and prodrugs of the compounds of this invention. Prodrugs are any covalently bonded compounds, which release the active parent drug according to formula (I) in vivo.

If a chiral center or another form of an isomeric center is present in a compound of the present invention, all forms of such isomer or isomers, including enantiomers and diastereomers, are intended to be covered herein. Compounds containing a chiral center may be used as a racemic mixture or as an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

In the present description, as formerly indicated, R is in position 5 or 6 of the indazole group, according to the following numbering system:

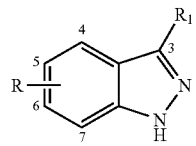

(I)

In the present description, unless otherwise specified, with the term halogen atom we intend a fluorine, chlorine, bromine or iodine atom.

With the term straight or branched $C_1$-$C_6$ alkyl group we intend any group such as, for instance, methyl, ethyl, n-propyl, isopropyl, n-butyl, isobutyl, sec-butyl, tert-butyl, n-pentyl, n-hexyl, and the like.

With the term $C_2$-$C_6$ alkenyl or alkynyl group we intend any of the aforementioned straight or branched alkyl groups, with from 2 to 6 carbon atoms, further bearing a double or triple bond.

Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term $C_3$-$C_6$ cycloalkyl we intend, unless otherwise indicated, any 3 to 6 membered carbocyclic ring such as, for instance, cyclopropyl, cyclobutyl, cyclopentyl and cyclohexyl.

With the term aryl we intend a mono-, bi- or poly- either carbocyclic as well as heterocyclic hydrocarbon with from 1 to 4 ring moieties, either fused or linked to each other by single bonds, wherein at least one of the carbocyclic or heterocyclic rings is aromatic.

From the above it is clear to the skilled person that, whereas any aryl group with 0 heteroatoms is an aromatic carbocyclic ring, any aryl group with from 1 to 3 heteroatoms is an aromatic heterocyclic ring, also known as heteroaryl group.

Unless otherwise specified, the said heteroaryl groups are 5 or 6 membered rings with from 1 to 3 heteroatoms selected among nitrogen, oxygen or sulphur.

Non limiting examples of aryl groups of the invention are, for instance, phenyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, and the like.

With the term 5 or 6 membered heterocyclyl, hence encompassing aromatic heterocyclic groups also referred to as aryl groups, we further intend a saturated or partially unsaturated 5 or 6 membered heterocycle with from 1 to 3 heteroatoms such as nitrogen, oxygen and sulfur. Examples of these 5 or 6 membered heterocyclyl groups, optionally benzocondensed or further substituted, are 1,3-dioxolane, pyran, pyrrolidine, pyrroline, imidazolidine, pyrazolidine, pyrazoline, piperidine, piperazine, morpholine, tetrahydrofuran, and the like.

When referring to the compounds of formula (I) wherein $R_1$ is a group —NHCONR'R" and R' and R" are taken together with the nitrogen atom to which they are attached, they may also form an optionally substituted 4 to 7 membered heterocycle, optionally containing a heteroatom selected from S, O or N, in addition to the N atom directly bonded to R' and R".

For a general reference to the above heterocyclic groups see, for instance, cyclic amino derivatives per the following table VI.

From all of the above, it is clear to the skilled man that any group which name has been identified as a composite name such as, for instance, cycloalkylalkyl, arylalkyl, heterocyclylalkyl and the like, has to be intended as conventionally construed from the parts to which it derives. So far, the term heterocyclyl-alkyl stands for a straight or branched alkyl group being further substituted by a heterocyclyl group, as above defined.

According to the above meanings provided to R, R$_1$, R' and, R", any of the above groups may be further optionally substituted in any of their free positions by one or more groups, for instance 1 to 6 groups, selected from: halogen, nitro, oxo groups (=O), carboxy, cyano, alkyl, perfluorinated alkyl, alkenyl, alkynyl, cycloalkyl, aryl, heterocyclyl, amino groups and derivatives thereof such as, for instance, alkylamino, dialkylamino, arylamino, diarylamino, ureido, alkylureido or arylureido; carbonylamino groups and derivatives thereof such as, for instance, formylamino, alkylcarbonylamino, alkenylcarbonylamino, arylcarbonylamino, alkoxycarbonylamino; hydroxy groups and derivatives thereof such as, for instance, alkoxy, aryloxy, alkylcarbonyloxy, arylcarbonyloxy, cycloalkenyloxy or alkylideneaminooxy; carbonyl groups and derivatives thereof such as, for instance, alkylcarbonyl, arylcarbonyl, alkoxycarbonyl, aryloxycarbonyl, cycloalkyloxycarbonyl, aminocarbonyl, alkylaminocarbonyl, dialkylaminocarbonyl; sulfurated derivatives such as, for instance, alkylthio, arylthio, alkylsulfonyl, arylsulfonyl, alkylsulfinyl, arylsulfinyl, arylsulfonyloxy, aminosulfonyl, alkylaminosulfonyl or dialkylaminosulfonyl.

In their turn, whenever appropriate, each of the above substituents may be further substituted by one or more of the aforementioned groups.

The term "pharmaceutically acceptable salts" embraces salts commonly used to form alkali metal salts and to form addition salts of free acids or free bases. The nature of the salt is not critical, provided that it is pharmaceutically acceptable. Suitable pharmaceutically acceptable acid addition salts of compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic and sulfonic classes of organic acids, examples of which are formic, acetic, trifluoroacetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, phydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, hydroxybutyric, salicyclic, galactaric and galacturonic acid.

Suitable pharmaceutically acceptable base addition salts of the compounds of the present invention include metallic salts made from aluminum, calcium, lithium, magnesium, potassium, sodium and zinc or organic salts made from N,N'-dibenzylethytenediamine, chloroprocaine, choline, diethanolamine, ethylenediamine, meglumine (N-methyl-glucamine) and procaine. All of these salts may be prepared by conventional means from the corresponding compound of the present invention by reacting, for example, the appropriate acid or base.

A first embodiment of the invention is represented by the derivatives of formula (I) wherein R is an optionally substituted aryl group and R$_1$ is a group —NHCOR', wherein R' is as above defined.

Another embodiment of the invention is represented by the derivatives of formula (I) wherein R is an optionally substituted aryl group and R$_1$ is a group —NHCONR'R", wherein one of R' or R" is a hydrogen atom and the remaining one of R' or R" is as above defined.

Another embodiment of the invention is represented by the derivatives of formula (I) wherein R is an optionally substituted aryl group and R$_1$ is a group —NHCONR'R", wherein R' and R" are both, as above defined, other than hydrogen.

Another embodiment of the invention is represented by the derivatives of formula (I) wherein R is in optionally substituted aryl group and R$_1$ is a group —NHSO$_2$R', wherein R' is as above defined.

Another embodiment of the invention is represented by the derivatives of formula (I) wherein R is in optionally substituted aryl group and R$_1$ is a group —NHCOOR', wherein R' is as above defined.

Another embodiment of the invention is represented by the derivatives of formula (I) wherein R is in optionally substituted aryl group and R$_1$ is a group —N=CH—NR$_a$R$_b$, wherein R$_a$ and R$_b$ are both methyl groups.

Preferably, in all of the above classes, the optionally substituted aryl group, in position 5 or 6 of the indazole ring, is selected from any 5 or 6 membered aryl group with from 0 to 3 heteroatoms selected among N, O or S, optionally further benzocondensed.

Typical examples of preferred aryl groups of the invention are, for instance, phenyl, biphenyl, α- or β-naphthyl, pyridyl, pyrazinyl, pyrimidinyl, pyridazinyl, indolyl, imidazolyl, thiazolyl, isothiazolyl, pyrrolyl, furyl, benzofuranyl, oxazolyl, isoxazolyl, pyrazolyl, thienyl, benzothienyl, benzoimidazolyl, quinolinyl, isoquinolinyl, and the like.

Specific examples of compounds of formula (I), optionally in the form of pharmaceutically acceptable salts, are conveniently listed in the experimental section and claims.

As set forth above, it is a further object of the present invention a process for preparing the compounds of formula (I).

Therefore, the compounds of formula (I) and the pharmaceutically acceptable salts thereof may be obtained by a process comprising:

a) reacting a compound of formula (II) with hydrazine hydrate

(II)

wherein Hal is a halogen atom, so as to obtain a compound of formula (III)

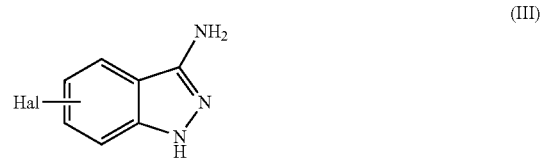

(III)

wherein the halogen atom is in position 5 or 6 of the indazole ring;

b) reacting the compound of formula (III) with a suitable dimethylacetal derivative of formula (IV)

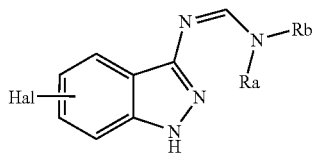

wherein $R_a$ and $R_b$ are as above defined, so as to obtain a compound of formula (I)

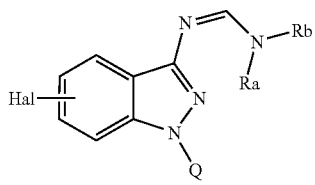

wherein $R_a$ and $R_b$ are as above defined; and, optionally, converting the thus obtained compound of formula (I) into another compound of formula (I), by:

c) reacting the compound of formula (I), as per step (b) of the process, with a suitable indazole nitrogen protecting agent or, alternatively, supporting it onto a suitable polymeric resin so as to obtain a compound of formula (V)

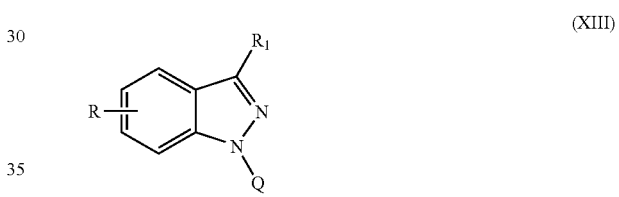

wherein Q is the above nitrogen protecting group or represents the supporting resin;

d) reacting the compound of formula (V) with hydrazine monohydrate so as to get a compound of formula (VI)

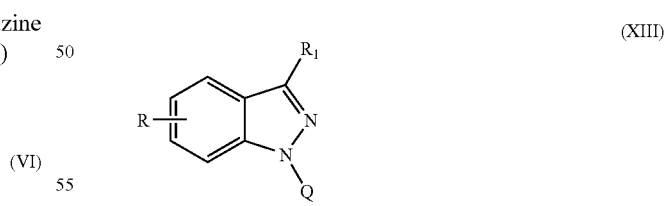

e) reacting the compound of formula (VI) with a suitable boronic acid derivative of formula (VII)

R—B(OH)$_2$ (VII)

wherein R is as above defined, so as to obtain a compound of formula (VII)

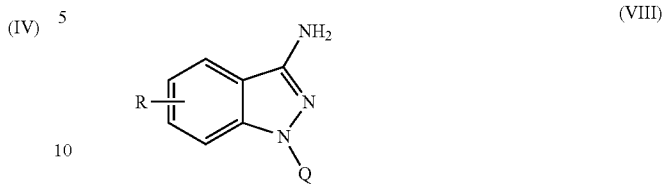

and reacting the compound of formula (VII) according to any one of the alternative steps (f.1) or (f.2), as follows:

f.1) with any one of the compounds of formula (IX), (X), (XI) or (XII)

R'CO-Z  (IX)

R'SO$_2$-Z  (X)

R'—NCO  (XI)

R'OCO-Z  (XII)

wherein R' is as above defined and Z is a halogen atom or a suitable leaving group, so as to obtain the compounds of formula (XIII)

wherein R and Q are as above defined and $R_1$ is a group —NHCOR', —NHSO$_2$R', —NHCONHR' or —NHCOOR'; or f.2) with a suitable amine of formula (XIV)

HNR'R"  (XIV)

wherein R' and R" are as above defined, in the presence of a suitable aryl chloroformate derivative, so as to obtain a compound of formula (XIII)

(XIII)

wherein R and Q are as above defined and $R_1$ is a group of formula —NHCONR'R";

g) deprotecting the compound of formula (XIII) being obtained according to any one of steps (f.1) or (f.2) or, alternatively, cleaving the polymeric resin so as to get the desired compound of formula (I) and, whenever desired, converting it into another compound of formula (I) and/or into a pharmaceutically acceptable salt thereof.

From all of the above, it is clear to the person skilled in the art that if a compound of formula (I), prepared according to the above process, is obtained as an admixture of isomers, their separation into the single isomers of formula (I), carried out according to conventional techniques, is still within the scope of the present invention.

Likewise, the conversion into the free compound (I) of a corresponding salt thereof, according to well-known procedures in the art, is still within the scope of the invention.

According to step (a) of the process, a compound of formula (II), preferably 4-bromo-2-fluorobenzonitrile or 5-bromo-2-fluorobenzonitrile, is reacted with hydrazine hydrate so as to get the formation of the indazole ring.

The reaction may be carried out according to conventional methods, for instance in a lower alcohol, preferably n-butanol, at a temperature ranging from room temperature to refluxing temperature, and for a time of about 4 to about 12 hours.

According to step (b) of the process, the compound of formula (I) having $R_1$ as a —N=CH—$NR_aR_b$ group can be easily prepared by reacting the indazole derivative of formula (III) with a dimethylacetal derivative of formula (IV), for instance dimethylformamide dimethylacetal wherein $R_a$ and $R_b$ are both methyl groups.

The reaction is carried out according to conventional methods, by operating in a suitable solvent, for instance dimethylformamide, at room temperature and for a time varying from about 8 to about 36 hours.

According to step (c) of the process, the indazole derivative of formula (I) wherein $R_1$ is a —N=CH—$NR_aR_b$ group is either protected at the indazole nitrogen atom or, alternatively, is supported onto a suitable polymeric resin.

The reaction of protection may be carried out according to conventional methods well known in the art, for instance by using suitable nitrogen protecting groups such as, for instance, tert-butoxy-carbonyl (BOC) group.

At this same position, in the alternative, this indazole derivative may be also conveniently anchored to an inert polymeric support such as, for instance, the 2-chloro-trityl chloride resin, the trityl chloride resin, the p-nitrophenyl carbonate Wang resin or the bromo-(4-methoxyphenyl)methyl polystyrene, which are all conventionally known in this field.

Clearly, this same option is particularly advantageous for preparing the compounds of formula (I) under solid-phase-synthesis (SPS) conditions, which are typically adopted when preparing libraries of compounds according to combinatorial chemistry techniques, for instance as reported below.

The reaction with the resin is carried out in the presence of a slight excess of a suitable base, for instance an amine, e.g. diisopropylethylamine (DIPEA), triethylamine (TEA), 1,8-diazabiciclo[5.4.0]undec-7-ene (DBU) or 2-tert-butylimino-2-diethylamino-1,3-dimethylperhydro-1,3,2-diaza-phosphorine, in a suitable solvent, for instance dichloromethane, chloroform, tetrahydrofuran, dimethylformamide, dimethylacetamide, 1-methyl-2-pyrrolidinone and the like.

Preferably, the reaction is carried out in 1-methyl-2-pyrrolidinone at a temperature of about 20° C.

The reaction may be performed by adding to a suspension of the resin, the base and the indazole derivative, and by stirring at a temperature of about 20° C. for a suitable time, for instance up to 24 hours.

According to step (d) of the process, the protected—or otherwise polymer supported-derivative of formula (V) is reacted with hydrazine monohydrate in a suitable solvent, for instance water, pyridine and admixtures thereof. Preferably, the reaction is carried out in the presence of pyridine/water admixtures, at a temperature ranging from about 40° C. to about 100° C. and for a suitable time, for instance from 24 hours to few days, e.g. 48 hours.

According to step (e) of the process, the 3-amino-indazole derivatives of formula (VI) are then reacted with a suitable boronic acid of formula (VII), according to well-known Suzuki coupling conditions.

Typically, the reaction is carried out in the presence of catalytic amounts of tris(dibenzylideneacetone)dipalladium, palladium acetate, 1,1'-bis(diphenylphosphino)ferrocene-dichloropalladium, tetrakis(triphenylphosphine)palladium or bis(triphenylphosphine)palladium chloride. The reaction occurs by adding a suitable base, for instance cesium carbonate, potassium phosphate tribasic and the like, and a palladium ligand, for instance triphenylphosphine.

In this respect, the compound of formula (VI) is suspended in a suitable degased solvent such as toluene, N-methyl-2-pyrrolidone, dimethoxyethane, dioxane, and the like; a mixture of water and dimethoxyethane being preferred.

Subsequently, the compound of formula (VII), the catalyst, the base and the ligand are then added therein. The suspension is then brought to a suitable temperature varying from about 50° C. to about 100° C. whereas stirring is maintained for a time of about 8 hours to few days e.g. 48 hrs. The reaction is carried out under inert atmosphere.

The indazole derivative of formula (VII) thus prepared can be then conveniently reacted according to any one of the alternative steps (f.1) or (f.2).

As per step (f.1) of the process, the compound of formula (VII) is reacted with a suitable reagent of formula (IX), (X), (XI) or (XII), according to well-known methods.

Typically, the compound of formula (VIII) may be reacted with: a compound of formula (IX) so as to get the corresponding amido derivative wherein $R_1$ is a group —NHCOR' and R' is as above defined; a compound of formula (X) to get the corresponding sulfonamido derivative wherein $R_1$ is a group —$NHSO_2R'$ and R' is as above defined; a compound of formula (XI) to get the corresponding ureido derivative wherein $R_1$ is a —NHCONHR' group and R' is as above defined; with a compound of formula (XII) to get the corresponding carbamate derivative wherein $R_1$ is a —NHCOOR' group and R' is as above defined.

Any one of the above reactions is carried out according to conventional methods normally used in the preparation of functionalized amino derivatives, by starting from the corresponding amine.

Preferably, within the compounds of formula (IX), (X) or (XII), Z represents a halogen atom and, even more preferably, a chlorine atom.

In this respect, the compound of formula (VIII) is dissolved in a suitable solvent such as dichloromethane, chloroform, dimethylformamide, tetrahydrofuran, dioxane, pyridine and admixtures thereof, and a suitable base is added such as, for instance, triethylamine, diisopropylethylamine, sodium carbonate, 1-methyl-imidazole, and the like. The compound of general formula (IX), (X) or (XII) is then added and the mixture stirred for a time of about 2 hours to about 24 hours, at a temperature ranging from about 20° C. to about 50° C. In all of these reactions, a suitable catalyst such as dimethylamino pyridine may be optionally used.

Preferably, when the reaction is performed in the presence of a reagent of general formula (IX) or (X), a further treatment with ammonium hydroxide is required so as to remove any side product being formed.

When using an isocyanate of general formula (XI), the reaction conditions are those as above reported, with the exception that the base may not be required.

Alternatively, as per step (f.2) of the process, the compound of formula (VII) may be reacted with a compound of formula R'R"NH (XIV), in the presence of a suitable aryl chloroformate, for instance 4-nitrophenyl- or 4-chlorophenyl-chloroformate so as to get the corresponding ureido —NHCONR'R" derivative of formula (XIII).

As an example, to the compound of formula (VIII) properly dissolved in a suitable solvent such as dichloromethane, chloroform, dimethylformamide, tetrahydrofuran, dioxane and admixtures thereof, a suitable base such as triethylamine, diisopropylethylamine, sodium carbonate, 1-methyl imidazole and the like, together with a suitable aryl chloroformate, for instance 4-nitrophenyl- or 4-chlorophenyl-chloroformate, are added therein. The mixture is stirred for about 1 hour to about 12 hours at room temperature. The compound of formula (XIV) is then added to this suspension, and the mixture is stirred from about 12 hours to about few days, at a temperature ranging from about 20° C. to about 40° C.

Finally, according to step (g) of the process, the compound of formula (XIII) is deprotected at the indazole nitrogen atom by working according to conventional methods, in acidic conditions. The compound of formula (XIII) is thus suspended in a suitable solvent such as methyl alcohol, ethyl alcohol or the like, and a concentrated solution of hydrochloric acid is added. The mixture is stirred for a suitable time of about 5 hours to about 15 hours at a temperature ranging from about 20° C. to about 40° C.; preferably at about 20° C.

Alternatively, this same intermediate compound of formula (XIII) is cleaved from the resin to which it is supported.

Resin cleavage may be carried out, for instance, in the presence of trifluoroacetic acid so as to yield the desired compound of formula (I). The resin is suspended in a solution of 5-95% of trifluoroacetic acid in dichloromethane or chloroform and the mixture is stirred at about 20° C. for a time varying from about 5 minutes to about 3 hours.

When preparing the compounds of formula (I) according to any variant of the process, which are all to be intended as within the scope of the present invention, optional functional groups within both the starting materials, the reagents or the intermediates thereof, and which could give rise to unwanted side reactions, need to be properly protected according to conventional techniques.

Likewise, the conversion of these latter into the free deprotected compounds may be carried out according to known procedures.

Pharmaceutically acceptable salts of the compounds of formula (I) or, alternatively, their free compounds from the salts thereof, my be all obtained according to conventional methods. The starting materials of formula (II) of the above process are known and commercially available or, alternatively, may be prepared according to well-known methods.

Likewise, if not commercially available per se, the compounds of formula (IV), (VII), (IX), (X), (XI), (XII) and (XIV), are all known or easily prepared according to well-known methods. As formerly indicated, the compounds of formula (I) of the invention were conveniently prepared according to combinatorial chemistry techniques widely known in the art, by accomplishing the aforementioned reactions between the intermediates in a serial manner and by working under SPS conditions.

All of the preferred compounds of the invention, whenever appropriate in the form of pharmaceutically acceptable salts, are herewith conveniently indicated and defined as products by process, that is as products of formula (I) which are obtainable, for instance through a given process.

Therefore, herewith provided are novel compounds of the invention and the pharmaceutically acceptable salts thereof which are obtainable, for instance through a combinatorial chemistry technique as per the above process, by first reacting the compound of formula (VIa)

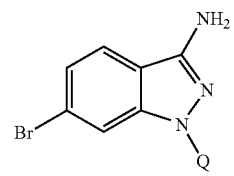

(VIa)

wherein Q is the supporting resin (Trityl-chloride resin) with each one of the derivatives of formula (VII), as set forth in table I, so as to obtain a plurality of compounds of formula (VIIIa)

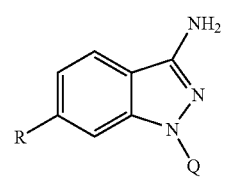

(VIIIa)

by then reacting each of the derivatives of formula (VIIIa) with each one of the derivatives of formula (IX), as set forth in table II, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIa)

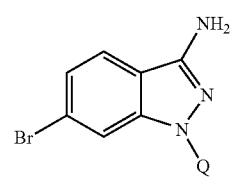

(VIa)

wherein Q is the supporting resin (Trityl-chloride resin) with each one of the derivatives of formula (VII), as set forth in table I, so as to obtain a plurality of compounds of formula (VIIIa)

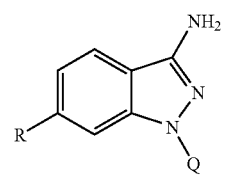

(VIIIa)

by then reacting each of the derivatives of formula (VIIIa) with each one of the derivatives of formula (X), as set forth in table III, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIa)

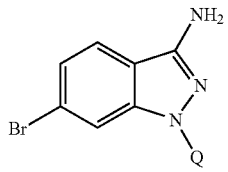
(VIa)

wherein Q is the supporting resin (Trityl-chloride resin) with each one of the derivatives of formula (VII), as set forth in table I, so as to obtain a plurality of compounds of formula (VIIIa)

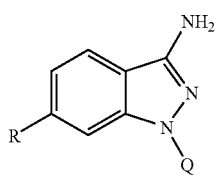
(VIIIa)

by then reacting each of the derivatives of formula (VIIIa) with each one of the derivatives of formula (XI), as set forth in table IV, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIa)

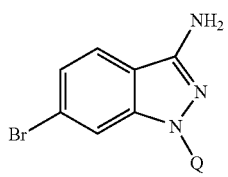
(VIa)

wherein Q is the supporting resin (Trityl-chloride resin) with each one of the derivatives of formula (VII), as set forth in table I, so as to obtain a plurality of compounds of formula (VIIIa)

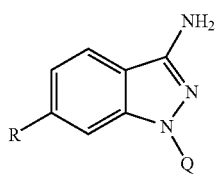
(VIIIa)

by then reacting each of the derivatives of formula (VIIIa) with each one of the derivatives of formula (XII), as set forth in table V, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIa)

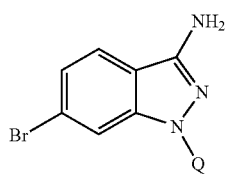
(VIa)

wherein Q is the supporting resin (Trityl-chloride resin) with each one of the derivatives of formula (VII), as set forth in table I, so as to obtain a plurality of compounds of formula (VIIIa)

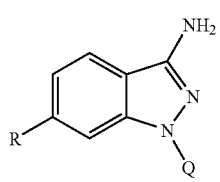
(VIIIa)

by then reacting each of the derivatives of formula (VIIIa) with each one of the derivatives of formula (XIV), as set forth in table VI, in the presence of 4-nitrophenyl-chloroformate, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIb)

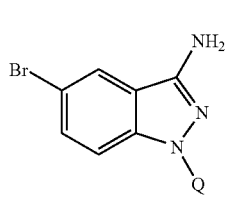
(VIb)

wherein Q is the supporting resin (Trityl-chloride resin) with each one of the derivatives of formula (VII), as set forth in table I, so as to obtain a plurality of compounds of formula (VIIIb)

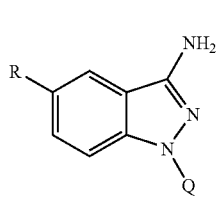
(VIIIb)

by then reacting each of the derivatives of formula (VIIIb) with each one of the derivatives of formula (IX), as set forth in table II, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIb)

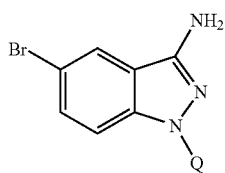
(VIb)

wherein Q is the supporting resin (Trityl-chloride resin) with each one of the derivatives of formula (VII), as set forth in table I, so as to obtain a plurality of compounds of formula (VIIIb)

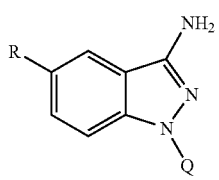
(VIIIb)

by then reacting each of the derivatives of formula (VIIIb) with each one of the derivatives of formula (X), as set forth in table III, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIb)

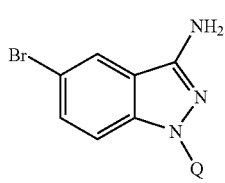
(VIb)

wherein Q is the supporting resin (Trityl-chloride resin) with each one of the derivatives of formula (VII), as set forth in table I, so as to obtain a plurality of compounds of formula (VIIIb)

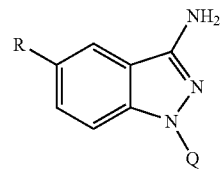
(VIIIb)

by then reacting each of the derivatives of formula (VIIIb) with each one of the derivatives of formula (XI), as set forth in table IV, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIb)

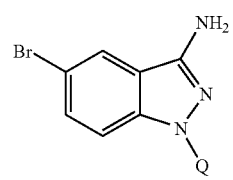
(VIb)

wherein Q is the supporting resin (Trityl-chloride resin) with each one of the derivatives of formula (VII), as set forth in table I, so as to obtain a plurality of compounds of formula (VIIIb)

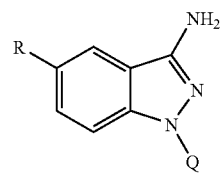
(VIIIb)

by then reacting each of the derivatives of formula (VIIIb) with each one of the derivatives of formula (XII), as set forth in table V, and by subsequently operating as per step (g) of the process.

Also provided are novel compounds of the invention and the pharmaceutically acceptable salts thereof which are obtainable, for instance through a combinatorial chemistry technique as per the above process, by first reacting the compound of formula (VIb)

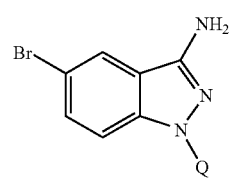
(VIb)

wherein Q is the supporting resin (Trityl-chloride resin) with each one of the derivatives of formula (VII), as set forth in table I, so as to obtain a plurality of compounds of formula (VIIIb)

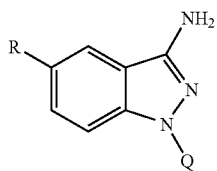

by then reacting each of the derivatives of formula (VIIIb) with each one of the derivatives of formula (XIV), as set forth in table VI, in the presence of 4-nitrophenyl-chloroformate, and by subsequently operating as per step (g) of the process.

TABLE I

Compounds of formula R-B(OH)$_2$ (VII)

| | |
|---|---|
| 1. | 2,4-difluorophenylboronic acid |
| 2. | 2,4-dimethoxyphenylboronic acid |
| 3. | 5-isopropyl-2-methoxybenzeneboronic acid |
| 4. | 2,5-difluorophenylboronic acid |
| 5. | 2,5-dimethoxyphenylboronic acid |
| 6. | 2-methylphenylboronic acid |
| 7. | 2-ethoxyphenylboronic acid |
| 8. | (2-methylthio)phenylboronic acid |
| 9. | 2,6-dimethylbenzeneboronic acid |
| 10. | (3,4-dimethylphenyl)boronic acid |
| 11. | 3,4-dichlorophenylboronic acid |
| 12. | 3-chloro-4-fluorobenzeneboronic acid |
| 13. | 3-chlorophenylboronic acid |
| 14. | 3,5-dimethylphenylboronic acid |
| 15. | 3-methylphenylboronic acid |
| 16. | 3-acetylphenylboronic acid |
| 17. | 3-methoxyphenylboronic acid |
| 18. | 2,5-dimethylbenzeneboronic acid |
| 19. | 5-fluoro-2-methoxyphenylboronic acid |
| 20. | 4-tolylboronic acid |
| 21. | 4-acetylphenylboronic acid |
| 22. | (4-isopropylphenyl)boronic acid |
| 23. | 4-fluorophenylboronic acid |
| 24. | 4-(dimethylamino)phenylboronic acid |
| 25. | 4-methoxyphenylboronic acid |
| 26. | 4-(trifluoromethoxy)benzeneboronic acid |
| 27. | 4-(ethylthiophenyl)boronic acid |
| 28. | 3-acetylphenylboronic acid |
| 29. | 3-fluorophenylboronic acid |
| 30. | 3-acetamidobenzeneboronic acid |
| 31. | 3-(trifluoromethoxy)benzeneboronic acid |
| 32. | 3-ethoxyphenylboronic acid |
| 33. | phenylboronic acid |
| 34. | 2-fluorophenylboronic acid |
| 35. | 2-methoxyphenylboronic acid |
| 36. | 2-thiopheneboronic acid |
| 37. | thiophene-3-boronic acid |
| 38. | 4-cyanophenylboronic acid |
| 40. | (2-cyanophenyl)boronic acid |
| 41. | 4-(hydroxymethyl)phenylboronic acid |

TABLE II

Compounds of formula R'CO-Z (IX)

| | |
|---|---|
| 1. | acetyl chloride |
| 2. | isobutyryl chloride |
| 3. | diphenylacetyl chloride |
| 4. | 2-phenylbutyryl chloride |
| 5. | dl-2-methylbutyryl chloride |
| 6. | 2-ethylhexanoyl chloride |
| 7. | 2-n-propyl-n-valeroyl chloride |
| 8. | 2-phenoxypropionyl chloride |

TABLE II-continued

Compounds of formula R'CO-Z (IX)

| | |
|---|---|
| 9. | 2,3,6-trifluorobenzoyl chloride |
| 10. | 2,4-dimethoxybenzoyl chloride |
| 11. | 2-methoxybenzoyl chloride |
| 12. | 2-chloro-6-fluorobenzoyl chloride |
| 13. | 3,4,5-trimethoxybenzoyl chloride |
| 14. | 2,3,4,5-tetrafluorobenzoyl chloride |
| 15. | 3,5-dichlorobenzoyl chloride |
| 16. | 3-chlorobenzoyl chloride |
| 17. | 3-fluorobenzoyl chloride |
| 18. | cyclopropanecarbonyl chloride |
| 19. | 2,4-difluorobenzoyl chloride |
| 20. | cyclobutanecarbonyl chloride |
| 21. | cyclopentanecarbonyl chloride |
| 22. | 2-furoyl chloride |
| 23. | propionyl chloride |
| 24. | 4-methoxyphenylacetyl chloride |
| 25. | 3-methoxyphenylacetyl chloride |
| 26. | cyclopentylacetyl chloride |
| 27. | phenylacetyl chloride |
| 28. | butyryl chloride |
| 29. | 3-cyclopentylpropionyl chloride |
| 30. | methoxyacetyl chloride |
| 31. | 4-chlorophenoxyacetyl chloride |
| 32. | benzyloxyacetyl chloride |
| 33. | O-acetylmandelic acid chloride |
| 34. | N-(p-toluenesulfonyl)-l-phenylalanyl chloride |

TABLE III

Compounds of formula R'SO$_2$-Z (X)

| | |
|---|---|
| 1. | 3,4-dichlorobenzenesulfonyl chloride |
| 2. | 2,4-difluorobenzenesulphonyl chloride |
| 3. | 3-chloro-2-methylbenzenesulfonyl chloride |
| 4. | 4-N-propylbenzenesulfonyl chloride |
| 5. | 2-chloro-4-fluorobenzenesulphonyl chloride |
| 6. | 3-methoxybenzenesulphonyl chloride |
| 7. | methanesulfonyl chloride |
| 8. | 2-thiophenesulfonyl chloride |
| 9. | 5-chlorothiophene-2-sulfonyl chloride |
| 10. | 5-fluoro-2-methylbenzenesulphonyl chloride |

TABLE IV

Compounds of formula R'-NCO (XI)

| | |
|---|---|
| 1. | isopropyl isocyanate |
| 2. | sec-butyl isocyanate |
| 3. | o-tolyl isocyanate |
| 4. | 2-methoxyphenyl isocyanate |
| 5. | 3-methoxyphenyl isocyanate |
| 6. | 4-methoxyphenyl isocyanate |
| 7. | phenyl isocyanate |
| 8. | ethyl isocyanate |
| 9. | ethyl isocyanatoacetate |
| 10. | n-propyl isocyanate |
| 11. | n-butyl isocyanate |

TABLE V

Compounds of formula R'OCO-Z (XII)

| | |
|---|---|
| 1. | phenyl chloroformate |
| 2. | 4-chlorophenyl chloroformate |
| 3. | benzyl chloroformate |
| 4. | isobutyl chloroformate |
| 5. | 4-nitrophenyl chloroformate |
| 6. | 4-fluorophenyl chloroformate |

TABLE VI

Compounds of formula HNR'R" (XIV)

| | |
|---|---|
| 1. | piperidine |
| 2. | butylamine |
| 3. | 4-(2-aminoethyl)morpholine |
| 4. | 1-(3-aminopropyl)imidazole |
| 5. | piperazine |
| 6. | tetrahydrofurfurylamine |
| 7. | phenethylamine |
| 8. | 3-phenylpropylamine |
| 9. | n-propylamine |
| 10. | isobutylamine |
| 11. | cyclopropanemethylamine |
| 12. | 2-(2-aminoethyl)-1-methylpyrolidine |
| 13. | 4-methylpiperidine |
| 14. | 1-methylpiperazine |
| 15. | 1-(3-aminopropyl)-2-pyrrolidinone |
| 16. | 1,3-diaminopropane |
| 17. | ethylenediamine |
| 18. | 4-hydroxypiperidine |
| 19. | 3-amino-1-propanol |
| 20. | 2-(2-aminoethyl)pyridine |
| 21. | 1-(2-aminoethyl)piperidine |
| 22. | pyrrolidine |
| 23. | n-acetylethylenediamine |
| 24. | 1-acetylpiperazine |
| 25. | 3-methoxypropylamine |
| 26. | 3-methylpiperidine |
| 27. | 2-methylbutylamine |
| 28. | 1-(2-pyridyl)piperazine |
| 29. | 4-benzylpiperidine |
| 30. | n,n-diethylnipecotamide |
| 31. | 3,5-dimethylpiperidine |
| 32. | 2-(aminomethyl)-1-ethylpyrrolidine |
| 33. | 1-(2-furoyl)piperazine |
| 34. | thiophene-2-ethylamine |
| 35. | 1-(2-aminoethyl)-2-imidazolone |
| 36. | thiomorpholine |
| 37. | propargyl chloroformate |
| 38. | 4-piperidinopiperidine |
| 39. | 1-piperazinecarboxaldehyde |
| 40. | 1-benzylpiperazine |
| 41. | 3-piperidinemethanol |
| 42. | 3-ethoxypropylamine |
| 43. | isoamylamine |
| 44. | 1-(2-fluorophenyl)piperazine |
| 45. | 1-(2-hydroxyethyl)-piperazine |
| 46. | n,n-diethylethylenediamine |
| 47. | 1-(2-methoxyphenyl)piperazine |
| 48. | 4-(1-pyrrolidinyl)piperidine |
| 49. | 3-(dimethylamino)propylamine |
| 50. | 2-phenyl-propylamine |
| 51. | 3-hydroxypiperidine |
| 52. | 1-(3 aminopropyl) pyrrolidene |
| 53. | 1-hydroxyethylethoxypiperazine |
| 54. | 2,6-dimethylpiperazine |
| 55. | 3-isopropoxypropylamine |
| 56. | 1-(2,3-dimethylphenyl)-piperazine |
| 57. | 1-(3-methoxyphenyl)-piperazine |
| 58. | n,n-diisopropylethyleneamine |
| 59. | (r)-(−)-2-methylpiperazine |
| 60. | 1-(2,5-dimethylphenyl)piperazine |
| 61. | 2-methyl-1-(3-methylphenyl)piperazine |
| 62. | 1-cyclohexylpiperazine |
| 63. | 2-methylpiperazine |
| 64. | 1-(4-fluorophenyl)piperazine |
| 65. | 1-ethylpropylamine |
| 66. | dl-alpha-methylbenzylamine |
| 67. | 3,4-dimethoxybenzylamine [veratrylamine] |
| 68. | 2-methylbenzylamine |
| 69. | 2-methoxyethylamine |
| 70. | allylamine |
| 71. | azetidine hydrochloride |
| 72. | ammonia |

Accordingly, it is a further object of the present invention a library of two or more compounds of formula (I)

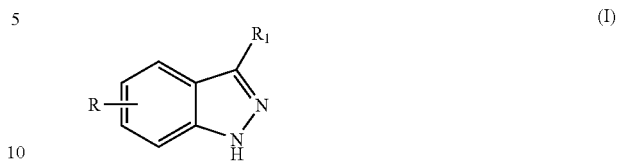

wherein

R is, in position 5 or 6 of the indazole ring, a halogen atom or an optionally substituted group selected from straight or branched $C_2$-$C_6$ alkenyl, $C_2$-$C_6$ alkynyl, or aryl with from 0 to 3 heteroatoms selected from S, O and N;

$R_1$ is an optionally substituted group selected from —N═CH—$NR_aR_b$, —NHCOR', —NHCONR'R", —NHSO$_2$R' or —NHCOOR';

$R_a$ and $R_b$ are, each independently, hydrogen or a straight or branched $C_1$-$C_6$ alkyl group;

R' and R" are, each independently, hydrogen or an optionally substituted group selected from straight or branched $C_1$-$C_6$ alkyl, $C_2$-$C_6$ alkenyl or alkynyl, $C_3$-$C_6$ cycloalkyl or cycloalkyl $C_1$-$C_6$ alkyl, aryl or aryl $C_1$-$C_6$ alkyl wherein aryl is as above defined, or a 5 or 6 membered heterocyclyl or heterocyclyl $C_1$-$C_6$ alkyl; or, when taken together with the nitrogen atom to which they are attached, R' and R" may form an optionally substituted 4 to 7 membered heterocycle, optionally containing an additional heteroatom selected from S, O or N. From all of the above, it is clear to the skilled man that once a library of indazole derivatives is thus prepared, for instance consisting of a few thousands of compounds of formula (I), the said library can be very advantageously used for screening towards given target kinases, as formerly reported.

See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The compounds of formula (I) are active as protein kinase inhibitors and are therefore useful, for instance, to restrict the unregulated proliferation of tumor cells.

In therapy, they may be used in the treatment of various tumors such as, for instance, carcinomas, e.g. mammary carcinoma, lung carcinoma, bladder carcinoma, colon carcinoma, ovary and endometrial tumors, sarcomas, e.g. soft tissue and bone sarcomas, and the hematological malignancies such as, e.g., leukemias.

In addition, the compounds of formula (I) are also useful in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative cdk/cyclin inhibitors and the potency of selected compounds is determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of cdk2/Cyclin A Activity

Kinase Reaction: 4; µM in house biotinylated histone H1 (Sigma # H-5505) substrate, 10 µM ATP (0.1 microCi $P^{33}\gamma$-ATP), 4.2 ng Cyclin A/CDK2 complex, inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+ 500 µM ATP, containing 1 mg SPA beads. Then a volume of 110 µl is transferred to Optiplate.

After 20 min. incubation for substrate capture, 100 µl 5M CsCl were added to allow statification of beads to the top of the plate and let stand 4 hours before radioactivity counting in the Top-Count instrument IC50 Determination: inhibitors are tested at different concentrations ranging from 0.0015 to 10 µM. Experimental data are analyzed by the computer program GraphPad Prizm using the four parameter logistic equation:

$$y = \text{bottom} + (\text{top}-\text{bottom})/(1+10^{((\log IC50 - x)*\text{slope})})$$

where x is the logarithm of the inhibitor concentration, y is the response; y starts at bottom and goes to top with a sigmoid shape.

Ki Calculation:

Experimental Method: Reaction was carried out in buffer (10 mM Tris, pH 7.5, 10 mM $MgCl_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates are read on a top counter. Control (time zero) for each ATP and histone concentrations was measured.

Experimental Design: Reaction velocities are measured at different four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allow the selection of a single endpoint time (10 min) in the linear range of the reaction for the Ki determination experiment.

Kinetic Parameter Estimates: Kinetic parameters were estimated by simultaneous nonlinear least-square regression using [Eq. 1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + \alpha \cdot Kb \cdot A + A \cdot B + \alpha \cdot \frac{Ka}{Ki} \cdot I \cdot \left(Kb + \frac{B}{\beta}\right)} \quad [\text{Eq. 1}]$$

where A=[ATP], B=[Substrate], I=[inhibitor], Vm=maximum velocity, Ka, Kb, Ki the dissociation constants of ATP, substrate and inhibitor respectively. α and β the cooperativity factor between substrate and ATP binding and substrate and inhibitor binding respectively.

In addition the selected compounds have been characterized on a panel of ser/threo kinases strictly related to cell cycle (cdk2/cyclin E, cdk1/cyclin B1, cdk5/p25, cdk4/cyclin D1), and also for specificity on MAPK, PKA, EGFR, IGF1-R, and Aurora-2.

Inhibition Assay of cdk2/Cyclin E Activity

Kinase Reaction: 10 µM in house biotinylated histone H1 (Sigma # H-5505) substrate, 30 µM ATP (0.3 microCi $P^{33}\gamma$-ATP), 4 ng GST-Cyclin E/CDK2 complex, inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After 60 min at r.t. incubation, reaction was stopped by 100 µl, PBS+32 mM EDTA+0.1% Triton X-100+ 500 µM ATP, containing 1 mg SPA beads. Then a volume of 110 µl, is transferred to Optiplate.

After 20 min. incubation for substrate capture, 100 µl 5M CsCl were added to allow statification of beads to the top of the plate and let stand 4 hours before radioactivity counting in the Top-Count instrument IC50 Determination: see above Inhibition Assay of cdk1/Cyclin B1 Activity Kinase Reaction: 4 µM in house biotinylated histone H1 (Sigma # H-5505) substrate, 20 µM ATP (0.2 microCi $P^{33}\gamma$-ATP), 3 ng Cyclin B/CDK1 complex, inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After 20 min at r.t. incubation, reaction was stopped by 100 µl PBS+32 mM EDTA+0.1% Triton X-100+ 500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 Determination: see above

Inhibition Assay of cdk5/p25 activity

The inhibition assay of cdk5/p25 activity was performed according to the following protocol.

Kinase Reaction: 10 µM biotinylated histone H1 (Sigma # H-5505) substrate, 30 µM ATP (0.3 microCi $P^{33}\gamma$-ATP), 15 ng CDK5/p25 complex, inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate.

After 20 min. incubation for substrate capture, 100 µl 5M CsCl were added to allow statification of beads to the top of the plate and let stand 4 hours before radioactivity counting in the Top-Count instrument.

IC50 Determination: see above

Inhibition Assay of cdk4/Cyclin D1 Activity

Kinase Reaction: 0.4 uM µM mouse GST-Rb (769-921) (# sc-4112 from Santa Cruz) substrate, 10 µM ATP (0.5 µCi $P^{33}\gamma$-ATP), 100 ng of baculovirus expressed GST-cdk4/GST-Cyclin D1, suitable concentrations of inhibitor in a final volume of 50 µl buffer (TRIS HCl 10 mM pH 7.5, $MgCl_2$ 10 mM, 7.5 mM DTT+0.2 mg/ml BSA) were added to each well of a 96 U bottom well plate. After 40 min at 37° C. incubation, reaction was stopped by 20 µl EDTA 120 mM.

Capture: 60 µl were transferred from each well to Multi-Screen plate, to allow substrate binding to phosphocellulose filter. Plates were then washed 3 times with 150 µl/well PBS $Ca^{++}/Mg^{++}$ free and filtered by MultiScreen filtration system.

Detection: Filters were allowed to dry at 37° C., then 100 µl/well scintillant were added and $^{33}P$ labeled Rb fragment was detected by radioactivity counting in the Top-Count instrument.

IC50 Determination: see above.

Inhibition Assay of MAPK Activity

Kinase Reaction: 10 µM in house biotinylated MBP (Sigma # M-1891) substrate, 15 µM ATP (0.15 microCi $P^{33}\gamma$-ATP), 30 ng GST-MAPK (Upstate Biotechnology # 14-173), inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 Determination: see above.

Inhibition Assay of PKA Activity

Kinase Reaction:

10 µM in house biotinylated histone H1 (Sigma # H-5505) substrate, 10 µM ATP (0.2 microM $P^{33}\gamma$-ATP), 0.45 U PKA (Sigma # 2645), inhibitor in a final volume of 30 µl buffer (TRIS HCl 10 mM pH 7.5, $MgCl_2$ 10 mM, DTT 7.5 mM+0.2 mg/ml BSA) were added to each well of a 96 U bottom. After 90 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 Determination: see above.

Inhibition Assay of EGFR Activity

Kinase Reaction: 10 µM in house biotinylated MBP (Sigma # M-1891) substrate, 2 µM ATP (0.04 microCi $P^{33}\gamma$-ATP), 36 ng insect cell expressed GST-EGFR, inhibitor in a final volume of 30 µl buffer (Hepes 50 mM pH 7.5, $MgCl_2$ 3 mM, $MnCl_2$ 3 mM, DTT 1 mM, $NaVO_3$ 3 µM+0.2 mg/ml BSA) were added to each well of a 96 U bottom. After 20 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 Determination: see above.

Inhibition Assay of IGF1-R Activity

The inhibition assay of IGF1-R activity is performed according to the following protocol.

Kinase Reaction: 10 µM biotinylated MBP (Sigma cat. # M-1891) substrate, 0-20 µM inhibitor, 6 µM ATP, 1 microCi $^{33}$P-ATP, and 22.5 ng GST-IGF1-R (pre-incubated for 30 min at room temperature with cold 60 µM cold ATP) in a final volume of 30 µl buffer (50 mM HEPES pH 7.9, 3 mM $MnCl_2$, 1 mM DTT, 3 µM $NaVO_3$) were added to each well of a 96 U bottom well plate. After incubation for 35 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

Inhibition Assay of Aurora-2 Activity

Kinase Reaction: 8 µM biotinylated peptide (4 repeats of LRRWSLG), 10 µM ATP (0.5 uCi $P^{33}$g-ATP), 15 ng Aurora2, inhibitor in a final volume of 30 µl buffer (HEPES 50 mM pH 7.0, $MgCl_2$ 10 mM, 1 mM DTT, 0.2 mg/ml BSA, 3 µM orthovanadate) were added to each well of a 96 U bottom well plate. After 30 minutes at room temperature incubation, reaction was stopped and biotinylated peptide captured by adding 100 µl of bead suspension.

Stratification: 100 µl of $CsCl_2$ 5 M were added to each well and let stand 4 hour before radioactivity was counted in the Top-Count instrument.

IC50 Determination: see above

Inhibition Assay of Cdc7/dbf4 Activity

The inhibition assay of Cdc7/dbf4 activity is performed according to the following protocol.

The Biotin-MCM2 substrate is trans-phosphorylated by the Cdc7/Dbf4 complex in the presence of ATP traced with $\gamma^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:

10 µl substrate (biotinylated MCM2, 6 µM final concentration)

10 µl enzyme (Cdc7/Dbf4, 12.5 nM final concentration)

10 µl test compound (12 increasing concentrations in the nM to µM range to generate a dose-response curve)

10 µl of a mixture of cold ATP (10 nM final concentration) and radioactive ATP (1/2500 molar ratio with cold ATP) was then used to start the reaction which was allowed to take place at 37° C.

Substrate, enzyme and ATP were diluted in 50 mM HEPES pH 7.9 containing 15 mM $MgCl_2$, 2 mM DTT, 3 µM $NaVO_3$, 2 mM glycerophosphate and 0.2 mg/ml BSA. The solvent for test compounds also contained 10% DMSO.

After incubation for 20 minutes, the reaction was stopped by adding to each well 100 µl of PBS pH 7.4 containing 50 mM EDTA, 1 mM cold ATP, 0.1% Triton X100 and 10 mg/ml streptavidin coated SPA beads.

After 15 minutes of incubation at room temperature to allow the biotinylated MCM2-streptavidin SPA beads interaction to occur, beads were trapped in a 96 wells filter plate (Unifilter® GF/B™) using a Packard Cell Harvester (Filtermate), washed with distilled water and then counted using a Top Count (Packard).

Counts were blank-subtracted and then the experimental data (each point in triplicate) were analyzed for IC50 determination using a non-linear regression analysis (Sigma Plot).

The compounds of formula (I) of the present invention, suitable for administration to a mammal, e.g. to humans, can be administered by the usual routes and the dosage level depends upon the age, weight, conditions of the patient and the administration route.

For example, a suitable dosage adopted for oral administration of a compound of formula (I) may range from about 10 to about 500 mg pro dose, from 1 to 5 times daily.

The compounds of the invention can be administered in a variety of dosage forms, e.g. orally, in the form of tablets, capsules, sugar or film coated tablets, liquid solutions or suspensions; rectally in the form of suppositories; parenterally, e.g. intramuscularly, or by intravenous and/or intrathecal and/or intraspinal injection or infusion.

In addition, the compounds of the invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), metallomatrixprotease inhibitors, telomerase inhibitors, tyrosine kinase inhibitors, anti-growth factor receptor agents, anti-HER agents, anti-EGFR agents, anti-angiogenesis agents, farnesyl transferase inhibitors, rasraf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described above and the other pharmaceutically active agent within the approved dosage range.

Compounds of formula (I) may be used sequentially with known anticancer agents when a combination formulation is inappropriate.

The present invention also includes pharmaceutical compositions comprising a compound of formula (I) or a pharmaceutically acceptable salt thereof in association with a pharmaceutically acceptable excipient (which can be a carrier or a diluent).

The pharmaceutical compositions containing the compounds of the invention are usually prepared following conventional methods and are administered in a pharmaceutically suitable form.

For example, the solid oral forms may contain, together with the active compound, diluents, e.g. lactose, dextrose, saccharose, sucrose, cellulose, corn starch or potato starch; lubricants, e.g. silica, talc, stearic, magnesium or calcium stearate, and/or polyethylene glycols; binding agents, e.g. starches, arabic gum, gelatin, methylcellulose, carboxymethylcellulose or polyvinyl pyrrolidone; disaggregating agents, e.g. a starch, alginic, alginates or sodium starch glycolate; effervescing mixtures; dyestuffs; sweeteners; wetting agents such as lecithin, polysorbates, laurylsulfates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The liquid dispersions for oral administration may be e.g. syrups, emulsions and suspensions. The syrups may contain as carrier, for example, saccharose or saccharose with glycerin and/or mannitol and/or sorbitol.

The suspensions and the emulsions may contain as carrier, for example, a natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain as carrier, for example, sterile water or preferably they may be in the form of sterile, aqueous, isotonic saline solutions or they may contain as a carrier propylene glycol.

The suppositories may contain together with the active compound a pharmaceutically acceptable carrier, e.g. cocoa butter, polyethylene glycol, a polyoxyethylene sorbitan fatty ester surfactant or lecithin.

The following examples are herewith intended to better illustrate the present invention without posing any limitation to it.

General Methods

Flash Chromatography was performed on silica gel (Merck grade 9395, 60A).

The samples were analyzed by using the following two methods:

Method I: the analysis was performed on Waters X Terra 18 (4.6×50 mm, 3.5 µm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 minutes. UV detection at 220 nm and 254 nm. Flow rate 1 ml/min. Injection volume 10 µl. Full scan, mass range from 100 to 800 amu. Capillary voltage was 2.5 KV; source temp. was 120° C.; cone was 10 V. Retention times (HPLC r.t.) are given in minutes at 220 nm or at 254 nm. Mass are given as m/z ratio.

Method II: The analysis was performed on LCMS instrument comprising: Hewlett Packard 1312A binary pump; Gilson 215 autosampler fitted with a 1 ml syringe; Polymer Labs PL1000 Evaporative Light Scattering Detector; Micromass ZMD mass spectrometer operating in Electrospray positive ionisation mode.

The LC eluent is split and approximately 200 µl/min enters the mass spectrometer, 800 µl/min to the ELS. The instruments are currently controlled using Micromass MassLynx 3.5 software under Windows NT4.0

HPLC Conditions:

Mobile Phase: Aqueous–Water+0.1% Trifluoroacetic acid

| | Organic – Acetonitrile + 0.1% Trifluoroacetic acid | | |
|---|---|---|---|
| Gradient: | Time (mins) | % Aqueous | % Organic |
| | 0.0 | 100 | 0 |
| | 1.8 | 5 | 95 |
| | 2.1 | 5 | 95 |
| | 2.3 | 100 | 0 |
| | 2.4 | 100 | 0 |
| Run time: | 2.4 mins | | |
| Flow rate: | 1 ml/min | | |
| Injection vol: | 3 µl | | |
| Column temperature: | ambient (20° C.) | | |
| Column: | 50 × 2.0 mm Hypersil C18 BDS; 5 µm | | |
| ELS Detector | Nebuliser Temperature 80° C. | | |
| Evaporation temperature | 90° C. | | |
| Gas Flow | 1.5 l/hr | | |
| MS Detector: | m/z 150-800 at 0.5 secs/scan, 0.1 second interscan delay; Cone voltage 25 V, Source Temp. 140° C. | | |
| Drying Gas | 350 l/hr | | |

When necessary, compounds have been purified by preparative HPLC; two different instruments were used:

Instrument 1: Waters Symmetry C18 (19×50 mm, 5 µm) Column, HPLC 600 instrument equipped with a 996 Waters PDA detector and a Micromass mod. ZMD single quadrupole mass spectrometer, electron spray ionization, positive mode. Mobile phase A was water 0.1% formic acid, and Mobile phase B was acetonitrile. Gradient from 10 to 90% B in 8 min, hold 90% B 2 min. Flow rate 20 ml/min.

Instrument 2: Waters Symmetry C18 (4.6×50 mm, 3.5 µm) Column; HPLC 600 instrument equipped with a 996 Waters PDA detector and a Micromass mod. ZMD single quadrupole mass spectrometer, electron spray ionization, positive mode. Mobile phase A was 95% aq. $NH_4OAc$ (5 mM) pH 5/5% MeCN, and Mobile phase B was 5% $H_2O$/95% MeCN. Gradient from 10 to 90% B in 8 min, hold 90% B 2 min. Flow rate 1 ml/min.

1H-NMR spectrometry was performed on a Mercury VX 400 operating at 400.45 MHz equipped with a 5 mm double resonance probe [1H (15N-31P) ID-PFG Varian].

As formerly indicated, several compounds of formula (I) of the invention have been synthesized in parallel, according to combinatorial chemistry techniques.

In this respect, some compounds thus prepared have been conveniently and unambiguously identified, as per the coding system of tables X and XI, together with HPLC retention time and experimentally found [M+H]+.

Each code, which unambiguously identifies a single specific compound of formula (I) only, consists of three units A-M-B or, alternatively, A-M-C.

Code A represents any R substituent, as per formula (I), being attached to the rest of the indazole moiety in position 6; each A group is represented through the proper chemical formula in the following table VII, together with its point of attachment to the rest of the molecule M.

Code M refers to the central core of the indazole moiety which bears, in position 3, an amido group (—NHCO—) and is further substituted in position 6 by the aforementioned A group. Codes B and C represent the groups which are linked to the above amido portion so as to give rise to —NHCO-B or —NHCO-C groups $R_1$, as per formula (I).

Each B and C group is represented through the proper chemical formula in the following tables VII and IX, respectively; the point of attachment of B and C groups to the rest of the molecule M is also clearly indicated in tables VIII and IX.

Therefore, the coding system presently used for some of the compounds of formula (I) can be shortly summarised as follows:

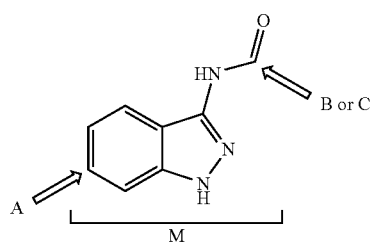

Just as an example, which is not intended to limit the scope of the present invention, the compound A15-M-B19 of table X (see example 6, entry 1) represents the 3-amido indazole moiety M being substituted in position 6 by the group A15 and at the amido portion by the group B19; likewise, the compound A39-M-C3 of table XI (see example 8, entry 26) represents a 3-amido-indazole moiety M being substituted in position 6 by the group A39 and at the amido portion by the group C3.

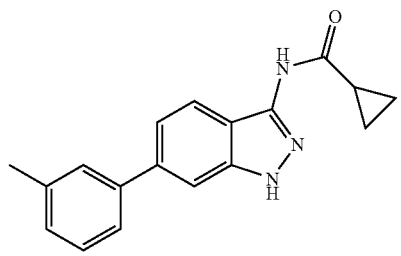

A15-M-B19

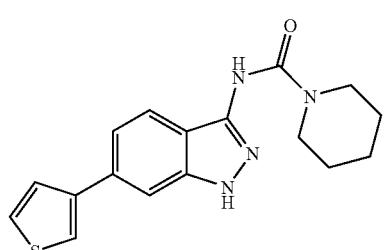

A39-M-C3

TABLE VII

A groups

| Fragment | Code |
|---|---|
| | A1 |
| | A2 |
| | A3 |
| | A4 |

TABLE VII-continued

A groups

| Fragment | Code |
|---|---|
| M-(2,5-dimethoxyphenyl) | A5 |
| M-(2-methylphenyl) | A6 |
| M-(2-ethoxyphenyl) | A7 |
| M-(2-methylthiophenyl) | A8 |
| M-(2,6-dimethylphenyl) | A9 |
| M-(3,4-dimethylphenyl) | A10 |
| M-(3,4-dichlorophenyl) | A11 |
| M-(3-chloro-4-fluorophenyl) | A12 |
| M-(3,4-difluorophenyl) | A13 |
| M-(3,5-dimethylphenyl) | A14 |
| M-(3-methylphenyl) | A15 |
| M-(3-cyanophenyl) | A16 |
| M-(3-acetylphenyl) | A17 |
| M-(3-chlorophenyl) | A18 |
| M-(3-methoxyphenyl) | A19 |
| M-(2,5-dimethylphenyl) | A20 |
| M-(4-fluoro-2-methoxyphenyl) | A21 |
| M-(4-methylphenyl) | A22 |
| M-(4-cyanophenyl) | A23 |
| M-(4-acetylphenyl) | A24 |
| M-(4-isopropylphenyl) | A25 |

TABLE VII-continued

A groups

| Fragment | Code |
|---|---|
| M–C₆H₄–F (para) | A26 |
| M–C₆H₄–N(CH₃)₂ (para) | A27 |
| M–C₆H₄–OCH₃ (para) | A28 |
| M–C₆H₄–OCF₃ (para) | A29 |
| M–C₆H₄–SCH₂CH₃ (para) | A30 |
| M–C₆H₄–F (meta) | A31 |
| M–C₆H₄–NHC(O)CH₃ (meta) | A32 |
| M–C₆H₄–OCF₃ (meta) | A33 |
| M–C₆H₄–OCH₂CH₃ (meta) | A34 |
| M–C₆H₅ | A35 |
| M–C₆H₄–F (ortho) | A36 |
| M–C₆H₄–OCH₃ (ortho) | A37 |
| M–(2-thienyl) | A38 |
| M–(3-thienyl) | A39 |

TABLE VIII

B groups

| Fragment | Code |
|---|---|
| PhCH₂CH(M)–NHSO₂–C₆H₄–CH₃ | B1 |
| M–CH₃ | B2 |
| M–CH(CH₃)₂ | B3 |
| M–CH(C₆H₅)₂ | B4 |
| M–CH(CH₂CH₃)(C₆H₅) | B5 |
| M–CH(C₆H₅)–OC(O)CH₃ | B6 |

TABLE VIII-continued

B groups

| Fragment | Code |
|---|---|
| isobutyl (M-CH(CH3)CH2CH3) | B7 |
| M-CH(CH3)-O-phenyl | B8 |
| 2,3,6-trifluorophenyl (M attached) | B9 |
| 2,4-dimethoxyphenyl (M attached) | B10 |
| 2-methoxyphenyl (M attached) | B11 |
| 2-chloro-6-fluorophenyl (M attached) | B12 |
| 2,6-difluorophenyl (M attached) | B13 |
| 3,4,5-trimethoxyphenyl (M attached) | B14 |
| 2,3,4,5-tetrafluorophenyl (M attached) | B15 |
| 3,5-dichlorophenyl (M attached) | B16 |
| 3-chlorophenyl (M attached) | B17 |
| 3-fluorophenyl (M attached) | B18 |
| cyclopropyl (M attached) | B19 |
| 3,4-difluorophenyl (M attached) | B20 |
| 2,4-dichlorophenyl (M attached) | B21 |
| 2,4-difluorophenyl (M attached) | B22 |
| cyclobutyl (M attached) | B23 |
| 3-cyanophenyl (M attached) | B24 |
| cyclopentyl (M attached) | B25 |
| phenyl (M attached) | B26 |
| cyclohexyl (M attached) | B27 |

TABLE VIII-continued

B groups

| Fragment | Code |
|---|---|
| 2-fluorophenyl (M attached) | B28 |
| 2-furyl (M attached) | B29 |
| M–ethyl | B30 |
| M–CH2–(4-methoxyphenyl) | B31 |
| M–CH2–(3-methoxyphenyl) | B32 |
| M–CH2–cyclopentyl | B33 |
| M–CH2–phenyl (benzyl) | B34 |
| M–CH2–(2-thienyl) | B35 |
| M–propyl | B36 |
| M–CH2CH2–cyclopentyl | B37 |
| M–CH2CH2–phenyl | B38 |
| M–butyl | B39 |
| M–(CH2)3–O–phenyl | B40 |
| M–CH2–O–CH3 | B41 |
| M–CH2–O–C(=O)–CH3 | B42 |

TABLE VIII-continued

B groups

| Fragment | Code |
|---|---|
| M–CH2–O–(4-chlorophenyl) | B43 |
| M–CH2–O–CH2–phenyl | B44 |

TABLE IX

C Groups

| Fragment | Code |
|---|---|
| M–N(piperidin-1-yl), 4-benzyl | C1 |
| M–N(pyrrolidin-1-yl) | C2 |
| M–N(piperidin-1-yl) | C3 |
| M–N(piperazin-1-yl), 4-(pyridin-2-yl) | C4 |
| M–N(piperazin-1-yl) | C5 |
| M–N(thiomorpholin-4-yl) | C6 |
| M–NH–CH2–cyclopropyl | C7 |
| M–NH–CH2–(tetrahydrofuran-2-yl) | C8 |
| M–NH–CH2CH2–phenyl | C9 |

TABLE IX-continued
C Groups
| Fragment | Code |
|---|---|
| 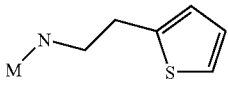 | C10 |
| 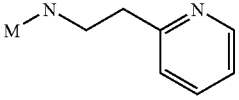 | C11 |
| 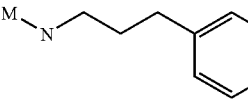 | C12 |
| 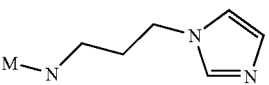 | C13 |
| 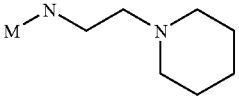 | C14 |
| 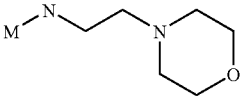 | C15 |
| 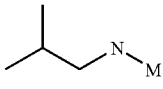 | C16 |
| 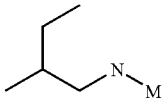 | C17 |
| 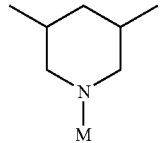 | C18 |
| 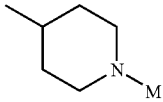 | C19 |
| 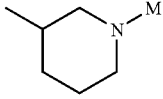 | C20 |
| 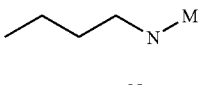 | C21 |
|  | C22 |
TABLE IX-continued
C Groups
| Fragment | Code |
|---|---|
| 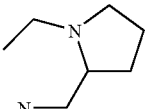 | C23 |
| 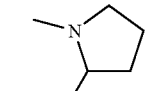 | C24 |
| 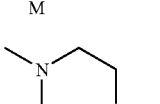 | C25 |
| 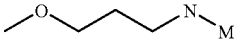 | C26 |
| 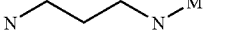 | C27 |
|  | C28 |
| 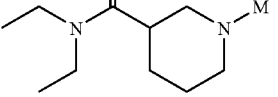 | C29 |
| 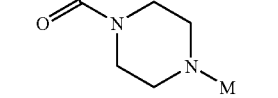 | C30 |
| 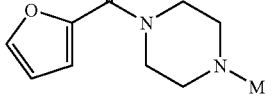 | C31 |
| 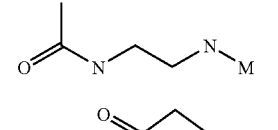 | C32 |
|  | C33 |

TABLE IX-continued

C Groups

| Fragment | Code |
|---|---|
| (imidazolidinone with N-CH2CH2-N-M) | C34 |
| (4-oxy-piperidine N-M) | C35 |
| O-CH2CH2CH2-N-M | C36 |

EXAMPLE 1

6-bromo-1H-indazol-3-amine 4-bromo-2-fluorobenzonitrile (67.8 g), hydrazine hydrate (32.8 ml) in n-butanol (410 ml) were heated to 112° C. for five hours. The reaction mixture was allowed to cool down to r.t. The precipitated crystalline solid was filtered off and washed three times with ethylacetate (100 ml each). The product was dried in vacuo at 40° C. mp. 222-225° C.

$[M+H]^+=213$; $^1$H-NMR (300 MHz DMSO-$d_6$): 11.43 (s, 1H); 7.61 (d, 1H); 7.4 (d, 1H); 7.0 (d of d, 1H); 5.4 (s, 2H)

EXAMPLE 2

N'-(6-bromo-1H-indazol-3-yl)-N,N-dimethylimidoformamide 6-bromo-1H-indazol-3-amine (70.5 g) was suspended in dimethylformamide dimethylacetal (600 ml). After one hour the solid was completely into solution. After 1.5 hours a white crystalline solid appeared and after 5 hours HPLC indicated complete conversion. The reaction mixture was evaporated in vacuo to give an oil, which was precipitated into MeCN/H$_2$O 1/1 (v/v). The crystalline, yellowish solid was stirred for another 15 min., then filtered and washed subsequently with H$_2$O (100 ml). The solid was then washed with DCM (2×250 ml). The DCM-filtrates contained some product which could be retrieved upon crystallization at −10° C.

tlc: Rf: 0.24 (DCM, EtOAc, MeCN) 60/35/5 (v/v/v); $[M+H]^+=269$; $^1$H-NMR (300 MHz DMSO-$d_6$): 12.3 (s, 1H); 8.19 (s, 1H); 7.5-7.6 (s, d, 2H); 7.08 (d of d, 1H); 3.02, 2.98 (two s, 6H)

$^1$H-NMR of the TFA-salt of N'-(6-bromo-1H-indazol-3-yl)-N,N-dimethylimidoformamide (300 MHz DMSO-$d_6$): 8.79 (s, 1H); 7.89 (d of d, J=8.8, J'=0.5 1H); 7.79 (m, 1H); 7.35 (d of d, J=8.8, J'=1.7 1H); 3.40 (s, 3H); 3.29 (s, 3H).

EXAMPLE 3

N'-(6-bromo-1-trityl resin-1H-indazol-3-yl)-N,N-dimethylimidoformamide

To commercial polystyrene resin bearing TritylChloride (loading 0.75-1.35 mmol/g, 125 g) and 6-bromo-1H-indazol-3-amine (62.5 g), 62.5 ml of dry 1,8-diazabiciclo[5.4.0]undec-7-ene (DBU) and dry dimethylformamide (900 ml) were added. The slurry was stirred for 48 hours at room temperature under exclusion of moisture with a mechanical overhead stirrer. An aliquot of the slurry containing 10-50 mg of resin was removed from the reaction mixture, transferred into a sinter glass frit with a valve on its bottom and washed the following way:

3× a) 1 ml DMF; b) 1 ml H$_2$O
2× a) 1 ml MeOH; b) 1 ml DMF
1×1 ml MeOH
2× a) 1 ml toluene; 1 ml diethylether
3×1 ml diethylether.

The resin was dried in vacuo, then weighed.

From the known amount of resin the bound indazole was determined upon cleavage using TFA whereby collecting the cleavage solutions. The cleavage was performed the following way:

1×0.5 ml 20% TFA/DCM 5 min.
4×0.2 ml 20% TFA/DCM 2 min.

The combined cleavage solutions combined and then dried in vacuo. The dried TFA-salt of the N'-(6-bromo-1H-indazol-3-yl)-N,N-dimethylimidoformamide was weighed, and analyzed. The weight of the recovered material revealed the loading of the resin. When the loading exceeded 0.7 mmol/g the immobilization reaction was quenched upon addition of MeOH (100 ml).

The slurry was transferred into a commercial "resin wash station" (Rink) an washed as follows: 3×700 ml DMF: the effluent from the washing vessel was collected to recover unused indazole.

3× a) 700 ml DMF; b) 700 ml H$_2$O
2× a) 700 ml MeOH; b) 700 ml DMF
1×700 ml MeOH
2× a) 700 ml toluene; 700 ml diisopropylether
3×700 ml diisopropylether.

The resin was dried in vacuo until constancy of weight. The weight of the resin revealed the loading of the indazole. The loading determined by weight increase corresponded to that determined by cleavage.

EXAMPLE 4

6-bromo-1-trityl resin-1H-indazol-3-amine

Trityl-resin bearing N'-(6-bromo-1H-indazol-3-yl)-N,N-dimethylimidoformamide (23.44 g) with a loading of 0.74 mmol/g was stirred in a 0.2 M solution of hydrazine hydrate (H$_2$N—NH$_2$H$_2$O) in pyridine/acetic acid 4/1 (VN) (250 ml) for 48 hours at 80° C. using a mechanical overhead stirrer. An aliquot of the slurry containing 10-50 mg of resin was removed from the reaction mixture, transferred into a sinter glass frit with a valve on its bottom and washed the following way:

3× a) 1 ml DMF; b) 1 ml H$_2$O
2× a) 1 ml MeOH; b) 1 ml DMF
1×1 ml MeOH
2× a) 1 ml toluene; 1 ml diethylether
3×1 ml diethylether.

The resin was dried in vacuo, then weighed.

From the known amount of resin the bound indazole was determined upon cleavage using TFA whereby collecting the cleavage solutions. The cleavage was performed the following way:

1×0.5 ml 20% TFA/DCM 5 min.
4×0.2 ml 20% TFA/DCM 2 min.

The combined cleavage solutions were combined and then dried in vacuo. The dried TFA-salt of the 6-bromo-3-amino indazole was weighed, and analyzed. The HPLC-trace at 215 nm indicated complete removal of the amidine protective group. If remaining starting material was still present, the amidine removal was allowed to continue for another day.

The bulk resin work up was performed as follows:

The slurry was transferred into a commercial "resin wash station" (Rink) an washed as follows: 3×700 ml DMF: The effluent from the washing vessel is collected to recover unused indazole.

3× a) 700 ml DMF; b) 700 ml $H_2O$
2× a) 700 ml MeOH; b) 700 ml DMF
1×700 ml MeOH
2× a) 700 ml toluene; 700 ml diisopropylether
3×700 ml diisopropylether.

The resin was dried in vacuo until constancy of weight.

EXAMPLE 5

6-(4methoxyphenyl)-1H-indazol-3-amine

A commercial "Miniblock" reactor was charged with trityl-resin bearing 6-bromo-1H-indazol-3-amine (95 mg, 0.066 mmol); 4-methoxyphenylboronic acid (0.3 mmol); $Pd_2dba_3$ (5 mg). Subsequently the reactor was sealed and the reaction mixture was put under inert atmosphere ($N_2$ or Ar).

The following solutions were prepared:

Triphenylphosphine in DME:

Triphenylphosphine (7.7 mmol, 2.02 g) was dissolved in DME (HPLC-grade) 275 ml. The pressure of the air in the headspace of the flask containing the solution was reduced to 20 mBar for 5 min., while being sonicated. Then headspace was filled with argon or nitrogen until ambient pressure was achieved. This process was repeated two more time to afford the solution sufficiently freed of oxygen.

10% aq. $K_3PO_4$:

The solution was prepared from $K_3PO_4$ and distilled or diionized water. The obtained solution was degassed and saturated with nitrogen or argon like the tripenylphosphine solution.

To the solids in the sealed reactor being under inert atmosphere was added degassed triphenylphosphine solution in DME (2 ml) and aq. $K_3PO_4$ solution (0.5 ml). The sealed reactor was shaken and heated to 80° C. for 48 hours.

The reaction solvent was drained and the resin was washed the following way:

3× a) 1 ml DMF; b) 1 ml $H_2O$
3× a) 1 ml MeOH; b) 1 ml DMF
3× a) 1 ml MeOH; b) 1 ml DCM
3× a) 1 ml DCM; b) diethyl ether
3× diethyl ether.

The resin may either be subjected to acylation reactions or the product may be cleaved directly.

The cleavage was performed the following way:

1×0.5 ml 20% TFA/DCM 5 min.
4×0.2 ml 20% TFA/DCM 2 min.

The combined cleavage solutions were combined and then dried. The solid, which may contain residual Pd was taken up in DMSO and filtered to remove particular matter such as Pd-metal.

The cleared DMSO solution was subjected to preparative reverse phase HPLC (C-18) using a gradient of water, 0.1% formic acid and MeCN 10-90% vol. within 8 min.

The product fractions were collected and those containing product pooled. Evaporation of the solvent then gave the dried 6-(4-methoxyphenyl)-1H-indazol-3-amine as a dried powder.

$[M+H]^+$=240.09; $^1$H-NMR (300 MHz DMSO-$d_6$): 11.33 (s, 1H); 7.7 (d, J=8, 1H); 7.61 (d, J=9, 2H); 7.33 (m, 1H); 7.14 (d of d J=8, J'=1, 1H); 7.01 (d, J=9, 2H); 5.3 (s, 2H); 3.79 (s, 3H)

By working in an analogous way the following products were cleaved from the resin:

6-(4-fluorophenyl)-1H-indazol-3-amine $[M+H]^+$=228.07; $^1$H-NMR (300 MHz DMSO-$d_6$): 11.41 (s, 1H); 7.74-7.68 (m, 3H); 7.37 (d, J=7.5, 1H); 7.26 (t, J=9, 2H); 7.16 (d, J=8, 1H); 5.33 (s, 2H).

6-thien-3-yl-1H-indazol-3-amine $[M+H]^+$=216.08; $^1$H-NMR (300 MHz DMSO-$d_6$): 11.36 (s, 1H); 7.85 (m, 1H); 7.66 (d, J=8, 1H); 7.63-7.60 (m, 1H); 7.57-7.55 (m, 1H); 7.46 (m, 1H); 7.25 (d of d, J=8, J'=1, 1H); 5.3 (s, 2H)

6-(1-naphthyl)-1H-indazol-3-amine $[M+H]^+$=260.15; $^1$H-NMR (300 MHz DMSO-$d_6$): 11.42 (s, 1H); 8.02-7.92 (4 m, 2H); 7.86-7.77 (4 s, 2H); 7.6-7.42 (m, 4H); 7.23 (m, 1H); 9.95-7 (d, J=9, 1H)

6-(2,6-dimethylphenyl)-1H-indazol-3-amine HPLC r.t. (Method I): 5.29; $[M+H]^+$=238.19

6-(1,3-benzodioxol-5-yl)-1H-indazol-3-amine HPLC r.t. (Method I): 4.47; $[M+H]^+$=254.1

6-(1-benzofuran-2-yl)-1H-indazol-3-amine HPLC r.t. (Method I): 5.43; $[M+H]^+$=250.7

6-(2,5-dimethylphenyl)-1H-indazol-3-amine HPLC r.t. (Method I): 5.42; $[M+H]^+$=238.2

1-[4-(3-amino-1H-indazol-6-yl)phenyl]ethanone HPLC r.t. (Method I): 4.06; $[M+H]^+$=252.1

6-(2-fluorophenyl)-1H-indazol-3-amine HPLC r.t. (Method I): 4.65; $[M+H]^+$=228.11

6-[4-(dimethylamino)phenyl]-1H-indazol-3-amine HPLC r.t. (Method II): 0.85 [M+H]+=253.1

6-(2,5-dimethoxyphenyl)-1H-indazol-3-amine HPLC r.t. (Method II): 1.12 [M+H]+=270.1

6-(3-methylphenyl)-1H-indazol-3-amine HPLC r.t. (Method II): 1.15 [M+H]+=224.1

6-(3-chlorophenyl)-1H-indazol-3-amine HPLC r.t. (Method II): 1.17 [M+H]+=244.1

6-(3-fluorophenyl)-1H-indazol-3-amine HPLC r.t. (Method II): 1.1 [M+H]+=228.1

6-(2,4-dimethoxyphenyl)-1H-indazol-3-amine HPLC r.t. (Method II): 1.09 [M+H]+=270.1

6-(2,5-difluorophenyl)-1H-indazol-3-amine HPLC r.t. (Method II): 1.1 [M+H]+=246.1

3-(3-amino-1H-indazol-6-yl)benzonitrile HPLC r.t. (Method II): 1.02 [M+H]+=235.1

6-(2,5-dimethylphenyl)-1H-indazol-3-amine HPLC r.t. (Method II): 1.2 [M+H]+=238.1

6-(5-fluoro-2-methoxyphenyl)-1H-indazol-3-amine HPLC r.t. (Method II): 1.1 [M+H]+=258.1

6-(2-methoxyphenyl)-1H-indazol-3-amine HPLC r.t. (Method II): 1.08 [M+H]+=240.1

EXAMPLE 6

N-(6bromo-1H-indazol-3-yl)-2,2-dimethylpropanamide

The reaction was performed in a "Miniblock" reactor (Bohdan) charged with Trityl-resin bearing 6-bromo-1H-indazol-3-amine. To resin (23.5 mg) bearing 6-bromo-1H-indazol-3-amine (1.2 mmol/g) was added N-methylimidazole (0.5 ml) distilled over sodium hydride, and a solution of pivaloyl chloride (0.5 mmol) in DCM (2 ml). The reaction mixture was shaken for 4 hours at room temperature.

The resin was washed as follows:
5× a) 1 ml DMF; b) 1 ml H$_2$O

The resulting imids of 6-bromo-1H-indazol-3-amine could be either isolated or converted to amides using an appropriate base such as aqueous ammonia. The ammonia treatment could be performed prior or post cleavage from the resin:

Aqueous ammonium hydroxide (20%) was dissolved in ice cold dioxane to afford a solution ammonia/dioxane 1:4 V/V. This solution was added to the appropriate reactor, which was then sealed and agitated at 55° C. for 48 hours. The resins were then washed
5× a) 1 ml DMF; b) 1 ml H$_2$O
5× a) 1 ml MeOH; b) 1 ml DCM
5× a) 1 ml DCM The cleavage was performed the following way:
1×0.5 ml 20% TFA/DCM 5 min.
4×0.2 ml 20% TFA/DCM 2 min.

The combined cleavage solutions were combined and then dried.

The solid, was taken up in DMSO and filtered to remove particular matter. The cleared DMSO solution was subjected to preparative reverse phase HPLC (C-18) using the instrument 1 (see above).

The product fractions were collected and those containing product pooled. Evaporation of the solvent then gave the dried N-(6-bromo-1H-indazol-3-yl)-2,2-dimethylpropanamide as a dried powder.

HPLC r.t. (Method I): 5.21; MS: [M+H]$^+$=298.08; [M–H]$^-$=296.08.

By working in an analogous way, starting from 6-bromo-1H-indazol-3-amine or 6-aryl-1H-indazol-3-amine derivatives (the latter being obtained according the procedure for 6-(4-methoxyphenyl)-1H-indazol-3-amine, the following products were cleaved from the resin:
N-(6-bromo-1H-indazol-3-yl)-2-phenylacetamide
    HPLC r.t. (Method I): 5.66; [M+H]$^+$=332.04.
N-(6-bromo-1H-indazol-3-yl)benzamide
    HPLC r.t. (Method I): 5.65; [M+H]$^+$=317.99; [M–H]$^-$=316.04.
N-(6-bromo-1H-indazol-3-yl)-2-methylbenzamide
    HPLC r.t. (Method I): 5.85; [M+H]$^+$=332.01; [M–H]$^-$=330.
N-(6-bromo-1H-indazol-3-yl)-2-methoxybenzamide
    HPLC r.t. (Method I): 6.13; [M+H]$^+$=348.03.
N-(6-bromo-1H-indazol-3-yl)-2-(trifluoromethyl)benzamide HPLC r.t. (Method I): 6.10; [M+H]$^+$=386.01; [M–H]$^-$=384.
N-(6-bromo-1H-indazol-3-yl)propanamide
    HPLC r.t. (Method I) 4.17; [M+H]$^+$=270; [M–H]$^-$=268.

By proceeding in the same way (example 6), 872 products were synthesized in parallel and coded in table X, as formerly indicated; related HPLC retention time (Method II) and the experimentally found [M+H]+ are reported.

TABLE X

| Entry | Compound | r.t. (min) | [M + H]+ |
|---|---|---|---|
| 1 | A15-M-B19 | 1.38 | 292.1 |
| 2 | A15-M-B3 | 1.4 | 294.2 |
| 3 | A15-M-B8 | 1.58 | 372.2 |
| 4 | A15-M-B25 | 1.51 | 320.2 |
| 5 | A15-M-B23 | 1.44 | 306.2 |
| 6 | A32-M-B37 | 1.36 | 391.2 |
| 7 | A32-M-B36 | 1.1 | 337.2 |
| 8 | A32-M-B8 | 1.3 | 415.2 |
| 9 | A24-M-B37 | 1.49 | 376.2 |
| 10 | A24-M-B31 | 1.51 | 400.2 |
| 11 | A24-M-B36 | 1.23 | 322.2 |
| 12 | A24-M-B19 | 1.2 | 320.1 |
| 13 | A24-M-B3 | 1.22 | 322.2 |
| 14 | A24-M-B8 | 1.42 | 400.2 |
| 15 | A24-M-B25 | 1.34 | 348.2 |
| 16 | A24-M-B23 | 1.27 | 334.2 |
| 17 | A12-M-B36 | 1.45 | 332.1 |
| 18 | A12-M-B19 | 1.42 | 330.1 |
| 19 | A12-M-B3 | 1.44 | 332.1 |
| 20 | A12-M-B8 | 1.61 | 410.1 |
| 21 | A12-M-B41 | 1.35 | 334.1 |
| 22 | A18-M-B36 | 1.43 | 314.1 |
| 23 | A18-M-B19 | 1.41 | 312.1 |
| 24 | A18-M-B3 | 1.43 | 314.1 |
| 25 | A18-M-B8 | 1.6 | 392.1 |
| 26 | A18-M-B41 | 1.34 | 316.1 |
| 27 | A18-M-B23 | 1.47 | 326.1 |
| 28 | A11-M-B3 | 1.53 | 348.1 |
| 29 | A11-M-B8 | 1.69 | 426.1 |
| 30 | A11-M-B41 | 1.43 | 350 |
| 31 | A31-M-B37 | 1.61 | 352.2 |
| 32 | A31-M-B19 | 1.33 | 296.1 |
| 33 | A31-M-B3 | 1.35 | 298.1 |
| 34 | A31-M-B8 | 1.52 | 376.1 |
| 35 | A31-M-B25 | 1.46 | 324.1 |
| 36 | A31-M-B41 | 1.26 | 300.1 |
| 37 | A31-M-B23 | 1.39 | 310.1 |
| 38 | A29-M-B37 | 1.73 | 418.2 |
| 39 | A29-M-B36 | 1.5 | 364.1 |
| 40 | A29-M-B19 | 1.48 | 362.1 |
| 41 | A29-M-B3 | 1.5 | 364.1 |
| 42 | A29-M-B8 | 1.66 | 442.1 |
| 43 | A29-M-B25 | 1.6 | 390.1 |
| 44 | A29-M-B23 | 1.53 | 376.1 |
| 45 | A15-M-B32 | 1.5 | 372.2 |
| 46 | A15-M-B4 | 1.69 | 418.2 |
| 47 | A15-M-B44 | 1.56 | 372.2 |
| 48 | A15-M-B29 | 1.41 | 318.1 |
| 49 | A15-M-B33 | 1.57 | 334.2 |
| 50 | A15-M-B11 | 1.58 | 358.2 |
| 51 | A15-M-B18 | 1.55 | 346.1 |
| 52 | A15-M-B17 | 1.63 | 362.1 |
| 53 | A15-M-B14 | 1.5 | 418.2 |
| 54 | A15-M-B16 | 1.77 | 396.1 |
| 55 | A15-M-B10 | 1.59 | 388.2 |
| 56 | A15-M-B9 | 1.55 | 382.1 |
| 57 | A32-M-B32 | 1.22 | 415.2 |
| 58 | A32-M-B4 | 1.43 | 461.2 |
| 59 | A32-M-B14 | 1.21 | 461.2 |
| 60 | A24-M-B4 | 1.55 | 446.2 |
| 61 | A24-M-B44 | 1.4 | 400.2 |
| 62 | A24-M-B29 | 1.23 | 346.1 |
| 63 | A24-M-B33 | 1.4 | 362.2 |
| 64 | A24-M-B18 | 1.39 | 374.1 |
| 65 | A24-M-B17 | 1.46 | 390.1 |
| 66 | A24-M-B14 | 1.34 | 446.2 |
| 67 | A24-M-B10 | 1.43 | 416.2 |
| 68 | A24-M-B9 | 1.38 | 410.1 |
| 69 | A12-M-B44 | 1.6 | 410.1 |
| 70 | A12-M-B11 | 1.63 | 396.1 |
| 71 | A12-M-B14 | 1.54 | 456.1 |
| 72 | A12-M-B9 | 1.59 | 420 |
| 73 | A18-M-B44 | 1.59 | 392.1 |
| 74 | A18-M-B29 | 1.43 | 338.1 |
| 75 | A18-M-B11 | 1.62 | 378.1 |
| 76 | A18-M-B18 | 1.58 | 366.1 |
| 77 | A18-M-B14 | 1.53 | 438.1 |

TABLE X-continued

| Entry | Compound | r.t. (min) | [M + H]+ |
|---|---|---|---|
| 78 | A18-M-B16 | 1.79 | 416 |
| 79 | A18-M-B10 | 1.62 | 408.1 |
| 80 | A18-M-B9 | 1.58 | 402.1 |
| 81 | A11-M-B44 | 1.67 | 426.1 |
| 82 | A11-M-B18 | 1.68 | 400 |
| 83 | A11-M-B14 | 1.62 | 472.1 |
| 84 | A31-M-B4 | 1.65 | 422.2 |
| 85 | A31-M-B44 | 1.51 | 376.1 |
| 86 | A31-M-B33 | 1.52 | 338.2 |
| 87 | A31-M-B11 | 1.54 | 362.1 |
| 88 | A31-M-B14 | 1.45 | 422.1 |
| 89 | A31-M-B16 | 1.72 | 400 |
| 90 | A31-M-B10 | 1.54 | 392.1 |
| 91 | A31-M-B9 | 1.51 | 386.1 |
| 92 | A29-M-B44 | 1.64 | 442.1 |
| 93 | A29-M-B29 | 1.5 | 388.1 |
| 94 | A29-M-B11 | 1.67 | 428.1 |
| 95 | A29-M-B14 | 1.58 | 488.1 |
| 96 | A29-M-B9 | 1.63 | 452.1 |
| 97 | A15-M-B15 | 1.62 | 400.1 |
| 98 | A15-M-B43 | 1.59 | 392.1 |
| 99 | A15-M-B27 | 1.53 | 334.2 |
| 100 | A15-M-B1 | 1.59 | 525.2 |
| 101 | A15-M-B22 | 1.53 | 364.1 |
| 102 | A32-M-B43 | 1.32 | 435.1 |
| 103 | A32-M-B1 | 1.34 | 568.2 |
| 104 | A24-M-B27 | 1.37 | 362.2 |
| 105 | A24-M-B22 | 1.36 | 392.1 |
| 106 | A12-M-B15 | 1.65 | 438 |
| 107 | A12-M-B43 | 1.62 | 430 |
| 108 | A12-M-B22 | 1.57 | 402.1 |
| 109 | A18-M-B15 | 1.64 | 420 |
| 110 | A18-M-B12 | 1.54 | 400 |
| 111 | A18-M-B43 | 1.62 | 412.1 |
| 112 | A18-M-B22 | 1.56 | 384.1 |
| 113 | A11-M-B15 | 1.74 | 454 |
| 114 | A31-M-B43 | 1.55 | 396.1 |
| 115 | A31-M-B22 | 1.49 | 368.1 |
| 116 | A29-M-B15 | 1.69 | 470.1 |
| 117 | A29-M-B43 | 1.66 | 462.1 |
| 118 | A29-M-B22 | 1.61 | 434.1 |
| 119 | A15-M-B38 | 1.52 | 356.2 |
| 120 | A15-M-B24 | 1.48 | 353.1 |
| 121 | A15-M-B28 | 1.5 | 346.1 |
| 122 | A15-M-B13 | 1.48 | 364.1 |
| 123 | A15-M-B42 | 1.3 | 324.1 |
| 124 | A15-M-B6 | 1.5 | 400.2 |
| 125 | A24-M-B38 | 1.35 | 384.2 |
| 126 | A24-M-B28 | 1.33 | 374.1 |
| 127 | A24-M-B13 | 1.31 | 392.1 |
| 128 | A24-M-B42 | 1.12 | 352.1 |
| 129 | A24-M-B6 | 1.33 | 428.2 |
| 130 | A12-M-B39 | 1.5 | 346.1 |
| 131 | A12-M-B42 | 1.34 | 362.1 |
| 132 | A12-M-B6 | 1.54 | 438.1 |
| 133 | A18-M-B39 | 1.49 | 328.1 |
| 134 | A18-M-B28 | 1.53 | 366.1 |
| 135 | A18-M-B42 | 1.32 | 344.1 |
| 136 | A18-M-B6 | 1.52 | 420.1 |
| 137 | A11-M-B40 | 1.7 | 440.1 |
| 138 | A11-M-B42 | 1.42 | 378 |
| 139 | A11-M-B6 | 1.61 | 454.1 |
| 140 | A31-M-B38 | 1.47 | 360.1 |
| 141 | A31-M-B39 | 1.4 | 312.1 |
| 142 | A31-M-B28 | 1.45 | 350.1 |
| 143 | A31-M-B13 | 1.43 | 368.1 |
| 144 | A31-M-B42 | 1.24 | 328.1 |
| 145 | A31-M-B6 | 1.45 | 404.1 |
| 146 | A29-M-B42 | 1.4 | 394.1 |
| 147 | A29-M-B6 | 1.58 | 470.1 |
| 148 | A36-M-B37 | 1.55 | 352.2 |
| 149 | A36-M-B19 | 1.26 | 296.1 |
| 150 | A36-M-B8 | 1.47 | 376.1 |
| 151 | A36-M-B25 | 1.39 | 324.1 |
| 152 | A36-M-B23 | 1.32 | 310.1 |
| 153 | A6-M-B37 | 1.61 | 348.2 |
| 154 | A6-M-B25 | 1.46 | 320.2 |
| 155 | A6-M-B41 | 1.25 | 296.1 |
| 156 | A6-M-B23 | 1.39 | 306.2 |
| 157 | A17-M-B37 | 1.46 | 376.2 |
| 158 | A17-M-B19 | 1.16 | 320.1 |
| 159 | A17-M-B8 | 1.38 | 400.2 |
| 160 | A17-M-B25 | 1.3 | 348.2 |
| 161 | A17-M-B23 | 1.23 | 334.2 |
| 162 | A23-M-B37 | 1.49 | 359.2 |
| 163 | A23-M-B8 | 1.41 | 383.1 |
| 164 | A23-M-B25 | 1.33 | 331.2 |
| 165 | A23-M-B23 | 1.26 | 317.1 |
| 166 | A1-M-B2 | 1.17 | 288.1 |
| 167 | A1-M-B19 | 1.3 | 314.1 |
| 168 | A1-M-B3 | 1.32 | 316.1 |
| 169 | A1-M-B8 | 1.5 | 394.1 |
| 170 | A1-M-B41 | 1.22 | 318.1 |
| 171 | A1-M-B23 | 1.36 | 328.1 |
| 172 | A2-M-B37 | 1.52 | 394.2 |
| 173 | A2-M-B19 | 1.24 | 338.1 |
| 174 | A2-M-B3 | 1.26 | 340.2 |
| 175 | A2-M-B8 | 1.45 | 418.2 |
| 176 | A2-M-B25 | 1.37 | 366.2 |
| 177 | A2-M-B41 | 1.17 | 342.1 |
| 178 | A2-M-B23 | 1.3 | 352.2 |
| 179 | A16-M-B3 | 1.22 | 305.1 |
| 180 | A16-M-B23 | 1.26 | 317.1 |
| 181 | A36-M-B32 | 1.44 | 376.1 |
| 182 | A36-M-B4 | 1.64 | 422.2 |
| 183 | A36-M-B44 | 1.49 | 376.1 |
| 184 | A36-M-B29 | 1.34 | 322.1 |
| 185 | A36-M-B11 | 1.51 | 362.1 |
| 186 | A36-M-B18 | 1.49 | 350.1 |
| 187 | A36-M-B17 | 1.55 | 366.1 |
| 188 | A36-M-B14 | 1.43 | 422.1 |
| 189 | A36-M-B10 | 1.52 | 392.1 |
| 190 | A36-M-B9 | 1.49 | 386.1 |
| 191 | A6-M-B4 | 1.69 | 418.2 |
| 192 | A6-M-B44 | 1.55 | 372.2 |
| 193 | A6-M-B29 | 1.39 | 318.1 |
| 194 | A6-M-B33 | 1.56 | 334.2 |
| 195 | A6-M-B11 | 1.57 | 358.2 |
| 196 | A6-M-B18 | 1.54 | 346.1 |
| 197 | A6-M-B17 | 1.62 | 362.1 |
| 198 | A6-M-B14 | 1.49 | 418.2 |
| 199 | A6-M-B16 | 1.75 | 396.1 |
| 200 | A6-M-B10 | 1.58 | 388.2 |
| 201 | A6-M-B9 | 1.54 | 382.1 |
| 202 | A17-M-B32 | 1.35 | 400.2 |
| 203 | A17-M-B44 | 1.41 | 400.2 |
| 204 | A17-M-B29 | 1.24 | 346.1 |
| 205 | A17-M-B33 | 1.41 | 362.2 |
| 206 | A17-M-B11 | 1.42 | 386.1 |
| 207 | A17-M-B18 | 1.39 | 374.1 |
| 208 | A17-M-B17 | 1.47 | 390.1 |
| 209 | A17-M-B14 | 1.34 | 446.2 |
| 210 | A17-M-B16 | 1.6 | 424.1 |
| 211 | A17-M-B10 | 1.43 | 416.2 |
| 212 | A17-M-B9 | 1.4 | 410.1 |
| 213 | A23-M-B4 | 1.58 | 429.2 |
| 214 | A23-M-B44 | 1.44 | 383.1 |
| 215 | A23-M-B29 | 1.27 | 329.1 |
| 216 | A23-M-B33 | 1.44 | 345.2 |
| 217 | A23-M-B11 | 1.45 | 369.1 |
| 218 | A23-M-B18 | 1.42 | 357.1 |
| 219 | A23-M-B16 | 1.64 | 407 |
| 220 | A23-M-B9 | 1.42 | 393.1 |
| 221 | A1-M-B44 | 1.52 | 394.1 |
| 222 | A1-M-B11 | 1.54 | 380.1 |
| 223 | A1-M-B18 | 1.52 | 368.1 |
| 224 | A1-M-B14 | 1.46 | 440.1 |
| 225 | A1-M-B9 | 1.51 | 404.1 |
| 226 | A2-M-B32 | 1.42 | 418.2 |
| 227 | A2-M-B4 | 1.61 | 464.2 |
| 228 | A2-M-B44 | 1.47 | 418.2 |
| 229 | A2-M-B29 | 1.32 | 364.1 |
| 230 | A2-M-B33 | 1.47 | 380.2 |
| 231 | A2-M-B11 | 1.48 | 404.2 |

TABLE X-continued

| Entry | Compound | r.t. (min) | [M + H]+ |
|---|---|---|---|
| 232 | A2-M-B18 | 1.46 | 392.1 |
| 233 | A2-M-B17 | 1.52 | 408.1 |
| 234 | A2-M-B14 | 1.41 | 464.2 |
| 235 | A2-M-B10 | 1.49 | 434.2 |
| 236 | A2-M-B9 | 1.46 | 428.1 |
| 237 | A16-M-B4 | 1.58 | 429.2 |
| 238 | A16-M-B44 | 1.44 | 383.1 |
| 239 | A16-M-B11 | 1.45 | 369.1 |
| 240 | A16-M-B18 | 1.42 | 357.11 |
| 241 | A16-M-B14 | 1.37 | 429.15 |
| 242 | A16-M-B10 | 1.46 | 399.14 |
| 243 | A16-M-B9 | 1.42 | 393.09 |
| 244 | A36-M-B38 | 1.45 | 360.1 |
| 245 | A36-M-B20 | 1.49 | 368.1 |
| 246 | A36-M-B24 | 1.41 | 357.1 |
| 247 | A36-M-B28 | 1.42 | 350.1 |
| 248 | A36-M-B21 | 1.54 | 400 |
| 249 | A36-M-B42 | 1.22 | 328.1 |
| 250 | A36-M-B6 | 1.43 | 404.1 |
| 251 | A36-M-B35 | 1.39 | 352.1 |
| 252 | A6-M-B20 | 1.55 | 364.1 |
| 253 | A6-M-B24 | 1.47 | 353.1 |
| 254 | A6-M-B28 | 1.49 | 346.1 |
| 255 | A6-M-B42 | 1.28 | 324.1 |
| 256 | A6-M-B6 | 1.49 | 400.2 |
| 257 | A17-M-B39 | 1.27 | 336.2 |
| 258 | A17-M-B20 | 1.39 | 392.1 |
| 259 | A17-M-B24 | 1.31 | 381.1 |
| 260 | A17-M-B26 | 1.31 | 356.1 |
| 261 | A17-M-B28 | 1.33 | 374.1 |
| 262 | A17-M-B13 | 1.31 | 392.1 |
| 263 | A17-M-B21 | 1.43 | 424.1 |
| 264 | A17-M-B42 | 1.13 | 352.1 |
| 265 | A17-M-B6 | 1.34 | 428.2 |
| 266 | A23-M-B20 | 1.43 | 375.1 |
| 267 | A23-M-B26 | 1.34 | 339.1 |
| 268 | A23-M-B28 | 1.36 | 357.1 |
| 269 | A23-M-B13 | 1.34 | 375.1 |
| 270 | A23-M-B42 | 1.15 | 335.1 |
| 271 | A23-M-B6 | 1.36 | 411.1 |
| 272 | A1-M-B39 | 1.41 | 330.1 |
| 273 | A1-M-B20 | 1.52 | 386.1 |
| 274 | A1-M-B26 | 1.44 | 350.1 |
| 275 | A1-M-B28 | 1.46 | 368.1 |
| 276 | A1-M-B13 | 1.44 | 386.1 |
| 277 | A1-M-B42 | 1.26 | 346.1 |
| 278 | A1-M-B6 | 1.46 | 422.1 |
| 279 | A2-M-B20 | 1.47 | 410.1 |
| 280 | A2-M-B24 | 1.36 | 399.1 |
| 281 | A2-M-B28 | 1.4 | 392.1 |
| 282 | A2-M-B13 | 1.39 | 410.1 |
| 283 | A2-M-B21 | 1.51 | 442.1 |
| 284 | A2-M-B42 | 1.21 | 370.1 |
| 285 | A2-M-B6 | 1.41 | 446.2 |
| 286 | A16-M-B38 | 1.39 | 367.2 |
| 287 | A16-M-B28 | 1.36 | 357.1 |
| 288 | A16-M-B42 | 1.16 | 335.1 |
| 289 | A16-M-B6 | 1.37 | 411.1 |
| 290 | A36-M-B15 | 1.55 | 404.1 |
| 291 | A36-M-B43 | 1.53 | 396.1 |
| 292 | A36-M-B22 | 1.46 | 368.1 |
| 293 | A6-M-B15 | 1.61 | 400.1 |
| 294 | A6-M-B43 | 1.58 | 392.1 |
| 295 | A6-M-B22 | 1.52 | 364.1 |
| 296 | A17-M-B15 | 1.47 | 428.1 |
| 297 | A17-M-B43 | 1.45 | 420.1 |
| 298 | A17-M-B22 | 1.37 | 392.1 |
| 299 | A23-M-B15 | 1.49 | 411.1 |
| 300 | A23-M-B22 | 1.4 | 375.1 |
| 301 | A1-M-B15 | 1.58 | 422.1 |
| 302 | A1-M-B43 | 1.55 | 414.1 |
| 303 | A1-M-B1 | 1.56 | 547.2 |
| 304 | A2-M-B15 | 1.52 | 446.1 |
| 305 | A2-M-B12 | 1.42 | 426.1 |
| 306 | A2-M-B43 | 1.5 | 438.1 |
| 307 | A2-M-B27 | 1.44 | 380.2 |
| 308 | A2-M-B22 | 1.43 | 410.1 |
| 309 | A16-M-B15 | 1.49 | 411.1 |
| 310 | A16-M-B22 | 1.4 | 375.1 |
| 311 | A5-M-B37 | 1.55 | 394.21 |
| 312 | A5-M-B19 | 1.28 | 338.14 |
| 313 | A5-M-B3 | 1.3 | 340.16 |
| 314 | A5-M-B8 | 1.48 | 418.17 |
| 315 | A5-M-B25 | 1.41 | 366.17 |
| 316 | A5-M-B23 | 1.34 | 352.16 |
| 317 | A14-M-B2 | 1.34 | 280.14 |
| 318 | A14-M-B37 | 1.72 | 362.22 |
| 319 | A14-M-B19 | 1.45 | 306.15 |
| 320 | A14-M-B3 | 1.48 | 308.17 |
| 321 | A14-M-B25 | 1.58 | 334.18 |
| 322 | A14-M-B41 | 1.39 | 310.2 |
| 323 | A14-M-B23 | 1.51 | 320.2 |
| 324 | A34-M-B37 | 1.64 | 378.2 |
| 325 | A34-M-B19 | 1.37 | 322.2 |
| 326 | A34-M-B3 | 1.4 | 324.2 |
| 327 | A34-M-B8 | 1.57 | 402.2 |
| 328 | A34-M-B25 | 1.5 | 350.2 |
| 329 | A34-M-B41 | 1.32 | 326.1 |
| 330 | A34-M-B23 | 1.44 | 336.2 |
| 331 | A7-M-B2 | 1.25 | 296.1 |
| 332 | A7-M-B37 | 1.63 | 378.2 |
| 333 | A7-M-B8 | 1.56 | 402.2 |
| 334 | A7-M-B25 | 1.49 | 350.2 |
| 335 | A7-M-B23 | 1.43 | 336.2 |
| 336 | A9-M-B37 | 1.69 | 362.2 |
| 337 | A9-M-B31 | 1.53 | 386.2 |
| 338 | A9-M-B3 | 1.45 | 308.2 |
| 339 | A9-M-B8 | 1.62 | 386.2 |
| 340 | A9-M-B25 | 1.55 | 334.2 |
| 341 | A9-M-B23 | 1.49 | 320.2 |
| 342 | A10-M-B34 | 1.55 | 356.2 |
| 343 | A10-M-B2 | 1.32 | 280.1 |
| 344 | A10-M-B37 | 1.71 | 362.2 |
| 345 | A10-M-B19 | 1.44 | 306.2 |
| 346 | A10-M-B3 | 1.46 | 308.2 |
| 347 | A10-M-B8 | 1.63 | 386.2 |
| 348 | A25-M-B19 | 1.53 | 320.2 |
| 349 | A25-M-B3 | 1.54 | 322.2 |
| 350 | A25-M-B8 | 1.7 | 400.2 |
| 351 | A25-M-B41 | 1.47 | 324.2 |
| 352 | A25-M-B23 | 1.58 | 334.2 |
| 353 | A27-M-B34 | 1.09 | 371.2 |
| 354 | A27-M-B2 | 0.85 | 295.2 |
| 355 | A27-M-B37 | 1.23 | 377.2 |
| 356 | A27-M-B36 | 0.97 | 323.2 |
| 357 | A27-M-B19 | 0.94 | 321.2 |
| 358 | A27-M-B30 | 0.92 | 309.2 |
| 359 | A27-M-B3 | 0.97 | 323.2 |
| 360 | A27-M-B8 | 1.17 | 401.2 |
| 361 | A27-M-B25 | 1.07 | 349.2 |
| 362 | A27-M-B23 | 1.02 | 335.2 |
| 363 | A5-M-B32 | 1.39 | 418.2 |
| 364 | A5-M-B4 | 1.57 | 464.2 |
| 365 | A5-M-B44 | 1.45 | 418.2 |
| 366 | A5-M-B29 | 1.29 | 364.1 |
| 367 | A5-M-B33 | 1.44 | 380.2 |
| 368 | A5-M-B11 | 1.44 | 404.2 |
| 369 | A5-M-B18 | 1.43 | 392.1 |
| 370 | A5-M-B17 | 1.5 | 408.1 |
| 371 | A5-M-B14 | 1.39 | 464.2 |
| 372 | A5-M-B9 | 1.43 | 428.1 |
| 373 | A14-M-B32 | 1.54 | 386.2 |
| 374 | A14-M-B44 | 1.61 | 386.2 |
| 375 | A14-M-B29 | 1.47 | 332.1 |
| 376 | A14-M-B33 | 1.62 | 348.2 |
| 377 | A14-M-B11 | 1.61 | 372.2 |
| 378 | A14-M-B18 | 1.6 | 360.1 |
| 379 | A14-M-B17 | 1.67 | 376.1 |
| 380 | A14-M-B14 | 1.55 | 432.2 |
| 381 | A14-M-B9 | 1.6 | 396.1 |
| 382 | A34-M-B4 | 1.66 | 448.2 |
| 383 | A34-M-B44 | 1.53 | 402.2 |
| 384 | A34-M-B29 | 1.39 | 348.1 |
| 385 | A34-M-B33 | 1.55 | 364.2 |

TABLE X-continued

| Entry | Compound | r.t. (min) | [M + H]+ |
|---|---|---|---|
| 386 | A34-M-B11 | 1.55 | 388.2 |
| 387 | A34-M-B18 | 1.53 | 376.1 |
| 388 | A34-M-B17 | 1.6 | 392.1 |
| 389 | A34-M-B14 | 1.49 | 448.2 |
| 390 | A34-M-B10 | 1.56 | 418.2 |
| 391 | A34-M-B9 | 1.51 | 412.1 |
| 392 | A7-M-B4 | 1.65 | 448.2 |
| 393 | A7-M-B32 | 1.46 | 402.2 |
| 394 | A7-M-B44 | 1.52 | 402.2 |
| 395 | A7-M-B29 | 1.37 | 348.1 |
| 396 | A7-M-B33 | 1.53 | 364.2 |
| 397 | A7-M-B11 | 1.54 | 388.2 |
| 398 | A7-M-B18 | 1.51 | 376.1 |
| 399 | A7-M-B17 | 1.57 | 392.1 |
| 400 | A7-M-B14 | 1.47 | 448.2 |
| 401 | A7-M-B9 | 1.49 | 412.1 |
| 402 | A9-M-B32 | 1.52 | 386.2 |
| 403 | A9-M-B4 | 1.71 | 432.2 |
| 404 | A9-M-B29 | 1.44 | 332.1 |
| 405 | A9-M-B33 | 1.6 | 348.2 |
| 406 | A9-M-B18 | 1.57 | 360.1 |
| 407 | A9-M-B17 | 1.64 | 376.1 |
| 408 | A9-M-B14 | 1.52 | 432.2 |
| 409 | A9-M-B16 | 1.76 | 410.1 |
| 410 | A9-M-B9 | 1.56 | 396.1 |
| 411 | A10-M-B44 | 1.57 | 386.18 |
| 412 | A10-M-B29 | 1.45 | 332.13 |
| 413 | A10-M-B11 | 1.59 | 372.16 |
| 414 | A10-M-B18 | 1.57 | 360.14 |
| 415 | A10-M-B14 | 1.53 | 432.18 |
| 416 | A25-M-B29 | 1.52 | 346.15 |
| 417 | A25-M-B11 | 1.68 | 386.18 |
| 418 | A25-M-B14 | 1.59 | 446.2 |
| 419 | A25-M-B9 | 1.64 | 410.14 |
| 420 | A27-M-B32 | 1.09 | 401.19 |
| 421 | A27-M-B4 | 1.28 | 447.21 |
| 422 | A27-M-B44 | 1.15 | 401.19 |
| 423 | A27-M-B29 | 0.98 | 347.14 |
| 424 | A27-M-B33 | 1.12 | 363.21 |
| 425 | A27-M-B11 | 1.12 | 387.17 |
| 426 | A27-M-B17 | 1.17 | 391.12 |
| 427 | A27-M-B14 | 1.07 | 447.2 |
| 428 | A27-M-B16 | 1.27 | 425.1 |
| 429 | A27-M-B9 | 1.12 | 411.1 |
| 430 | A5-M-B15 | 1.54 | 446.1 |
| 431 | A5-M-B12 | 1.46 | 426.1 |
| 432 | A5-M-B43 | 1.53 | 438.1 |
| 433 | A5-M-B22 | 1.47 | 410.1 |
| 434 | A14-M-B12 | 1.62 | 394.1 |
| 435 | A14-M-B43 | 1.67 | 406.1 |
| 436 | A14-M-B22 | 1.62 | 378.1 |
| 437 | A34-M-B15 | 1.64 | 430.1 |
| 438 | A34-M-B12 | 1.54 | 410.1 |
| 439 | A34-M-B43 | 1.6 | 422.1 |
| 440 | A34-M-B22 | 1.57 | 394.1 |
| 441 | A7-M-B12 | 1.54 | 410.1 |
| 442 | A7-M-B15 | 1.64 | 430.1 |
| 443 | A7-M-B43 | 1.61 | 422.1 |
| 444 | A7-M-B22 | 1.56 | 394.1 |
| 445 | A9-M-B15 | 1.69 | 414.1 |
| 446 | A9-M-B12 | 1.59 | 394.1 |
| 447 | A9-M-B43 | 1.65 | 406.1 |
| 448 | A9-M-B27 | 1.61 | 348.2 |
| 449 | A9-M-B22 | 1.6 | 378.1 |
| 450 | A10-M-B15 | 1.71 | 414.1 |
| 451 | A10-M-B12 | 1.61 | 394.1 |
| 452 | A10-M-B43 | 1.67 | 406.1 |
| 453 | A10-M-B22 | 1.63 | 378.1 |
| 454 | A25-M-B15 | 1.78 | 428.1 |
| 455 | A25-M-B43 | 1.75 | 420.1 |
| 456 | A25-M-B22 | 1.71 | 392.2 |
| 457 | A27-M-B15 | 1.24 | 429.1 |
| 458 | A27-M-B43 | 1.24 | 421.1 |
| 459 | A27-M-B22 | 1.14 | 393.1 |
| 460 | A5-M-B38 | 1.46 | 402.2 |
| 461 | A5-M-B20 | 1.49 | 410.1 |
| 462 | A5-M-B24 | 1.42 | 399.1 |
| 463 | A5-M-B28 | 1.44 | 392.1 |
| 464 | A5-M-B13 | 1.43 | 410.1 |
| 465 | A5-M-B42 | 1.25 | 370.1 |
| 466 | A5-M-B6 | 1.45 | 446.2 |
| 467 | A5-M-B35 | 1.39 | 394.1 |
| 468 | A14-M-B24 | 1.58 | 367.2 |
| 469 | A14-M-B28 | 1.6 | 360.1 |
| 470 | A14-M-B13 | 1.58 | 378.1 |
| 471 | A14-M-B21 | 1.69 | 410.1 |
| 472 | A14-M-B42 | 1.42 | 338.1 |
| 473 | A14-M-B6 | 1.59 | 414.2 |
| 474 | A14-M-B35 | 1.55 | 362.1 |
| 475 | A34-M-B20 | 1.59 | 394.1 |
| 476 | A34-M-B24 | 1.51 | 383.1 |
| 477 | A34-M-B13 | 1.52 | 376.1 |
| 478 | A34-M-B13 | 1.51 | 394.1 |
| 479 | A34-M-B21 | 1.62 | 426.1 |
| 480 | A34-M-B42 | 1.35 | 354.1 |
| 481 | A34-M-B6 | 1.53 | 430.2 |
| 482 | A34-M-B35 | 1.49 | 378.1 |
| 483 | A7-M-B20 | 1.57 | 394.1 |
| 484 | A7-M-B24 | 1.5 | 383.1 |
| 485 | A7-M-B28 | 1.52 | 376.1 |
| 486 | A7-M-B13 | 1.49 | 394.1 |
| 487 | A7-M-B21 | 1.59 | 426.1 |
| 488 | A7-M-B42 | 1.34 | 354.1 |
| 489 | A7-M-B6 | 1.52 | 430.2 |
| 490 | A9-M-B38 | 1.58 | 370.2 |
| 491 | A9-M-B39 | 1.53 | 322.2 |
| 492 | A9-M-B20 | 1.62 | 378.1 |
| 493 | A9-M-B24 | 1.54 | 367.2 |
| 494 | A9-M-B26 | 1.55 | 342.2 |
| 495 | A9-M-B28 | 1.57 | 360.1 |
| 496 | A9-M-B13 | 1.56 | 378.1 |
| 497 | A9-M-B21 | 1.65 | 410.1 |
| 498 | A9-M-B42 | 1.39 | 338.1 |
| 499 | A9-M-B6 | 1.58 | 414.2 |
| 500 | A9-M-B35 | 1.53 | 362.1 |
| 501 | A10-M-B20 | 1.65 | 378.1 |
| 502 | A10-M-B28 | 1.57 | 360.1 |
| 503 | A10-M-B13 | 1.55 | 378.1 |
| 504 | A10-M-B21 | 1.67 | 410.1 |
| 505 | A10-M-B6 | 1.58 | 414.2 |
| 506 | A25-M-B40 | 1.72 | 414.2 |
| 507 | A25-M-B20 | 1.72 | 392.2 |
| 508 | A25-M-B24 | 1.64 | 381.2 |
| 509 | A25-M-B26 | 1.64 | 356.2 |
| 510 | A25-M-B28 | 1.67 | 374.2 |
| 511 | A25-M-B13 | 1.64 | 392.2 |
| 512 | A25-M-B42 | 1.47 | 352.2 |
| 513 | A25-M-B6 | 1.65 | 428.2 |
| 514 | A27-M-B39 | 1.07 | 337.2 |
| 515 | A27-M-B20 | 1.18 | 393.1 |
| 516 | A27-M-B24 | 1.09 | 382.2 |
| 517 | A27-M-B28 | 1.09 | 375.2 |
| 518 | A27-M-B42 | 0.93 | 353.2 |
| 519 | A27-M-B6 | 1.14 | 429.2 |
| 520 | A27-M-B35 | 1.09 | 377.1 |
| 521 | A30-M-B2 | 1.35 | 312.1 |
| 522 | A30-M-B37 | 1.71 | 394.2 |
| 523 | A30-M-B36 | 1.47 | 340.1 |
| 524 | A30-M-B3 | 1.47 | 340.1 |
| 525 | A30-M-B8 | 1.6 | 418.2 |
| 526 | A30-M-B41 | 1.4 | 342.1 |
| 527 | A30-M-B23 | 1.51 | 352.1 |
| 528 | A3-M-B37 | 1.72 | 406.2 |
| 529 | A3-M-B19 | 1.49 | 350.2 |
| 530 | A3-M-B3 | 1.48 | 352.2 |
| 531 | A3-M-B8 | 1.64 | 430.2 |
| 532 | A3-M-B25 | 1.59 | 378.2 |
| 533 | A3-M-B41 | 1.44 | 354.2 |
| 534 | A3-M-B23 | 1.54 | 364.2 |
| 535 | A8-M-B37 | 1.61 | 380.2 |
| 536 | A8-M-B31 | 1.45 | 404.1 |
| 537 | A8-M-B36 | 1.37 | 326.1 |
| 538 | A8-M-B19 | 1.35 | 324.1 |
| 539 | A8-M-B3 | 1.37 | 326.1 |

TABLE X-continued

| Entry | Compound | r.t. (min) | [M + H]+ |
|---|---|---|---|
| 540 | A8-M-B8 | 1.53 | 404.1 |
| 541 | A8-M-B25 | 1.46 | 352.1 |
| 542 | A8-M-B41 | 1.29 | 328.1 |
| 543 | A8-M-B23 | 1.4 | 338.1 |
| 544 | A33-M-B37 | 1.71 | 418.2 |
| 545 | A33-M-B36 | 1.49 | 364.1 |
| 546 | A33-M-B3 | 1.49 | 364.1 |
| 547 | A33-M-B8 | 1.6 | 442.1 |
| 548 | A33-M-B25 | 1.57 | 390.1 |
| 549 | A20-M-B34 | 1.54 | 356.2 |
| 550 | A20-M-B2 | 1.31 | 280.1 |
| 551 | A20-M-B37 | 1.67 | 362.2 |
| 552 | A20-M-B36 | 1.45 | 308.2 |
| 553 | A20-M-B19 | 1.43 | 306.2 |
| 554 | A20-M-B3 | 1.46 | 308.2 |
| 555 | A20-M-B8 | 1.61 | 386.2 |
| 556 | A20-M-B25 | 1.54 | 334.2 |
| 557 | A20-M-B41 | 1.37 | 310.2 |
| 558 | A20-M-B23 | 1.48 | 320.2 |
| 559 | A4-M-B2 | 1.21 | 288.1 |
| 560 | A4-M-B37 | 1.59 | 370.2 |
| 561 | A4-M-B31 | 1.44 | 394.1 |
| 562 | A4-M-B36 | 1.35 | 316.1 |
| 563 | A4-M-B19 | 1.33 | 314.1 |
| 564 | A4-M-B3 | 1.35 | 316.1 |
| 565 | A4-M-B8 | 1.47 | 394.1 |
| 566 | A4-M-B25 | 1.44 | 342.1 |
| 567 | A4-M-B41 | 1.26 | 318.1 |
| 568 | A4-M-B23 | 1.38 | 328.1 |
| 569 | A13-M-B2 | 1.23 | 288.1 |
| 570 | A13-M-B37 | 1.61 | 370.2 |
| 571 | A13-M-B8 | 1.53 | 394.1 |
| 572 | A13-M-B41 | 1.29 | 318.1 |
| 573 | A13-M-B23 | 1.41 | 328.1 |
| 574 | A21-M-B2 | 1.21 | 300.1 |
| 575 | A21-M-B37 | 1.57 | 382.2 |
| 576 | A21-M-B19 | 1.31 | 326.1 |
| 577 | A21-M-B3 | 1.34 | 328.1 |
| 578 | A21-M-B8 | 1.5 | 406.2 |
| 579 | A21-M-B25 | 1.43 | 354.2 |
| 580 | A21-M-B41 | 1.25 | 330.1 |
| 581 | A21-M-B23 | 1.35 | 340.1 |
| 582 | A30-M-B29 | 1.44 | 364.1 |
| 583 | A30-M-B33 | 1.58 | 380.2 |
| 584 | A30-M-B14 | 1.52 | 464.2 |
| 585 | A30-M-B10 | 1.61 | 434.2 |
| 586 | A30-M-B9 | 1.55 | 428.2 |
| 587 | A3-M-B32 | 1.53 | 430.2 |
| 588 | A3-M-B4 | 1.71 | 476.2 |
| 589 | A3-M-B29 | 1.46 | 376.2 |
| 590 | A3-M-B33 | 1.6 | 392.2 |
| 591 | A3-M-B11 | 1.61 | 416.2 |
| 592 | A3-M-B17 | 1.65 | 420.1 |
| 593 | A3-M-B14 | 1.54 | 476.2 |
| 594 | A3-M-B16 | 1.79 | 454.1 |
| 595 | A3-M-B10 | 1.62 | 446.2 |
| 596 | A3-M-B9 | 1.59 | 440.2 |
| 597 | A8-M-B32 | 1.43 | 404.1 |
| 598 | A8-M-B4 | 1.61 | 450.2 |
| 599 | A8-M-B44 | 1.48 | 404.1 |
| 600 | A8-M-B33 | 1.49 | 366.2 |
| 601 | A8-M-B11 | 1.5 | 390.1 |
| 602 | A8-M-B17 | 1.54 | 394.1 |
| 603 | A8-M-B14 | 1.42 | 450.1 |
| 604 | A8-M-B16 | 1.66 | 428 |
| 605 | A8-M-B10 | 1.5 | 420.1 |
| 606 | A8-M-B9 | 1.47 | 414.1 |
| 607 | A33-M-B4 | 1.69 | 488.2 |
| 608 | A33-M-B44 | 1.57 | 442.1 |
| 609 | A33-M-B29 | 1.44 | 388.08 |
| 610 | A33-M-B33 | 1.58 | 404.15 |
| 611 | A33-M-B14 | 1.52 | 488.14 |
| 612 | A33-M-B10 | 1.6 | 458.12 |
| 613 | A33-M-B9 | 1.56 | 452.08 |
| 614 | A20-M-B32 | 1.5 | 386.18 |
| 615 | A20-M-B4 | 1.68 | 432.2 |
| 616 | A20-M-B44 | 1.55 | 386.18 |
| 617 | A20-M-B29 | 1.42 | 332.13 |
| 618 | A20-M-B17 | 1.62 | 376.11 |
| 619 | A20-M-B14 | 1.5 | 432.18 |
| 620 | A20-M-B16 | 1.76 | 410.07 |
| 621 | A20-M-B9 | 1.55 | 396.12 |
| 622 | A4-M-B32 | 1.41 | 394.13 |
| 623 | A4-M-B4 | 1.59 | 440.15 |
| 624 | A4-M-B29 | 1.31 | 340.08 |
| 625 | A4-M-B33 | 1.47 | 356.15 |
| 626 | A4-M-B14 | 1.4 | 440.13 |
| 627 | A4-M-B9 | 1.44 | 404.1 |
| 628 | A13-M-B44 | 1.48 | 394.1 |
| 629 | A13-M-B29 | 1.34 | 340.1 |
| 630 | A13-M-B11 | 1.5 | 380.1 |
| 631 | A13-M-B17 | 1.53 | 384.1 |
| 632 | A13-M-B14 | 1.42 | 440.1 |
| 633 | A13-M-B9 | 1.47 | 404.1 |
| 634 | A21-M-B32 | 1.39 | 406.2 |
| 635 | A21-M-B4 | 1.56 | 452.2 |
| 636 | A21-M-B44 | 1.45 | 406.2 |
| 637 | A21-M-B29 | 1.3 | 352.1 |
| 638 | A21-M-B33 | 1.45 | 368.2 |
| 639 | A21-M-B11 | 1.46 | 392.1 |
| 640 | A21-M-B17 | 1.5 | 396.1 |
| 641 | A21-M-B14 | 1.39 | 452.2 |
| 642 | A21-M-B10 | 1.46 | 422.1 |
| 643 | A21-M-B9 | 1.43 | 416.1 |
| 644 | A30-M-B15 | 1.7 | 446.1 |
| 645 | A30-M-B22 | 1.62 | 410.1 |
| 646 | A3-M-B15 | 1.72 | 458.1 |
| 647 | A3-M-B43 | 1.7 | 450.2 |
| 648 | A3-M-B27 | 1.65 | 392.2 |
| 649 | A3-M-B22 | 1.64 | 422.2 |
| 650 | A8-M-B15 | 1.59 | 432.1 |
| 651 | A8-M-B43 | 1.57 | 424.1 |
| 652 | A8-M-B27 | 1.51 | 366.2 |
| 653 | A8-M-B22 | 1.51 | 396.1 |
| 654 | A33-M-B15 | 1.69 | 470.1 |
| 655 | A33-M-B43 | 1.66 | 462.1 |
| 656 | A33-M-B22 | 1.61 | 434.1 |
| 657 | A20-M-B15 | 1.68 | 414.1 |
| 658 | A20-M-B12 | 1.58 | 394.1 |
| 659 | A20-M-B43 | 1.65 | 406.1 |
| 660 | A20-M-B27 | 1.6 | 348.2 |
| 661 | A20-M-B1 | 1.64 | 539.2 |
| 662 | A20-M-B22 | 1.6 | 378.1 |
| 663 | A4-M-B15 | 1.58 | 422.1 |
| 664 | A4-M-B12 | 1.47 | 402.1 |
| 665 | A4-M-B22 | 1.49 | 386.1 |
| 666 | A13-M-B15 | 1.59 | 422.1 |
| 667 | A13-M-B43 | 1.57 | 414.1 |
| 668 | A13-M-B22 | 1.51 | 386.1 |
| 669 | A21-M-B15 | 1.56 | 434.1 |
| 670 | A21-M-B43 | 1.54 | 426.1 |
| 671 | A21-M-B22 | 1.47 | 398.1 |
| 672 | A30-M-B13 | 1.56 | 410.1 |
| 673 | A30-M-B42 | 1.39 | 370.1 |
| 674 | A30-M-B6 | 1.57 | 446.2 |
| 675 | A3-M-B38 | 1.63 | 414.2 |
| 676 | A3-M-B39 | 1.57 | 366.2 |
| 677 | A3-M-B20 | 1.66 | 422.2 |
| 678 | A3-M-B24 | 1.59 | 411.2 |
| 679 | A3-M-B26 | 1.59 | 386.2 |
| 680 | A3-M-B28 | 1.61 | 404.2 |
| 681 | A3-M-B13 | 1.59 | 422.2 |
| 682 | A3-M-B21 | 1.71 | 454.1 |
| 683 | A3-M-B42 | 1.42 | 382.2 |
| 684 | A3-M-B6 | 1.61 | 458.2 |
| 685 | A3-M-B35 | 1.57 | 406.2 |
| 686 | A8-M-B38 | 1.49 | 388.1 |
| 687 | A8-M-B20 | 1.53 | 396.1 |
| 688 | A8-M-B24 | 1.45 | 385.1 |
| 689 | A8-M-B28 | 1.47 | 378.1 |
| 690 | A8-M-B13 | 1.45 | 396.1 |
| 691 | A8-M-B21 | 1.58 | 428 |
| 692 | A8-M-B42 | 1.27 | 356.1 |
| 693 | A8-M-B6 | 1.47 | 432.1 |

TABLE X-continued

| Entry | Compound | r.t. (min) | [M + H]+ |
|---|---|---|---|
| 694 | A8-M-B35 | 1.43 | 380.1 |
| 695 | A33-M-B20 | 1.63 | 434.1 |
| 696 | A33-M-B24 | 1.55 | 423.1 |
| 697 | A33-M-B28 | 1.58 | 416.1 |
| 698 | A33-M-B13 | 1.56 | 434.1 |
| 699 | A33-M-B42 | 1.39 | 394.1 |
| 700 | A33-M-B6 | 1.57 | 470.1 |
| 701 | A20-M-B38 | 1.58 | 370.2 |
| 702 | A20-M-B39 | 1.52 | 322.2 |
| 703 | A20-M-B20 | 1.62 | 378.1 |
| 704 | A20-M-B24 | 1.54 | 367.2 |
| 705 | A20-M-B26 | 1.54 | 342.2 |
| 706 | A20-M-B28 | 1.56 | 360.1 |
| 707 | A20-M-B13 | 1.54 | 378.1 |
| 708 | A20-M-B42 | 1.36 | 338.1 |
| 709 | A20-M-B6 | 1.56 | 414.2 |
| 710 | A20-M-B35 | 1.51 | 362.1 |
| 711 | A4-M-B38 | 1.48 | 378.1 |
| 712 | A4-M-B39 | 1.41 | 330.1 |
| 713 | A4-M-B26 | 1.43 | 350.1 |
| 714 | A4-M-B28 | 1.46 | 368.1 |
| 715 | A4-M-B13 | 1.43 | 386.1 |
| 716 | A4-M-B21 | 1.55 | 418 |
| 717 | A4-M-B42 | 1.25 | 346.1 |
| 718 | A4-M-B6 | 1.46 | 422.1 |
| 719 | A13-M-B13 | 1.46 | 386.1 |
| 720 | A13-M-B6 | 1.48 | 422.1 |
| 721 | A21-M-B38 | 1.46 | 390.2 |
| 722 | A21-M-B20 | 1.49 | 398.1 |
| 723 | A21-M-B24 | 1.42 | 387.1 |
| 724 | A21-M-B28 | 1.44 | 380.1 |
| 725 | A21-M-B13 | 1.42 | 398.1 |
| 726 | A21-M-B42 | 1.24 | 358.1 |
| 727 | A21-M-B6 | 1.44 | 434.1 |
| 728 | A21-M-B35 | 1.4 | 382.1 |
| 729 | A38-M-B15 | 1.53 | 392 |
| 730 | A38-M-B22 | 1.44 | 356.1 |
| 731 | A37-M-B15 | 1.54 | 416.1 |
| 732 | A37-M-B43 | 1.52 | 408.1 |
| 733 | A37-M-B27 | 1.45 | 350.2 |
| 734 | A37-M-B22 | 1.45 | 380.1 |
| 735 | A22-M-B15 | 1.63 | 400.1 |
| 736 | A22-M-B43 | 1.59 | 392.1 |
| 737 | A22-M-B27 | 1.54 | 334.2 |
| 738 | A22-M-B22 | 1.54 | 364.1 |
| 739 | A35-M-B15 | 1.55 | 386.1 |
| 740 | A35-M-B43 | 1.53 | 378.1 |
| 741 | A35-M-B27 | 1.46 | 320.2 |
| 742 | A35-M-B22 | 1.46 | 350.1 |
| 743 | A39-M-B22 | 1.42 | 356.1 |
| 744 | A19-M-B15 | 1.54 | 416.1 |
| 745 | A19-M-B43 | 1.53 | 408.1 |
| 746 | A19-M-B27 | 1.46 | 350.2 |
| 747 | A19-M-B1 | 1.53 | 541.2 |
| 748 | A19-M-B22 | 1.46 | 380.1 |
| 749 | A26-M-B15 | 1.56 | 404.1 |
| 750 | A26-M-B43 | 1.54 | 396.1 |
| 751 | A26-M-B22 | 1.48 | 368.1 |
| 752 | A28-M-B22 | 1.45 | 380.1 |
| 753 | A28-M-B2 | 1.17 | 282.1 |
| 754 | A28-M-B37 | 1.56 | 364.2 |
| 755 | A28-M-B36 | 1.31 | 310.2 |
| 756 | A28-M-B19 | 1.28 | 308.1 |
| 757 | A28-M-B30 | 1.24 | 296.1 |
| 758 | A28-M-B3 | 1.31 | 310.2 |
| 759 | A28-M-B8 | 1.49 | 388.2 |
| 760 | A28-M-B25 | 1.41 | 336.2 |
| 761 | A28-M-B41 | 1.22 | 312.1 |
| 762 | A26-M-B34 | 1.44 | 346.1 |
| 763 | A26-M-B2 | 1.2 | 270.1 |
| 764 | A26-M-B37 | 1.59 | 352.2 |
| 765 | A26-M-B31 | 1.43 | 376.1 |
| 766 | A26-M-B36 | 1.34 | 298.1 |
| 767 | A26-M-B19 | 1.32 | 296.1 |
| 768 | A26-M-B30 | 1.27 | 284.1 |
| 769 | A26-M-B3 | 1.34 | 298.1 |
| 770 | A26-M-B8 | 1.52 | 376.1 |
| 771 | A26-M-B25 | 1.44 | 324.1 |
| 772 | A26-M-B41 | 1.25 | 300.1 |
| 773 | A19-M-B34 | 1.42 | 358.2 |
| 774 | A19-M-B2 | 1.18 | 282.1 |
| 775 | A19-M-B37 | 1.57 | 364.2 |
| 776 | A19-M-B36 | 1.32 | 310.2 |
| 777 | A19-M-B19 | 1.3 | 308.1 |
| 778 | A19-M-B30 | 1.25 | 296.1 |
| 779 | A19-M-B3 | 1.32 | 310.2 |
| 780 | A19-M-B8 | 1.49 | 388.2 |
| 781 | A19-M-B25 | 1.42 | 336.2 |
| 782 | A19-M-B41 | 1.23 | 312.1 |
| 783 | A39-M-B2 | 1.14 | 258.1 |
| 784 | A39-M-B37 | 1.52 | 340.1 |
| 785 | A39-M-B36 | 1.28 | 286.1 |
| 786 | A39-M-B19 | 1.25 | 284.1 |
| 787 | A39-M-B30 | 1.21 | 272.1 |
| 788 | A39-M-B3 | 1.28 | 286.1 |
| 789 | A39-M-B8 | 1.46 | 364.1 |
| 790 | A39-M-B25 | 1.39 | 312.1 |
| 791 | A35-M-B2 | 1.18 | 252.1 |
| 792 | A35-M-B37 | 1.57 | 334.2 |
| 793 | A35-M-B36 | 1.33 | 280.1 |
| 794 | A35-M-B19 | 1.29 | 278.1 |
| 795 | A35-M-B30 | 1.25 | 266.1 |
| 796 | A35-M-B3 | 1.32 | 280.1 |
| 797 | A35-M-B8 | 1.5 | 358.2 |
| 798 | A35-M-B25 | 1.43 | 306.2 |
| 799 | A35-M-B41 | 1.23 | 282.1 |
| 800 | A22-M-B34 | 1.49 | 342.2 |
| 801 | A22-M-B2 | 1.27 | 266.1 |
| 802 | A22-M-B37 | 1.64 | 348.2 |
| 803 | A22-M-B36 | 1.4 | 294.2 |
| 804 | A22-M-B19 | 1.37 | 292.1 |
| 805 | A22-M-B30 | 1.33 | 280.1 |
| 806 | A22-M-B3 | 1.4 | 294.2 |
| 807 | A22-M-B8 | 1.57 | 372.2 |
| 808 | A22-M-B25 | 1.5 | 320.2 |
| 809 | A22-M-B41 | 1.32 | 296.1 |
| 810 | A37-M-B2 | 1.18 | 282.1 |
| 811 | A37-M-B37 | 1.55 | 364.2 |
| 812 | A37-M-B36 | 1.31 | 310.2 |
| 813 | A37-M-B19 | 1.29 | 308.1 |
| 814 | A37-M-B30 | 1.24 | 296.1 |
| 815 | A37-M-B3 | 1.31 | 310.2 |
| 816 | A37-M-B8 | 1.49 | 388.2 |
| 817 | A37-M-B25 | 1.41 | 336.2 |
| 818 | A37-M-B41 | 1.22 | 312.1 |
| 819 | A38-M-B2 | 1.14 | 258.1 |
| 820 | A38-M-B37 | 1.54 | 340.1 |
| 821 | A38-M-B36 | 1.29 | 286.1 |
| 822 | A38-M-B19 | 1.27 | 284.1 |
| 823 | A38-M-B3 | 1.29 | 286.1 |
| 824 | A38-M-B8 | 1.47 | 364.1 |
| 825 | A38-M-B25 | 1.39 | 312.1 |
| 826 | A38-M-B41 | 1.2 | 288.1 |
| 827 | A28-M-B23 | 1.36 | 322.2 |
| 828 | A28-M-B32 | 1.42 | 388.2 |
| 829 | A28-M-B4 | 1.6 | 434.18 |
| 830 | A28-M-B29 | 1.33 | 334.11 |
| 831 | A28-M-B33 | 1.48 | 350.2 |
| 832 | A26-M-B23 | 1.39 | 310.13 |
| 833 | A26-M-B32 | 1.44 | 376.1 |
| 834 | A26-M-B4 | 1.64 | 422.16 |
| 835 | A26-M-B44 | 1.51 | 376.14 |
| 836 | A26-M-B29 | 1.36 | 322.1 |
| 837 | A26-M-B33 | 1.52 | 338.2 |
| 838 | A19-M-B23 | 1.37 | 322.2 |
| 839 | A19-M-B32 | 1.43 | 388.2 |
| 840 | A19-M-B4 | 1.62 | 434.2 |
| 841 | A19-M-B5 | 1.57 | 386.18 |
| 842 | A19-M-B44 | 1.49 | 388.16 |
| 843 | A19-M-B29 | 1.34 | 334.11 |
| 844 | A19-M-B33 | 1.49 | 350.18 |
| 845 | A19-M-B7 | 1.39 | 324.16 |
| 846 | A39-M-B23 | 1.33 | 298.09 |
| 847 | A39-M-B32 | 1.4 | 364.1 |

TABLE X-continued

| Entry | Compound | r.t. (min) | [M + H]+ |
|---|---|---|---|
| 848 | A39-M-B4 | 1.59 | 410.12 |
| 849 | A39-M-B44 | 1.46 | 364.1 |
| 850 | A39-M-B29 | 1.3 | 310.06 |
| 851 | A39-M-B33 | 1.46 | 326.12 |
| 852 | A35-M-B23 | 1.37 | 292.14 |
| 853 | A35-M-B4 | 1.62 | 404.17 |
| 854 | A35-M-B44 | 1.49 | 358.15 |
| 855 | A35-M-B29 | 1.34 | 304.1 |
| 856 | A35-M-B7 | 1.39 | 294.15 |
| 857 | A22-M-B23 | 1.45 | 306.15 |
| 858 | A22-M-B4 | 1.68 | 418.18 |
| 859 | A22-M-B44 | 1.56 | 372.16 |
| 860 | A22-M-B29 | 1.41 | 318.12 |
| 861 | A22-M-B33 | 1.57 | 334.18 |
| 862 | A37-M-B23 | 1.36 | 322.15 |
| 863 | A37-M-B32 | 1.42 | 388.16 |
| 864 | A37-M-B4 | 1.61 | 434.18 |
| 865 | A37-M-B44 | 1.48 | 388.16 |
| 866 | A37-M-B29 | 1.33 | 334.11 |
| 867 | A37-M-B33 | 1.47 | 350.18 |
| 868 | A38-M-B23 | 1.35 | 298.09 |
| 869 | A38-M-B32 | 1.4 | 364.1 |
| 870 | A38-M-B4 | 1.6 | 410.12 |
| 871 | A38-M-B44 | 1.47 | 364.1 |
| 872 | A38-M-B29 | 1.31 | 310.06 |

EXAMPLE 7

N-isopropyl-N'-[6-(4-methoxyphenyl)-1H-indazol-3-yl]urea

The reaction was performed in a "Miniblock" reactor (Bohdan) charged with trityl-resin bearing 6-(4-methoxyphenyl)-1H-indazol-3-amine, obtained according to the procedure previously described.

To resin (70 mg) bearing 6-(4-methoxyphenyl)-1H-indazol-3-amine (1.2 mmol/g) was added isopropyl isocyanate (0.2 mmol) in pyridine (2 ml). The reaction mixture was shaken for 48 hours at 55° C.

The resin was washed as follows:
5× a) 1 ml DMF; b) 1 ml $H_2O$

The resulting imids of 6-(4-methoxyphenyl)-1H-indazol-3-amine could be either isolated or converted to amids using an appropriate base such as aqueous ammonia. The ammonia treatment could be performed prior or post cleavage from the resin:

Aqueous $NH_4OH$ (20%) was dissolved in ice cold dioxane to afford a solution ammonia/dioxane 1:4 V/V. This solution was added to the appropriate reactor, which was then sealed and agitated at 55° C. for 48 hours. The resins were then washed
5× a) 1 ml DMF; b) 1 ml $H_2O$
5× a) 1 ml MeOH; b) 1 ml DCM
5× a) 1 ml DCM The cleavage was performed the following way:
1×0.5 ml 20% TFA/DCM 5 min.
4×0.2 ml 20% TFA/DCM 2 min.

The cleavage solutions were combined and then dried. The solid, was taken up in dimethylsulfoxyde and filtered to remove particular matter. The cleared DMSO solution was subjected to preparative reverse phase HPLC (C-18) using the instrument 1 (see above)

The product fractions were collected and those containing product pooled. Evaporation of the solvent then gave the dried N-isopropyl-N'-[6-(4-methoxyphenyl)-1H-indazol-3-yl]urea as a dried powder HPLC r.t. (Method I): 5.61; $[M+H]^+=325.33$ The cleavage solutions were combined and then dried.

By working in an analogous way, starting from 6-aryl-1H-indazol-3-amines derivatives (obtained according to the procedure for 6-(4-methoxyphenyl)-1H-indazol-3-amine), the following products were cleaved from the resin:

ethyl N-({[6-(3-methoxyphenyl)-1H-indazol-3-yl]amino}carbonyl)glycinate HPLC r.t. (Method I); 5.26; $[M+H]^+=369.29$ N-ethyl-N'-[6-(3-methoxyphenyl)-1H-indazol-3-yl]urea HPLC r.t. (Method I): 5.14; $[M+H]^+=311.33$ N-[6-(3-methoxyphenyl)-1H-indazol-3-yl]-N'-propylurea HPLC r.t. (Method I): 5.66; $[M+H]^+=325.33$ N-{3-[3-({[(2-methoxyphenyl)amino]carbonyl}amino)-1H-indazol-6-yl]phenyl}acetamide HPLC r.t. (Method I): 5.57; $[M+H]^+=416.28$ ethyl N-[({6-[3-(acetylamino)phenyl]-1H-indazol-3-yl}amino)carbonyl]glycinate HPLC r.t. (Method I): 4.17; $[M+H]^+=396.3$ ethyl N-({[6-(3-fluorophenyl)-1H-indazol-3-yl]amino}carbonyl)glycinate HPLC r.t. (Method I): 5.45; $[M+H]^+=357.28$ N-[6-(3-fluorophenyl)-1H-indazol-3-yl]-N'-propylurea HPLC r.t. (Method I): 5.88; $[M+H]^+=313.35$ N-[6-(2-fluorophenyl)-1H-indazol-3-yl]-N'-isopropylurea HPLC r.t. (Method I): 5.7; $[M+H]^+=313.35$ ethyl N-({[6-(2-fluorophenyl)-1H-indazol-3-yl]amino}carbonyl)glycinate HPLC r.t. (Method I): 5.33; $[M+H]^+=357.28$ N-ethyl-N'-[6-(2-fluorophenyl)-1H-indazol-3-yl]urea HPLC r.t. (Method I): 5.21; $[M+H]^+=299.34$ N-[6-(2-fluorophenyl)-1H-indazol-3-yl]-N'-propylurea HPLC r.t. (Method I): 5.76; $[M+H]^+=313.35$ N-{6-[4-(hydroxymethyl)phenyl]-1H-indazol-3-yl}-N'-isopropylurea HPLC r.t. (Method I): 4.17; $[M+H]^+=325.33$ N-ethyl-N'-{6-[4-(hydroxymethyl)phenyl]-1H-indazol-3-yl}urea HPLC r.t. (Method I): 3.7; $[M+H]^+=311.31$ N-{6-[4-(hydroxymethyl)phenyl]-1H-indazol-3-yl}-N'-propylurea HPLC r.t. (Method I): 4.48; $[M+H]^+=325.33$

EXAMPLE 8

N-butyl-N'-[6-(4-fluorophenyl)-1H-indazol-3-yl]urea

The reaction was performed in a "Miniblock" reactor (Bohdan) charged with trityl-resin bearing 6-(4-fluorophenyl)-1H-indazol-3-amine, obtained according to the procedure previously described.

To the resin (9.0 g, 0.7 mmol/g, 6.3 mmol) in anhydrous DCM (100 ml) was added triethylamine (6.363 g, 63.0 mmol) and phenylchloroformate (9.860 g, 63 mmol). The reaction mixture was shaken at room temperature for 18 h and the resin isolated by filtration. The resin was washed sequentially with DMF (50 ml), DCM (50 ml), DMF (50 ml), DCM (50 ml), MeOH (50 ml), DCM (50 ml), MeOH (50 ml), DCM (50 ml), MeOH (50 ml), TBME (50 ml×2) and dried in vacuo to give the resin-bound phenyl carbamate (9.90 g, >100% recovery).

75 mg of the resin (75 mg, 0.0525 mmol) in anhydrous DCM (1 ml) was added n-butylamine (38.4 mg, 0.525 mmol). The reaction mixture was shaken at room temperature for 72 hours and then isolated by filtration. The resin was washed sequentially with DMF (1 ml), DCM (1 ml), DMF (1 ml), DCM (1 ml), MeOH (1 ml), DCM (1 ml), MeOH (1 ml), DCM (1 ml), MeOH (1 ml), TBME (1 ml×2) and dried in vacuo to give the resin-bound urea.

The cleavage was performed the following way:
1×0.5 ml 20% TFA/DCM 5 min.
4×0.2 ml 20% TFA/DCM 2 min.

The cleavage solutions were combined and then dried. The solid, was taken up in dimethylsulfoxyde and filtered to remove particular matter. The cleared DMSO solution was subjected to preparative reverse phase HPLC (C-18) using the instrument 1 (see above)

The product fractions were collected and those containing product pooled. Evaporation of the solvent then gave the dried N-butyl-N'-[6-(4-fluorophenyl)-1H-indazol-3-yl]urea as a dried powder HPLC r.t. (Method II): 1.43; [M+H]$^+$=327

By following the same procedure the following compounds have been synthesized.

By proceeding in the same way (example 8), 176 products were synthesized in parallel and coded in table XI, as formerly indicated; related HPLC retention time (Method II) and the experimentally found [M+H]+ are reported.

TABLE XI

| Entry | Compound | r.t. (min) | [M + H]+ |
|---|---|---|---|
| 1 | A28-M-C3 | 1.31 | 351.2 |
| 2 | A28-M-C21 | 1.39 | 339.2 |
| 3 | A28-M-C15 | 1.08 | 396.2 |
| 4 | A28-M-C13 | 1.09 | 391.2 |
| 5 | A28-M-C8 | 1.25 | 367.2 |
| 6 | A28-M-C9 | 1.44 | 387.2 |
| 7 | A28-M-C12 | 1.5 | 401.2 |
| 8 | A28-M-C22 | 1.32 | 325.2 |
| 9 | A28-M-C16 | 1.38 | 339.2 |
| 10 | A28-M-C7 | 1.33 | 337.2 |
| 11 | A28-M-C24 | 1.09 | 394.2 |
| 12 | A19-M-C3 | 1.32 | 351.2 |
| 13 | A19-M-C21 | 1.4 | 339.2 |
| 14 | A19-M-C15 | 1.09 | 396.2 |
| 15 | A19-M-C13 | 1.09 | 391.2 |
| 16 | A19-M-C5 | 1.02 | 352.2 |
| 17 | A19-M-C8 | 1.27 | 367.2 |
| 18 | A19-M-C9 | 1.45 | 387.2 |
| 19 | A19-M-C12 | 1.51 | 401.2 |
| 20 | A19-M-C16 | 1.39 | 339.2 |
| 21 | A19-M-C7 | 1.34 | 337.2 |
| 22 | A19-M-C24 | 1.11 | 394.2 |
| 23 | A39-M-C3 | 1.27 | 327.1 |
| 24 | A39-M-C15 | 1.05 | 372.1 |
| 25 | A39-M-C13 | 1.06 | 367.1 |
| 26 | A39-M-C5 | 0.98 | 328.1 |
| 27 | A39-M-C8 | 1.22 | 343.1 |
| 28 | A39-M-C9 | 1.44 | 363.1 |
| 29 | A39-M-C12 | 1.48 | 377.1 |
| 30 | A39-M-C22 | 1.29 | 301.1 |
| 31 | A39-M-C16 | 1.35 | 315.1 |
| 32 | A39-M-C7 | 1.3 | 313.1 |
| 33 | A39-M-C24 | 1.07 | 370.2 |
| 34 | A22-M-C3 | 1.39 | 335.2 |
| 35 | A22-M-C21 | 1.47 | 323.2 |
| 36 | A22-M-C15 | 1.15 | 380.2 |
| 37 | A22-M-C13 | 1.17 | 375.2 |
| 38 | A22-M-C5 | 1.08 | 336.2 |
| 39 | A22-M-C12 | 1.59 | 385.2 |
| 40 | A22-M-C22 | 1.4 | 309.2 |
| 41 | A22-M-C16 | 1.47 | 323.2 |
| 42 | A22-M-C7 | 1.42 | 321.2 |
| 43 | A22-M-C24 | 1.17 | 378.2 |
| 44 | A37-M-C21 | 1.39 | 339.2 |
| 45 | A37-M-C15 | 1.08 | 396.2 |
| 46 | A37-M-C13 | 1.09 | 391.2 |
| 47 | A37-M-C5 | 1.02 | 352.2 |
| 48 | A37-M-C8 | 1.26 | 367.2 |
| 49 | A37-M-C9 | 1.45 | 387.2 |
| 50 | A37-M-C12 | 1.5 | 401.2 |
| 51 | A37-M-C22 | 1.32 | 325.2 |
| 52 | A37-M-C16 | 1.39 | 339.2 |
| 53 | A37-M-C7 | 1.34 | 337.2 |
| 54 | A37-M-C24 | 1.11 | 394.2 |
| 55 | A15-M-C3 | 1.39 | 335.2 |
| 56 | A15-M-C21 | 1.48 | 323.2 |
| 57 | A15-M-C15 | 1.16 | 380.2 |
| 58 | A15-M-C13 | 1.17 | 375.2 |
| 59 | A15-M-C5 | 1.09 | 336.2 |
| 60 | A15-M-C9 | 1.53 | 371.2 |
| 61 | A15-M-C22 | 1.41 | 309.2 |
| 62 | A15-M-C16 | 1.47 | 323.2 |
| 63 | A15-M-C24 | 1.17 | 378.2 |
| 64 | A32-M-C3 | 1.11 | 378.2 |
| 65 | A32-M-C21 | 1.19 | 366.2 |
| 66 | A32-M-C15 | 0.9 | 423.2 |
| 67 | A32-M-C13 | 0.92 | 418.2 |
| 68 | A32-M-C8 | 1.05 | 394.2 |
| 69 | A32-M-C9 | 1.25 | 414.2 |
| 70 | A32-M-C12 | 1.32 | 428.2 |
| 71 | A32-M-C22 | 1.11 | 352.2 |
| 72 | A32-M-C7 | 1.13 | 364.2 |
| 73 | A32-M-C24 | 0.92 | 421.2 |
| 74 | A28-M-C19 | 1.39 | 365.2 |
| 75 | A28-M-C25 | 1.01 | 366.2 |
| 76 | A28-M-C33 | 1.16 | 408.2 |
| 77 | A28-M-C27 | 1.06 | 340.2 |
| 78 | A28-M-C28 | 1.04 | 326.2 |
| 79 | A28-M-C35 | 1.07 | 367.2 |
| 80 | A28-M-C36 | 1.12 | 341.2 |
| 81 | A28-M-C11 | 1.08 | 388.2 |
| 82 | A28-M-C14 | 1.12 | 394.2 |
| 83 | A28-M-C2 | 1.21 | 337.2 |
| 84 | A28-M-C32 | 1.09 | 368.2 |
| 85 | A28-M-C30 | 1.09 | 394.2 |
| 86 | A19-M-C19 | 1.41 | 365.2 |
| 87 | A19-M-C25 | 1.03 | 366.2 |
| 88 | A19-M-C33 | 1.17 | 408.2 |
| 89 | A19-M-C35 | 1.11 | 367.2 |
| 90 | A19-M-C36 | 1.15 | 341.2 |
| 91 | A19-M-C11 | 1.12 | 388.2 |
| 92 | A19-M-C14 | 1.15 | 394.2 |
| 93 | A19-M-C2 | 1.23 | 337.2 |
| 94 | A19-M-C32 | 1.13 | 368.2 |
| 95 | A19-M-C30 | 1.12 | 394.2 |
| 96 | A39-M-C19 | 1.37 | 341.1 |
| 97 | A39-M-C25 | 1.01 | 342.1 |
| 98 | A39-M-C33 | 1.15 | 384.1 |
| 99 | A39-M-C27 | 1.06 | 316.1 |
| 100 | A39-M-C28 | 1.04 | 302.1 |
| 101 | A39-M-C35 | 1.07 | 343.1 |
| 102 | A39-M-C36 | 1.11 | 317.1 |
| 103 | A39-M-C11 | 1.08 | 364.1 |
| 104 | A39-M-C14 | 1.12 | 370.2 |
| 105 | A39-M-C2 | 1.19 | 313.1 |
| 106 | A39-M-C32 | 1.09 | 344.1 |
| 107 | A39-M-C30 | 1.08 | 370.1 |
| 108 | A22-M-C19 | 1.48 | 349.2 |
| 109 | A22-M-C25 | 1.12 | 350.2 |
| 110 | A22-M-C33 | 1.25 | 392.2 |
| 111 | A22-M-C27 | 1.16 | 324.2 |
| 112 | A22-M-C28 | 1.14 | 310.2 |
| 113 | A22-M-C35 | 1.18 | 351.2 |
| 114 | A22-M-C36 | 1.23 | 325.2 |
| 115 | A22-M-C11 | 1.18 | 372.2 |
| 116 | A22-M-C14 | 1.23 | 378.2 |
| 117 | A22-M-C2 | 1.3 | 321.2 |
| 118 | A22-M-C32 | 1.2 | 352.2 |
| 119 | A22-M-C30 | 1.19 | 378.2 |
| 120 | A37-M-C19 | 1.4 | 365.2 |
| 121 | A37-M-C25 | 1.05 | 366.2 |
| 122 | A37-M-C33 | 1.18 | 408.2 |
| 123 | A37-M-C27 | 1.1 | 340.2 |
| 124 | A37-M-C28 | 1.08 | 326.2 |
| 125 | A37-M-C35 | 1.11 | 367.2 |
| 126 | A37-M-C36 | 1.15 | 341.2 |
| 127 | A37-M-C11 | 1.12 | 388.2 |
| 128 | A37-M-C14 | 1.15 | 394.2 |
| 129 | A37-M-C2 | 1.22 | 337.2 |
| 130 | A37-M-C32 | 1.12 | 368.2 |
| 131 | A37-M-C30 | 1.11 | 394.2 |

TABLE XI-continued

| Entry | Compound | r.t. (min) | [M + H]+ |
|---|---|---|---|
| 132 | A38-M-C28 | 1.04 | 302.1 |
| 133 | A15-M-C19 | 1.48 | 349.2 |
| 134 | A15-M-C25 | 1.12 | 350.2 |
| 135 | A15-M-C33 | 1.25 | 392.2 |
| 136 | A15-M-C27 | 1.16 | 324.2 |
| 137 | A15-M-C28 | 1.14 | 310.2 |
| 138 | A15-M-C35 | 1.18 | 351.2 |
| 139 | A15-M-C36 | 1.22 | 325.2 |
| 140 | A15-M-C11 | 1.19 | 372.2 |
| 141 | A15-M-C14 | 1.23 | 378.2 |
| 142 | A15-M-C2 | 1.3 | 321.2 |
| 143 | A15-M-C32 | 1.19 | 352.2 |
| 144 | A15-M-C30 | 1.18 | 378.2 |
| 145 | A32-M-C19 | 1.21 | 392.2 |
| 146 | A32-M-C33 | 1 | 435.2 |
| 147 | A32-M-C27 | 0.91 | 367.2 |
| 148 | A32-M-C28 | 0.9 | 353.2 |
| 149 | A32-M-C35 | 0.93 | 394.2 |
| 150 | A32-M-C36 | 0.96 | 368.2 |
| 151 | A32-M-C11 | 0.93 | 415.2 |
| 152 | A32-M-C14 | 0.96 | 421.2 |
| 153 | A32-M-C32 | 0.94 | 395.2 |
| 154 | A28-M-C26 | 1.23 | 355.2 |
| 155 | A28-M-C20 | 1.39 | 365.2 |
| 156 | A28-M-C4 | 1.07 | 429.2 |
| 157 | A28-M-C1 | 1.53 | 441.2 |
| 158 | A28-M-C23 | 1.13 | 394.2 |
| 159 | A28-M-C31 | 1.19 | 446.2 |
| 160 | A28-M-C10 | 1.39 | 393.1 |
| 161 | A28-M-C34 | 1.1 | 395.2 |
| 162 | A28-M-C6 | 1.27 | 369.1 |
| 163 | A19-M-C26 | 1.25 | 355.2 |
| 164 | A19-M-C20 | 1.4 | 365.2 |
| 165 | A19-M-C17 | 1.45 | 353.2 |
| 166 | A19-M-C4 | 1.09 | 429.2 |
| 167 | A19-M-C1 | 1.56 | 441.2 |
| 168 | A19-M-C29 | 1.26 | 450.2 |
| 169 | A19-M-C18 | 1.47 | 379.2 |
| 170 | A19-M-C23 | 1.14 | 394.2 |
| 171 | A19-M-C31 | 1.22 | 446.2 |
| 172 | A19-M-C10 | 1.42 | 393.1 |
| 173 | A19-M-C34 | 1.12 | 395.2 |
| 174 | A19-M-C6 | 1.29 | 369.1 |
| 175 | A39-M-C26 | 1.2 | 331.1 |
| 176 | A39-M-C20 | 1.34 | 341.1 |

EXAMPLE 9

N-(6-bromo-1H-indazol-3-yl)-3-chloropropane-1-sulfonamide

The reaction was performed in a "Miniblock" reactor (Bohdan) charged with Trityl-resin bearing 6-bromo-1H-indazol-3-amine. To the resin (12.5 mg) bearing 6-bromo-1H-indazol-3-amine (1.2 mmol/g) was added a 3-chloropropanesulfonyl chloride (0.2 Mol) in pyridine (2 ml). The reaction mixture was shaken for 24 hours at 55° C.

The resin was washed as follows:
5×1 ml DMF

The resulting imids of 6-bromo-1H-indazol-3-amine could be either isolated or converted to amides using terabutylammonium fluoride (0.5 M) in THF (16 hours).

The resins were then washed
5×10% acetic acid in DCM
5× a) 1 ml DMF; b) 1 ml $H_2O$
5× a) 1 ml MeOH; b) 1 ml DCM
5× a) 1 ml DCM The cleavage was performed in the following way:
1×0.5 ml 20% TFA/DCM 5 min.
4×0.2 ml 20% TFA/DCM 2 min.

The cleavage solutions were combined and then dried.
HPLC r.t. (Method I) 5.56; $[M-H]^+=354.1$ By working in an analogous way, starting from 6-bromo-1H-indazol-3-amine the following products were cleaved from the resin.

N-(6-bromo-1H-indazol-3-yl)-2,2,2-trifluoroethanesulfonamide
HPLC r.t. (Method I) 5.25; $[M+H]^+=359.89$; $[M-H]^-=357.98$ N-(6-bromo-1H-indazol-3-yl)-1-phenylmethanesulfonamide
HPLC r.t. (Method I) 6.0; $[M+H]^+=367.93$; $[M-H]^-=366.04$ N-(6-bromo-1H-indazol-3-yl)-1-[(1R,4S)-7,7-dimethyl-2-oxobicyclo[2.2.1]hept-1-yl]methanesulfonamide
HPLC r.t. (Method I) 6.12; $[M+H]^+=428.02$; $[M-H]^-=426.13$ 4-acetyl-N-(6-bromo-1H-indazol-3-yl)benzenesulfonamide
HPLC r.t. (Method I) 6.12; $[M+H]^+=395$, 436 $(M+1+MeCN)^+$

What is claimed is:

1. A compound of formula (I)

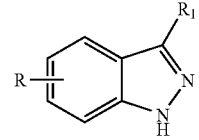

wherein

R is, in position 5 or 6 of the indazole ring, a halogen atom or an optionally substituted group selected from straight or branched $C_2$-$C_6$alkenyl, $C_2$-$C_6$alkynyl, or aryl which is selected from phenyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, pyran, pyrroline, or pyrazoline;

$R_1$ is an optionally substituted group selected from —NHCOR';

$R_a$ and $R_b$ are, each independently, hydrogen or a straight or branched $C_1$-$C_6$alkyl group;

R' and R" are, each independently, hydrogen or an optionally substituted group selected from straight or branched $C_1$-$C_6$ alkyl, $C_2$-$C_6$ alkenyl or alkynyl, $C_3$-$C_6$ cycloalkyl or cycloalkyl $C_1$-$C_6$ alkyl, aryl or aryl $C_1$-$C_6$ alkyl wherein aryl is as above defined, or a 5or 6 membered heterocyclyl or heterocyclyl $C_1$-$C_6$ alkyl; or, when taken together with the nitrogen atom to which they are attached, R' and R" may form an optionally substituted 4 to 7 membered heterocycle, optionally containing an additional heteroatom selected from S, O or N; or isomers, tautomers, and pharmaceutically acceptable salts thereof.

2. A compound of formula (I) according to claim 1 wherein R is an optionally substituted aryl group and $R_1$ is a group —NHCOR', wherein R" is as defined in claim 1.

3. A library of two or more compounds of formula (I)

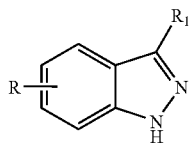

wherein
R is, in position 5 or 6 of the indazole ring, a halogen atom or an optionally substituted group selected from straight or branched $C_2$-$C_6$ alkenyl, $C_2$-$C_6$ alkynyl, or aryl which is selected from phenyl, indanyl, biphenyl, α- or β-naphthyl, fluorenyl, 9,10-dihydroanthracenyl, pyridyl, pyrazinyl, pyrimidinyl, pyridazinyl, indolyl, imidazolyl, imidazopyridyl, 1,2-methylenedioxyphenyl, thiazolyl, isothiazolyl, pyrrolyl, pyrrolyl-phenyl, furyl, phenyl-furyl, benzotetrahydrofuranyl, oxazolyl, isoxazolyl, pyrazolyl, chromenyl, thienyl, benzothienyl, isoindolinyl, benzoimidazolyl, isoindolinyl-phenyl, quinolinyl, isoquinolinyl, 2,6-diphenyl-pyridyl, quinoxalinyl, pyrazinyl, phenyl-quinolinyl, benzofurazanyl, 1,2,3-triazolyl, 1-phenyl-1,2,3-triazolyl, pyran, pyrroline, or pyrazoline;

$R_1$ is an optionally substituted group selected from —NH-COR';

$R_a$ and $R_b$ are, each independently, hydrogen or a straight or branched $C_1$-$C_6$ alkyl group;

R' and R'' are, each independently, hydrogen or an optionally substituted group selected from straight or branched $C_1$-$C_6$ alkyl, $C_2$-$C_6$ alkenyl or alkynyl, $C_3$-$C_6$ cycloalkyl or cycloalkyl $C_1$-$C_6$ alkyl, aryl or aryl $C_1$-$C_6$ alkyl wherein aryl is as above defined, or a 5 or 6 membered heterocyclyl or heterocyclyl $C_1$-$C_6$ alkyl; or, when taken together with the nitrogen atom to which they are attached, R' and R'' may form an optionally substituted 4 to 7 membered heterocycle, optionally containing an additional heteroatom selected from S, O or N;

or isomers, tautomers, and pharmaceutically acceptable salts thereof.

4. A pharmaceutical composition comprising an effective amount of a compound of formula (I) according to claim 1 and, at least, one pharmaceutically acceptable excipient, carrier or diluent.

5. A pharmaceutical composition according to claim 4 further comprising one or more chemotherapeutic agents.

6. A compound of formula (I) according to claim 1, optionally in the form of a pharmaceutically acceptable salt, is selected from the group consisting of:
N-[6-(3-methylphenyl)-1H-indazol-3-yl]cyclopropanecarboxamide;
2-methyl-N-[6-(3-methylphenyl)-1H-indazol-3-yl]propanamide;
N-[6-(3-methylphenyl)-1H-indazol-3-yl]-2-phenoxypropanamide;
N-[6-(3-methylphenyl)-1H-indazol-3-yl]cyclopentanecarboxamide;
N-[6-(3-methylphenyl)-1H-indazol-3-yl]cyclobutanecarboxamide;
N-{6-[3-(acetylamino)phenyl]-1H-indazol-3-yl}-3-cyclopentylpropanamide;
N-{6-[3-(acetylamino)phenyl]-1H-indazol-3-yl}butanamide;
N-{6-[3-(acetyhtmino)phenyl]-1H-indazol-3-yl}-2-phenoxypropanamide;
N-[6-(4-acetylphenyl)-1H-indazol-3-yl]-3-cyclopentylpropanainide;
N-[6-(4-acetylphenyl)-1H-indazol-3-yl]-2-(4-methoxyphenyl)acetamide;
N-[6-(4-acetylphenyl)-1H-indazol-3-yl]butanamide;
N-[6-(4-acetylphenyl)-1H-indazol-3-yl]cyclopropanecarboxamide;
N-[6-(4-acetylphenyl)-1H-indazol-3-yl]-2-methylpropanamide;
N-[6-(4-acetylphenyl)-1H-indazol-3-yl]-2-phenoxypropanamide;
N-[6-(4-acetylphenyl)-1H-indazol-3-yl]cyclopentanecarboxamide;
N-[6-(4-acetylphenyl)-1H-indazol-3-yl]cyclobutanecarboxamide;
N-[6-(3-chloro-4-fluorophenyl)-1H-indazol-3-yl]cyclopropanecarboxarnide;
N-[6-(3-chloro-4-fluorophenyl)-1H-indazol-3-yl]-2-phenoxypropanamide;
N-[6-(3-chlorophenyl)-1H-indazol-3-yl]cyclopropanecarboxamide;
N-[6-(3-chlorophenyl)-1H-indazol-3-yl]-2-methylpropanamide;
N-[6-(3-chiorophenyl)-1H-indazol-3-yl]-2-phenoxypropanamide;
N-[6-(3-chlorophenyl)-1H-indazol-3-yl]-2-methoxyacetamide;
N-[6-(3-chlorophenyl)-1H-indazol-3-yl]cyclobutanecarboxamide;
N-[6-(3,4-dichlorophenyl)-1H-indazol-3-yl]-2-phenoxypropanamide;
N-[6-(3,4-dichlorophenyl)-1H-indazol-3-yl]-2-methoxyacetamide;
3-cyclopentyl-N-[6-(3-fluorophenyl)-1H-indazol-3-yl]propanamide;
N-[6-(3-fluorophenyl)-1H-indazol-3-yl]cyclopropanecarboxamide;
N-[6-(3-fluorophenyl)-1H-indazol-3-yl]-2-methylpropanamide;
N-[6-(3-fluorophenyl)-1H-indazol-3-yl]-2-phenoxypropanamide;
N-[6-(3-fluorophenyl)-1H-indazol-3-yl]cyclopentanecarboxamide;
N-[6-(3-fluorophenyl)-1H-indazol-3-yl]-2-methoxyacetamide;
N-[6-(3-fluorophenyl)-1H-indazol-3-yl]cyclobutanecarboxamide;
3-cyclopentyl-N-{6-[4-(trifluoromethoxy)phenyl]-1H-indazol-3-yl}propanamide;
N-{6-[4-(trifluoromethoxy)phenyl]-1H-indazol-3-yl}butanamide;
N-{6-[4-(trifluoromethoxy)phenyl]-1H-indazol-3-yl}cyclopropanecarboxamide;
2-methyl-N-{6-[4-(trifluoromethoxy)phenyl]-1H-indazol-3-yl}propanamide;
2-phenoxy-N-{6-[4-(trifluoromethoxy)phenyl]-1H-indazol-3-yl}propanamide;
N-{6-[4-(trifluoromethoxy)phenyl]-1H-indazol-3-yl}cyclobutanecarboxamide;
2-(3-methoxyphenyl)-N-[6-(3-methylphenyl)-1H-indazol-3-yl]acetamide;
N-[6-(3-methylphenyl)-1H-indazol-3-yl]-2,2-diphenylacetamide;
2-(benzyloxy)-N-[6-(3-methylphenyl)-1H-indazol-3-yl]acetamide;

N-[6-(3-methylphenyl)-1H-indazol-3-yl]furan-2-carboxamide;
2-cyclopentyl-N-[6-(3-methylphenyl)-1H-indazol-3-yl]acetamide;
2-methoxy-N-[6-(3-methylphenyl)-1H-indazol-3-yl]benzamide;
3-fluoro-N-[6-(3-methylphenyl)-1H-indazol-3-yl]benzamide;
3-chloro-N-[6-(3-methylphenyl)-1H-indazol-3-yl]benzamide;
3,4,5-trimethoxy-N-[6-(3-methylphenyl)-1H-indazol-3-yl]benzamide;
3,5-dichloro-N-[6-(3-methylphenyl)-1H-indazol-3-yl]benzamide;
2,4-dimethoxy-N-[6-(3-methylphenyl)-1H-indazol-3-yl]benzamide;
2,3,6-trifluoro-N-[6-(3-methylphenyl)-1H-indazol-3-yl]benzamide;
N-{6-[3-(acetylamino)phenyl]-1H-indazol-3-yl}-2-(3-methoxyphenyl)acetamide;
N-{6-[3-(acetylamino)phenyl]-1H-indazol-3-yl}-2,2-diphenylacetamide;
N-{6-[3-(acetylamino)phenyl]-1H-indazol-3-yl}-3,4,5-trimethoxybenzamide;
N-[6-(4-acetylphenyl)-1H-indazol-3-yl]-2,2diphenylacetamide;
N-[6-(4-acetylphenyl)-1H-indazol-3-yl]-2-(benzyloxy)acetamide;
N-[6-(4-acetylphenyl)-1H-indazol-3-yl]-3-chlorobenzamide;
N-[6-(4-acetylphenyl)-1H-indazol-3-yl]-3,4,5-trimethoxybenzamide;
N-[6-(4-acetylphenyl)-1H-indazol-3-yl]-2,3,6-trifluorobenzamide;
2-(benzyloxy)-N-[6-(3-chloro-4-fluorophenyl)-1H-indazol-3-yl]acetamide;
2-(benzyloxy)-N-[6-(3-chlorophenyl)-1H-indazol -3-yl]acetamide;
N-[6-(3-chlorophenyl)-1H-indazol-3-yl]-2-methoxybenzamide;
N-[6-(3-chiorophenyl)-1H-indazol-3-yl]-3-fluorobenzamide;
N-[6-(3-chiorophenyl)-1H-indazol-3-yl]-3,4,5-trimethoxybenzamide;
3,5-dichloro-N-[6-(3-chlorophenyl)-1H-indazol-3-yl]benzamide;
N-[6-(3-chlorophenyl)-1H-indazol-3-yl]-2,4-dimethoxybenzamide;
N-[6-(3-chlorophenyl)-1H-indazol-3-yl]-2,3,6-trifluorobenzamide;
N-[6-(3,4-dichlorophenyl)-1H-indazol-3-yl]-3-fluorobenzamide;
N-[6-(3,4-dichlorophenyl)-1H-indazol-3-yl]-3,4,5-trimethoxybenzamide;
N-[6-(3-fluorophenyl)-1H-indazol-3-yl]-2,2-diphenylacetamide;
2-(benzyloxy)-N-[6-(3-fluorophenyl)-1H-indazol-3-yl]acetamide;
2-cyclopentyl-N-[6-(3-fluorophenyl)-1H-indazol-3-yl]acetamide
N-[6-(3-fluorophenyl)-1H-indazol-3-yl]-2-methoxybenzamide;
N-[6-(3-fluorophenyl)-1H-indazol-3-yl]-3,4,5-trimethoxybenzamide;
3,5-dichloro-N-[6-(3-fluorophenyl)-1H-indazol-3-yl]benzamide;
N-[6-(3-fluorophenyl)-1H-indazol-3-yl]-2,4-dimethoxybenzamide;
2,3,6-trifluoro-N-[6-(3-fluorophenyl)-1H-indazol-3-yl]benzamide;
2-(benzyloxy)-N-{6-[4-(trifluoromethoxy)phenyl]-1H-indazol-3-yl}acetamide;
2-methoxy-N-{6-[4-(trifluoromethoxy)phenyl]-1H-indazol-3-yl}benzamide;
3,4,5-trimethoxy-N-{6-[4-(trifluoromethoxy)phenyl]-1H-indazol-3-yl}benzamide;
2,3,6-trifluoro-N-{6-[4-(trifluoromethoxy)phenyl]-1H-indazol-3-yl}benzamide;
3cyclopentyl-N-[6-(2-fluorophenyl)-1H-indazol-3-yl]propanamide;
N-[6-(3-chloro-4-fluorophenyl)-1H-indazol-3-yl]butanamide;
N-[6-(3-chloro-4-fluorophenyl)-1H-indazol-3-yl]-2-methylpropanamide;
N-[6-(3-chloro-4-fluorophenyl)-1H-indazol-3-yl]-2-methoxyacetamide;
N-[6-(3-chlorophenyl)-1H-indazol-3-yl]butanamide;
N-[6-(3,4-dichlorophenyl)-1H-indazol-3-yl]-2-methylpropanamide;
N-{6-[4-(trifluoromethoxy)phenyl]-1H-indazol-3-yl}cyclopentanecarboxamide;
N-[6-(4-acetylphenyl)-1H-indazol-3-yl]furan-2-carboxamide;
N-[6-(2-fluorophenyl)-1H-indazol-3-yl]cyclopropanecarboxamide;
N-[6-(2-fluorophenyl)-1H-indazol-3-yl]-2-phenoxypropanamide
N-[6-(2-fluorophenyl)-1H-indazol-3-yl]cyclopentanecarboxamide
N-[6-(2-fluorophenyl)-1H-indazol-3-yl]cyclobutanecarboxamide;
3-cyclopentyl-N-[6-(2-methylphenyl)-1-indazol-3-yl]propanamide;
N-[6-(2-methylphenyl)-1H-indazol-3-yl]cyclopentanecarboxamide;
2-methoxy-N-[6-(2-methylphenyl)-1H-indazol-3-yl]acetamide;
N-[6-(2-methylphenyl)-1H-indazol-3-yl]cyclobutanecarboxamide;
N-[6-(3-acetylphenyl)-1H-indazol-3-yl]-3-cyclopentylpropanamide
N-[6-(3-acetylphenyl)-1H-indazol-3-yl]cyclopropanecarboxamide
N-[6-(3-acetylphenyl)-1H-indazol-3-yl]-2-phenoxypropanamide
N-[6-(3-acetylphenyl)-1H-indazol-3-yl]cyclopentanecarboxamide
N-[6-(3-acetylphenyl)-1H-indazol-3-yl]cyclobutanecarboxamide
N-[6-(4-cyanophenyl)-1H-indazol-3-yl]-3-cyclopentylpropanamide;
N-[6-(4-cyanophenyl)-1H-indazol-3-yl]-2-phenoxypropanamide;
N-[6-(4-cyanophenyl)-1H-indazol-3-yl]cyclopentanecarboxamide;
N-[6-(4-cyanophenyl)-1H-indazol-3-yl]cyclobutanecarboxamide;
N-[6-(2,4-difluorophenyl)-1H-indazol-3-yl]acetamide;
N-[6-(2,4-difluorophenyl)-1H-indazol-3-yl]cyclopropanecarboxamide;
N-[6-(2,4-difluorophenyl)-1H-indazol-3-yl]-2-methylpropanamide;

N-[6-(2,4-difluorophenyl)-1H-indazol-3-yl]-2-phenoxypropanamide;
N-[6-(2,4-difluorophenyl)-1H-indazol-3-yl]-2-methoxyacetamide;
N-[6-(2,4-difluorophenyl)-1H-indazol-3-yl]cyclobutanecarboxamide;
3-cyclopentyl-N-[6-(2,4-dimethoxyphenyl)-1H-indazol-3-yl]propanamide;
N-[6-(2,4-dimethoxyphenyl)-1H-indazol-3-yl]cyclopropanecarboxamide;
N-[6-(2,4-dimethoxyphenyl)-1H-indazol-3-yl]-2-methylpropanamide;
N-[6-(2,4-dimethoxyphenyl)-1H-indazol-3-yl]-2-phenoxypropanamide;
N-[6-(2,4-dimethoxyphenyl)-1H-indazol-3-yl]cyclopentanecarboxamide;
N-[6-(2,4-dimethoxyphenyl)-1H-indazol-3-yl]-2-methoxyacetamide;
N-[6-(2,4-dimethoxyphenyl) 1H-indazol-3-yl]cyclobutanecarboxamide;
N-[6-(3-cyanophenyl)-1H-indazol-3-yl]-2-methylpropanamide;
N-[6-(3-cyanophenyl)-1H-indazol-3-yl]cyclobutanecarboxamide;
N-[6-(2-fluorophenyl)-1H-indazol-3-yl]-2-(3-methoxyphenyl)acetamide;
N-[6-(2-fluorophenyl)-1H-indazol-3-yl]-2,2-diphenylacetamide;
2-(benzyloxy)-N-[6-(2-fluorophenyl)-1H-indazol-3-yl]acetamide;
N-[6-(2-fluorophenyl)-1H-indazol-3-yl]furan-2-carboxamide;
N-[6-(2-fluorophenyl)-1H-indazol-3-yl]-2-methoxybenzamide;
3-fluoro-N-[6-(2-fluorophenyl)-1H-indazol-3-yl]benzamide;
3-chloro-N-[6-(2-fluorophenyl)-1H-indazol-3-yl]benzamide;
N-[6-(2-fluorophenyl)-1H-indazol-3-yl]-3,4,5-trimethoxybenzamide
N-[6-(2-fluorophenyl)-1H-indazol-3-yl]-2,4-dimethoxybenzamide;
2,3,6-trifluoro-N-[6-(2-fluorophenyl)-1H-indazol-3-yl]benzamide;
N-[6-(2-methylphenyl)-1H-indazol-3-yl]-2,2-diphenylacetamide;
2-(benzyloxy)-N-[6-(2-methylphenyl)-1H-indazol-3-yl]acetamide;
N-[6-(2-methylphenyl)-1H-indazol-3-yl]furan-2-carboxamide;
2-cyclopentyl-N-[6-(2-methylphenyl)-1H-indazol-3-yl]acetamide;
2-methoxy-N-[6-(2-methylphenyl)-1H-indazol-3-yl]benzamide;
3-fluoro-N-[6-(2-methylphenyl)-1H-indazol-3-yl]benzamide;
3-chloro-N-[6-(2-methylphenyl)-1H-indazol-3-yl]benzamide;
3,4,5-trimethoxy-N-[6-(2-methylphenyl)-1H-indazol-3-yl]benzamide;
3,5-dichloro-N-[6-(2-methylphenyl)-1H-indazol-3-yl]benzamide;
2,4-dimethoxy-N-[6-(2-methylphenyl)-1H-indazol-3-yl]benzamide;
2,3,6-trifluoro-N-[6-(2-methylphenyl)-1H-indazol-3-yl]benzamide;
N-[6-(3-acetylphenyl)-1H-indazol-3-yl]-2-(3-methoxyphenyl)acetamide
N-[6-(3-acetylphenyl)-1H-indazol-3-yl]-2-(benzyloxy)acetamide
N-[6-(3-acetylphenyl)-1H-indazol-3-yl]furan-2-carboxamide;
N-[6-(3-acetylphenyl)-1H-indazol-3-yl]-2-cyclopentylacetamide;
N-[6-(3-acetylphenyl)-1H-indazol-3-yl]-2-methoxybenzamide
N-[6-(3-acetylphenyl)-1H-indazol-3-yl]-3-fluorobenzamide;
N-[6-(3-acetylphenyl)-1H-indazol-3-yl]-3-chlorobenzamide;
N-[6-(3-acetylphenyl)-1H-indazol-3-yl]-3,4,5-trimethoxybenzamide;
N-[6-(3-acetylphenyl)-1H-indazol-3-yl]-3,5-dichlorobenzamide;
N-[6-(3-acetylphenyl)-1H-indazol-3-yl]-2,4-dimethoxybenzamide
N-[6-(3-acetylphenyl)-1H-indazol-3-yl]-2,3,6-trifluorobenzamide;
N-[6-(4-cyanophenyl)-1H-indazol-3-yl]-2,2-diphenylacetamide
2-(benzyloxy)-N-[6-(4-cyanophenyl)-1H-indazol-3-yl]acetamide;
N-[6-(4-cyanophenyl)-1H-indazol-3-yl]furan-2-carboxamide
N-[6-(4-cyanophenyl)-1H-indazol-3-yl]-3-fluorobenzamide;
N-[6-(4-cyanophenyl) 1H-indazol-3-yl]-2,3,6-trifluorobenzamide;
2-(benzyloxy)-N-[6-(2,4-difluorophenyl) 1H-indazol-3-yl]acetamide;
N-[6-(2,4-difluorophenyl)-1H-indazol-3-yl]-2-methoxybenzamide
N-[6-(2,4-difluorophenyl)-1H-indazol-3-yl]-3-fluorobenzamide;
N-[6-(2,4-difluorophenyl)-1H-indazol-3-yl]-3,4,5-trimethoxybenzamide
N-[6-(2,4-difluorophenyl)-1H-indazol-3-yl]-2,3,6-trifluorobenzamide;
N-[6-(2,4-dimethoxyphenyl)-1H-indazol-3-yl]-2-(3-methoxyphenyl)acetamide;
N-[6-(2,4-dimethoxyphenyl)-1H-indazol-3-yl]-2,2-diphenylacetamide
2-(benzyloxy)-N-[6-(2,4-dimethoxyphenyl)-1H-indazol-3-yl]acetamide;
N-[6-(2,4-dimethoxyphenyl)-1H-indazol-3-yl]furan-2-carboxamide;
2-cyclopentyl-N-[6-(2,4-dimethoxyphenyl)-1H-indazol-3-yl]acetamide;
N-[6-(2,4-dimethoxyphenyl)-1H-indazol-3-yl]-2-methoxybenzamide;
N-[6-(2,4-dimethoxyphenyl)-1H-indazol-3-yl]-3-fluorobenzamide;
3-chloro-N-[6-(2,4-dimethoxyphenyl)-1H-indazol-3-yl]benzamide;
N-[6-(2,4-dimethoxyphenyl)-1H-indazol-3-yl]-3,4,5-trimethoxybenzamide;
N-[6-(2,4-dimethoxyphenyl)-1H-indazol-3-yl]-2,4-dimethoxybenzamide;
N-[6-(2,4-dimethoxyphenyl)-1H-indazol-3-yl]-2,3,6-trifluorobenzamide;
N-[6-(3-cyanophenyl)-1H-indazol-3-yl]-2,2-diphenylacetamide;

2-(benzyloxy)-N-[6-(3-cyanophenyl)-1H-indazol-3-yl] acetamide;
N-[6(3-cyanophenyl)-1H-indazol-3-yl]-2methoxybenzamide;
N-[6-(3,5-dimethylphenyl)-1H-indazol-3-yl]-2-methoxyacetamide;
N-[6-(3,5-dimethylphenyl)-1H -indazol-3-yl]cyclobutanecarboxamide;
3-cyclopentyl-N-[6-(3-ethoxyphenyl)-1H-indazol-3-yl] propanamide;
N-[6-(3-ethoxyphenyl)-1H-indazol-3-yl]cyclopropanecarboxamide;
N-[6-(3-ethoxyphenyl)-1H-indazol-3-yl]-2-methylpropanamide;
N-[6-(3-ethoxyphenyl)-1H-indazol-3-yl]-2-phenoxypropanamide;
N-[6-(3-ethoxyphenyl)-1H-indazol-3-yl]cyclopentanecarboxamide;
N-[6-(3-ethoxyphenyl)-1H-indazol-3-yl]-2-methoxyacetamide;
N-[6-(3-ethoxyphenyl)-1H-indazol-3-yl]cyclobutanecarboxamide;
N-[6-(2-ethoxyphenyl) 1H-indazol-3-yl]acetamide;
3-cyclopentyl-N-[6(2-ethoxyphenyl)-1H-indazol-3-yl] propanamide;
N-[6-(2-ethoxyphenyl)-1H-indazol-3-yl]-2-phenoxypropanamide;
N-[6-(2-ethoxyphenyl)-1H-indazol-3-yl]cyclopentanecarboxamide;
N-[6-(2-ethoxyphenyl)-1H-indazol-3-yl]cyclobutanecarboxamide ;
3-cyclopentyl-N-[6-(2,6-dimethylphenyl)-1H-indazol-3-yl]propanamide
N-[6-(2,6-dimethylphenyl) 1H-indazol-3-yl]-2-(4-methoxyphenyl)acetamide;
N-[6-(2,6-dimethylphenyl)-1H-indazol-3-yl]-2-methylpropanamide;
N-[6-(2,6-dimethylphenyl)-1H-indazol-3-yl]-2-phenoxypropanamide;
N-[6-(2,6-dimethylphenyl)-1H-indazol-3-yl]cyclopentanecarboxamide;
N-[6-(2,6-dimethylphenyl)-1H-indazol-3-yl]cyclobutanecarboxamide;
N-[6-(3,4-dimethylphenyl)-1H-indazol-3-yl]-2-phenylacetamide;
N-[6-(3,4-dimethylphenyl)-1H-indazol-3-yl]acetamide;
3-cyclopentyl-N-[6-(3,4-dimethylphenyl)-1H-indazol-3-yl]propanamide;
N-[6-(3,4-dimethylphenyl)-1H-indazol-3-yl]cyclopropanecarboxamide;
N-[6-(3,4-dimethylphenyl)-1H-indazol-3-yl]-2-methylpropanamide;
N-[6-(3,4-dimethylphenyl)-1H-indazol-3-yl]-2-phenoxypropanamide;
N-{6-[4-(propan-2-yl)phenyl]-1H-indazol-3-yl}cyclopropanecarboxamide;
2-methyl-N-{6-[4-(propan-2-yl)phenyl]-1H-indazol-3-yl}propanamide;
2-phenoxy-N-{6-[4-(propan-2-yl)phenyl]-1H-indazol-3-yl}propanamide;
2-methoxy-N-{6-[4-(propan-2-yl)phenyl]-1H-indazol-1-3-yl}acetamide;
N-{6-[4-(propan-2-yl)phenyl]-1H-indazol-3-yl}cyclobutanecarboxamide;
N-{6-[4-(dimethylamino)phenyl]-1H-indazol-3-yl}-2-phenylacetamide;
N-{6-[4-(dimethylamino)phenyl]-1H-indazol-3-yl}acetamide;
3-cyclopentyl-N-{6-[4-(dimethylamino)phenyl]-1H-indazol-3-yl}propanamide;
N-{6-[4-(dimethylamino)phenyl]-1H-indazol-3-yl}butanamide;
N-{6-[4-(dimethylamino)phenyl]-1H-indazol-3-yl}cyclopropanecarboxamide;
N-{6-[4-(dimethylamino)phenyl]-1H-indazol-3-yl}propanamide;
N-{6-[4-(dimethylamino)phenyl]-1H-indazol-3-yl}-2-methylpropanamide;
N-{6-[4-(dimethylamino)phenyl]-1H-indazol-3-yl}-2-phenoxypropanamide;
N-{6-[4-(dimethylamino)phenyl]-1H-indazol-3 -yl}cyclopentanecarboxamide;
N-{6-[4-(dimethylamino)phenyl]-1H-indazol-3-yl}cyclobutanecarboxamide;
N-[6-(2,5-(dimethoxyphenyl)-1H-indazol-3-yl]-2-(3-methoxypheny)acetamide;
N-[6-(2,5-dimethoxyphenyl)-1H-indazol-3-yl]-2,2-diphenylacetamide;
2(benzyloxy)-N-[6-(2,5-dimethoxyphenyl)1H-indazol-3-yl]acetamide;
N-[6-(2,5-dimethoxyphenyl)-1H-indazol-3-yl]furan-2-carboxamide;
2-cyclopentyl-N-[6-(2,5-dimethoxyphenyl)-1H-indazol-3-yl]acetamide;
N-[6-(2,5-dimethoxyphenyl) 1H-indazol-3-yl]-2-methoxybenzamide;
N-[6-(2,5-dimethoxyphenyl)-1H-indazol-3-yl]-3-fluorobenzamide;
3-chloro-N-[6(2,5-dimethoxyphenyl)-1H-indazol-3-yl] benzamide;
N-[6-(2,5-dimethoxyphenyl)-1H-indazol-3-yl]-3,4,5-trimethoxybenzamide;
N-[6-(2,5-dimethoxyphenyl)-1H-indazol-3-yl]-2,3,6-trifluorobenzamide
N-[6-(3,5-dimethylphenyl)-1H-indazol-3-yl]-2-(3-methoxyphenyl)acetamide;
2-(benzyloxy)-N-[6-(3,5-dimethylphenyl)-1H-indazol-3-yl]acetamide;
N-[6-(3 ,5-dimethylphenyl)-1H-indazol-3-yl]-furan-2-carboxamide;
2-cyclopentyl-N-[6-(3,5-dimethylphenyl)-1H-indazol-3-yl]acetamide;
N-[6-(3,5-dimethylphenyl)-1H-indazol-3-yl]-2-methoxybenzamide;
N-[6-(3,5-dimethylphenyl)-1H-indazol-3-yl]-3-fluorobenzamide;
3-chloro-N-[6-(3,5-dimethylphenyl)-1H-indazol-3-yl] benzamide;
N-[6-(3,5-dimethylphenyl)-1H-indazol-3-yl]-3,4,5-trimethoxybenzamide;
N-[6-(3,5-dimethylphenyl)-1H-indazol-3-yl]-2,3,6-trifluorobenzamide;
N-[6-(3-ethoxyphenyl)-1H-indazol-3-yl]-2,2-diphenylacetamide;
2-(benzyloxy)-N-[6-(3-ethoxyphenyl)-1H-indazol-3-yl] acetamide;
N-[6-(3-ethoxyphenyl)-1H-indazol-3-yl]furan-2-carboxamide;
N-[6-(3-ethoxyphenyl)-1H-indazol-3-yl]-2-methoxybenzamide;
N-[6-(3-ethoxyphenyl)-1H-indazol-3-yl]-3-fluorobenzamide;

3-chloro-N-[6-(3-ethoxyphenyl-1H-indazol-3-yl]benzamide;
N-[6-(3-ethoxyphenyl)-1H-indazol-3-yl]-3,4,5-trimethoxybenzamide;
N-[6-(3-ethoxyphenyl)-1H-indazol-3-yl]-2,4-dimethoxybenzamide
N-[6-(3-ethoxyphenyl)-1H-indazol-3-yl]-2,3,6-trifluorobenzamide;
N-[6-(2-ethoxyphenyl)-1H-indazol-3-yl]-2-(3-methoxyphenyl)acetamide;
N-[6-(2-ethoxyphenyl)-1H-indazol-3-yl]-2,2-diphenylacetamide;
2-(benzyloxy)-N-[6-(2-ethoxyphenyl)-1H-indazol-3-yl]acetamide;
N-[6-(2-ethoxyphenyl)-1H-indazol-3-yl]furan-2-carboxamide;
2-cyclopentyl-N-[6-(2-ethoxyphenyl)-1H-indazol-3-yl]acetamide;
N-[6-(2-ethoxyphenyl)-1H-indazol-3-yl]-2-methoxybenzamide;
N-[6-(2-ethoxyphenyl)-1H-indazol-3-yl]-3-fluorobenzamide;
3-chloro-N-[6-(2-ethoxyphenyl)-1H-indazol-3-yl]benzamide;
N-[6-(2-ethoxyphenyl)-1H-indazol-3-yl]-3,4,5-trimethoxybenzamide;
N-[6-(4-fluorophenyl)-1H-indazol-3-yl]-2-(3-methoxypheny)acetamide;
N-[6-(2-ethoxyphenyl)-1H-indazol-3-yl]-2,3,6-trifluorobenzamide;
N-[6-(2,6-dimethylphenyl)-1H-indazol-3-yl]-2-(3-methoxyphenyl)acetamide;
N-[6-(2,6-dimethylphenyl)-1H-indazol-3-yl]furan-2-carboxamide;
2-cyclopentyl-N-[6-(2,6-dimethylphenyl)-1H-indazol-3-yl]acetamide;
N-[6-(2,6-dimethylphenyl)-1H-indazol-3-yl]-3-fluorobenzamide;
3-chloro-N-[6-(2,6-dimethylphenyl)-1H-indazol-3-yl]benzamide;
N-[6-(2,6-dimethylphenyl)-1H-indazol-3-yl]-3,4,5-trimethoxybenzamide;
3,5-dichloro-N-[6-(2,6-dimethylphenyl)-1H-indazol-3-yl]benzamide;
N-[6-(2,6-dimethylphenyl)-1H-indazol-3-yl]-2,3,6-trifluorobenzamide;
3,5-dichloro-N-{6-[4-(dimethylamino)phenyl]-1H-indazol-3-yl}benzamide;
N-{6-[4-(dimethylamino)phenyl]-1H-indazol-3-yl}-2,3,6-trifluorobenzamide;
N-{6-[4-(ethylsulfanyl)phenyl]1H-indazol-3-yl}acetamide;
3-cyclopentyl-N-{6-[4-(ethylsulfanyl)phenyl]1H-indazol-3-yl}propanamide;
N-{6-[4-(ethylsulfanyl)phenyl]-1H-indazol-3-yl}butanamide;
N-{6-[4-(ethylsulfanyl)phenyl]-1H-indazol-3-yl}-2-methylpropanamide;
N-{6-[4-(ethylsulfanyl)phenyl]-1H-indazol-3-yl}-2-phenoxypropanamide;
N-{6-[4-(ethylsulfanyl)phenyl]-1H-indazol-3-yl}cyclobutanecarboxamide;
3-cyclopentyl-N-{6-[2-methoxy-5-(propan-2-yl)phenyl]-1H-indazol-3 -yl}propanamide;
N-{6-[2-methoxy-5-(propan-2-yl) phenyl]-1H-indazol-3-yl}cyclopropanecarboxamide;
N-{6-[2-methoxy-5-(propan-2-yl)phenyl]-1H-indazol-3-yl}-2-methylpropanamide;
N-{6-[2-methoxy-5-(propan-2-yl)phenyl]-1H-indazol-3-yl}-2-phenoxypropanamide;
N-{6-[2-methoxy-5-(propan-2-yl)phenyl]-1H-indazol-3-yl}cyclopentanecarboxamide;
2-methoxy-N-{6-[2-methoxy-5-(propan-2-yl)phenyl]-1H-indazol-3-yl}acetamide;
N-{6-[2-methoxy-5-(propan-2-yl)phenyl]-1H-indazol-3-yl}cyclobutanecarboxamide;
3-cyclopentyl-N-{6-[2-(methylsulfanyl)phenyl]-1H-indazol-3-yl}propanamide;
2-(4-methoxyphenyl)-N-{6-[2-(methylsulfanyl)phenyl]-1H-indazol-3-yl}acetamide;
N-{6-[2-(methylsulfanyl)phenyl]-1H-indazol-3-yl}butanamide;
N-{6-[2-(methylsulfanyl)phenyl]-1H-indazol-3-yl}cyclopropanecarboxamide;
2-methyl-N-{6-[2-(methylsulfanyl)phenyl]-1H-indazol-3-yl}propanamide;
N-{6-[2-(methylsulfanyl)phenyl]-1H-indazol-3-yl}-2-phenoxypropanamide;
N-{6-[2-(methylsulfanyl)phenyl]-1H-indazol-3-yl}cyclopentanecarboxamide;
2-methoxy-N-{6-[2-(methylsulfanyl)phenyl]-1H-indazol-3-yl}acetamide;
N-{6-[2-(methylsulfanyl)phenyl]-1H-indazol-3-yl}cyclobutanecarboxamide;
3-cyclopentyl-N-{6-[3-(trifluoromethoxy)phenyl]-1H-indazol-3-yl}propanamide;
N-{6-[3-(trifluoromethoxy)phenyl]-1H-indazol-3-yl}butanamide;
2-methyl-N-{6-[3(trifluoromethoxy)phenyl]1H-indazol-3-yl}propanamide;
2-phenoxy-N-{6-[3-(trifluoromethoxy)phenyl]-1H-indazol-3-yl}propanamide;
N-{6-[3-(trifluoromethoxy)phenyl]-1H-indazol-3-yl}cyclopentanecarboxamide;
N-[6-(2,5-dimethylphenyl) 1H-indazol-3-yl]-2-phenylacetamide;
N-[6-(2,5-dimethylphenyl)-1H-indazol-3-yl]acetamide;
3-cyclopentyl-N-[6-(2,5-dimethylphenyl)-1H-indazol-3-yl]propanamide;
N-[6-(2,5-dimethylphenyl)-1H-indazol-3-yl]butanamide;
N-[6-(2,5-dimethylphenyl)-1H-indazol-3-yl]cyclopropanecarboxamide;
N-[6-(2,5-dimethylphenyl)-1H-indazol-3-yl]-2-methylpropanamide;
N-[6-(2,5-dimethylphenyl)-1H-indazol-3-yl]-2-phenoxypropanamide;
N-[6-(2,5-dimethylphenyl)-1H-indazol-3-yl]cyclopentanecarboxamide;
N-[6-(2,5-dimethylphenyl)-1H-indazol-3-yl]-2-methoxyacetamide;
N-[6-(2,5-dimethylphenyl)-1H-indazol-1-yl]cyclobutanecarboxamide;
N-[6-(2,5-difluorophenyl)-1H-indazol-3-yl]acetamide;
3-cyclopentyl-N-[6-(2,5-difluorophenyl)-1H-indazol-3-yl]propanamide;
N-[6-(2,5-difluorophenyl)-1H-indazol-3-yl]-2-(4-methoxyphenyl)acetamide;
N-[6-(2,5-difluorophenyl)-1H-indazol-3-yl]butanamide;
N-[6-(2,5-difluorophenyl)-1H-indazol-3-yl]cyclopropanecarboxamide;
N-[6-(2,5-difluorophenyl)-1H-indazol-3-yl]-2-methylpropanamide;

N-[6-(2,5-difluorophenyl)-1H-indazol-3-yl]-2-phenoxypropanamide;
N-[6-(2,5-difluorophenyl(-1H-indazol-3-yl]cyclopentanecarboxamide;
N-[6-(2,5-difluorophenyl)-1H-indazol-3-yl]2-methoxyacetamide;
N-[6-(2,5-difluorophenyl)-1H-indazol-3-yl]cyclobutanecarboxamide;
N-[6-(3,4-difluorophenyl)-1H-indazol-3-yl]acetamide;
3-cyclopentyl-N-[6-(3,4-difluorophenyl)-1-H-indazol-3-yl]propanamide;
N-[6-(3,4-difluorophenyl)-1H-indazol-3-yl]-2-phenoxypropanamide;
N-[6-(3,4-difluorophenyl)-1H-indazol-3-yl]-2-methoxyacetamide;
N-[6-(3,4-difluorophenyl)-1H -indazol-3-yl]cyclobutanecarboxamide;
N-[6-(5-fluoro-2-methoxyphenyl)-1H-indazol-3-yl]acetamide;
3-cyclopentyl-N-[6-(5-fluoro-2-methoxyphenyl)-1H-indazol-3-yl]propanamide;
N-[6-(5-fluoro-2-methoxyphenyl)-1H-indazol-3-yl]cyclopropanecarboxamide;
N-[6-(5-fluoro-2-methoxyphenyl)-1H-indazol-3-yl]-2-methylpropanamide;
N-[6-(5-fluoro-2-methoxyphenyl)-1H-indazol-3-yl]-2-phenoxypropanamide;
N-[6-(5-fluoro-2-methoxyphenyl)-1H-indazol-3-yl]cyclopentanecarboxamide;
N-[6-(5-fluoro-2-methoxyphenyl)-1H-indazol-3-yl]-2-methoxyacetamide;
N-[6-(5-fluoro-2-methoxyphenyl)-1H-indazol-3-yl]cyclobutanecarboxamide;
N-{6-[4-(ethylsulfanyl)phenyl]-1H-indazol-3-yl}furan-2-carboxamide;
2-cyclopentyl-N-{6-[4-(ethylsulfanyl)phenyl]-1H-indazol-3-yl}acetamide;
N-{6-[4-(ethylsulfanyl)phenyl]-1H-indazol-3-yl}-3,4,5-trimethoxybenzamide;
N-{6-[4-(ethylsulfanyl)phenyl]-1H-indazol-3-yl}-2,4-dimethoxybenzamide;
2-(3-methoxyphenyl)-N-{6-[2-methoxy-5-(propan-2-yl)phenyl]1H-indazol-3-yl}acetamide;
N-{6-[2-methoxy-5-(propan-2-yl)phenyl]-1H-indazol-3-yl}-2,2-diphenylacetamide;
N-{6-[2-methoxy-5-(propan-2-yl)phenyl]-1H-indazol-3-yl}furan-2-carboxamide;
2-cyclopentyl-N-{6-[2-methoxy-5(propan-2-yl)phenyl]-1H-indazol-3-yl}acetamide;
2-methoxy-N-{6-[2-methoxy-5-(propan-2-yl)phenyl]-1H-indazol-3-yl}benzamide;
3-chloro-N-{6-[2-methoxy-5-(propan-2-yl)phenyl]-1H-indazol-3-yl}benzamide;
3,4,5-trimethoxy-N-{6-[2-methoxy-5-(propan-2-yl)phenyl]-1H-indazol-3-yl}benzamide;
3,5-dichloro-N-{6-[2-methoxy-5-(propan-2-yl)phenyl]-1H-indazol-3-yl}benzamide;
2,4-dimethoxy-N-{6-[2-methoxy-5-(propan-2-yl)phenyl]-1H-indazol-3-yl}benzamide;
2,3,6-trifluoro-N-{6-[2-methoxy-5-(propan-2-yl)phenyl]-1H-indazol-3-yl}benzamide;
2-(3-methoxyphenyl)-N-{6-[2-(methylsulfanyl)phenyl]-1H-indazol-3-yl}acetamide;
N-{6-[2-(methylsulfanyl)phenyl]-1H-indazol-3-yl}-2,2-diphenylacetamide;
2-(benzyloxy)-N-{6-[2-(methylsulfanyl)phenyl]-1H-indazol-3-yl}acetamide;
2-cyclopentyl-N-{6-[2-(methylsulfanyl)phenyl]-1H-indazol-3-yl}acetamide;
2-methoxy-N-{6-[2-(methylsulfanyl)phenyl]-1H-indazol-3-yl}benzamide;
3-chloro-N-{6-[2-(methylsulfanyl)phenyl]-1H-indazol-3-yl}benzamide;
3,4,5-trimethoxy-N-{6-[2-(methylsulfanyl)phenyl]-1H-indazol-3-yl}benzamide;
3,5-dichloro-N-{6-[2-(methylsulfanyl)phenyl]-1H-indazol-3-yl}benzamide;
2,4-dimethoxy-N-{6-[2-(methylsulfanyl)phenyl]-1H-indazol-3-yl}benzamide;
2,3,6-triiluoro-N-{6-[2-(methylsulfanyl)phenyl]-1H-indazol-3-yl}benzamide;
2,2-diphenyl-N-{6-[3-(trifluoromethoxy)phenyl]-1H-indazol-3-yl}acetamide;
2-(benzyloxy)-N-{6-[3-(trifluoromethoxy)phenyl]-1H-indazol-3-yl}acetamide;
N-[6-(2,5-difluorophenyl)-1H-indazol-3-yl]-2,3,6-trifluorobenzamide;
2-(benzyloxy)-N-[6-(3,4-difluorophenyl)-1H-indazol-3-yl]acetamide;
N-[6-(3,4-difluorophenyl)-1H-indazol-3-yl]furan-2-carboxamide;
N-[6-(3,4-difluorophenyl)-1H-indazol-3-yl]-2-methoxybenzamide;
3-chloro-N-[6-(3,4-difluorophenyl)-1H-indazol-3-yl]benzamide;
N-[6-(3,4-difluorophenyl)-1H-indazol-3-yl]-3,4,5-trimethoxybenzamide;
N-[6-(3,4-difluorophenyl)-1H-indazol-3-yl]-2,3,6-trifluorobenzamide;
N-[6-(5-fluoro-2-methoxyphenyl)-1H-indazol-3-yl]-2-(3-methoxyphenyl)acetamide;
N-[6-(5-fluoro-2-methoxyphenyl)-1H-indazol-3-yl]-2,2-diphenylacetamide;
2-(benzyloxy)-N-[6-(5-fluoro-2-methoxyphenyl)-1H-indazol-3-yl]acetamide;
N-[6-(5-fluoro-2-methoxyphenyl)-1H-indazol-3-yl]furan-2-carboxamide;
2-cyclopentyl-N-[6-(5-fluoro-2-methoxyphenyl)-1H-indazol-3-yl]acetamide;
N-[6-(5-fluoro-2-methoxyphenyl)-1H-indazol-3-yl]-2-methoxybenzamide;
3-chloro-N-[6-(5-fluoro-2-methoxyphenyl)-1H-indazol-3-yl]benzamide;
N-[6-(5-fluoro-2-methoxyphenyl)-1H-indazol-3-yl]-3,4,5-trimethoxybenzamide;
N-[6-(5-fluoro-2-methoxyphenyl)-1H-indazol-3-yl]-2,4-dimethoxybenzamide;
2,3,6-trifluoro-N-[6-(5-fluoro-2-methoxyphenyl)-1H-indazol-3-yl]benzamide;
N-[6-(4-methoxyphenyl)-1H-indazol-3-yl]acetamide;
3-cyclopentyl-N-[6-(4-methoxyphenyl)-1H-indazol-3-yl]propanamide;
N-[6-(4-methoxyphenyl)-1H-indazol-3-yl]butanamide;
N-[6-(4-methoxyphenyl)-1H-indazol-3-yl]cyclopropanecarboxamide;
N-[6-(4-methoxyphenyl)-1H-indazol-3-yl]propanamide;
N-[6-(4-methoxyphenyl)-1H-indazol-3-yl]-2-methylpropanamide;
N-[6-(4-methoxyphenyl)-1H-indazol-3-yl]-2-phenoxypropanamide;
2-methoxy-N-[6-(4-methoxyphenyl)-1H-indazol-3-yl]acetamide;
N-[6-(4-fluorophenyl)-1H-indazol-3-yl]-2-phenylacetamide;

N-[6-(4-fluorophenyl)-1H-indazol-3-yl]acetamide;
3-cyclopentyl-N-[6-(4-fluorophenyl)-1H-indazol-3-yl]propanamide;
N-[6-(4-fluorophenyl)-1H-indazol-3-yl]-2-(4-methoxyphenyl)acetamide;
N-[6-(4-fluorophenyl)-1H-indazol-3-yl]butanamide;
N-[6-(4-fluorophenyl)-1H-indazol-3-yl]cyclopropanecarboxamide;
N-[6-(4-fluorophenyl)-1H-indazol-3-yl]propanamide;
N-[6-(4-fluorophenyl) 1H-indazol-3-yl]-2-methylpropanamide;
N-[6-(4-fluorophenyl) 1H-indazol-3-yl]-2-phenoxypropanamide;
N-[6-(4-fluorophenyl)-1H-indazol-3-yl]cyclopentanecarboxamide;
N-[6-(4-fluorophenyl)-1H-indazol-3-yl]-2-methoxyacetamide;
N-[6-(3-methoxyphenyl)-1H-indazol-3-yl]-2-phenylacetamide;
N-[6-(3-methoxyphenyl)-1H-indazol-3-yl]acetamide;
3-cyclopentyl-N-[6-(3-methoxyphenyl) 1H-indazol-3-yl]propanamide;
N-[6-(3-methoxyphenyl)-1H-indazol-3-yl]butanamide;
N-[6-(3-methoxyphenyl)-1H-indazol-3-yl]cyclopropanecarboxamide;
N-[6-(3-methoxyphenyl)-1H-indazol-3-yl]propanamide;
N-[6-(3-methoxyphenyl)-1H-indazol-3-yl]-2-methylpropanamide;
N-[6-(3-methoxyphenyl)-1H-indazol-3-yl]-2-phenoxypropanamide;
N-[6-(3-methoxyphenyl)-1H-indazol-3-yl]cyclopentanecarboxamide;
2-methoxy-N-[6-(3-methoxyphenyl)-1H-indazol-3-yl]acetamide;
N-[6-(thiophen-3-yl)-1H-indazol-3-yl]acetamide;
3-cyclopentyl-N-[6-(thiophen-3-yl)-1H-indazol-3-yl]propanamide;
N-[6-(thiophen-3-yl)-1H-indazol-3-yl]butanamide;
N-[6-(thiophen-3-yl)-1H-indazol-3-yl]cyclopropanecarboxamide;
N-[6-(thiophen-3-yl)-1H-indazol-3-yl]propanamide;
2-methyl-N-[6-(thiophen-3-yl)-1H-indazol-3-yl]propanamide;
2-phenoxy-N-[6-(thiophen-3-yl)-1H-indazol-3-yl]propanamide;
N-[6-(thiophen-3-yl)-1H-indazol-3-yl]cyclopentanecarboxamide;
N-(6-phenyl-1H-indazol-3-yl)acetamide;
3-cyclopentyl-N-(6-phenyl-1H-indazol-3-yl)propanamide;
N-(6-phenyl-1H-indazol-3-yl)butanamide;
N-(6-phenyl-1H-indazol-3-yl)cyclopropanecarboxamide;
N-(6-phenyl-1H-indazol-3-yl)propanamide;
2-methyl-N-(6-phenyl-1H-indazol-3-yl)propanamide;
2-phenoxy-N-(6-phenyl-1H-indazol-3-yl)propanamide;
N-(6-phenyl-1H-indazol-3-yl)cyclopentanecarboxamide;
2-methoxy-N-(6-phenyl-1H-indazol-3-yl)acetamide;
N-[6-(4-methylphenyl)-1H-indazol-3-yl]-2-phenylacetamide;
N-[6-(4-methylphenyl)-1H-indazol-3-yl]acetamide;
3-cyclopentyl-N-[6-(4-methylphenyl)-1H-indazol-3-yl]propanamide;
N-[6-(4-methylphenyl)-1H-indazol-3-yl]butanamide;
N-[6-(4-methylphenyl)-1H-indazol-3-yl]cyclopropanecarboxamide;
N-[6-(4-methylphenyl)-1H-indazol-3-yl]propanamide;
2-methyl-N-[6-(4-methylphenyl)-1H-indazol-3-yl]propanamide;
N-[6-(4-methylphenyl)-1H-indazol-3-yl]-2-phenoxypropanamide;
N-[6-(4-methylphenyl)-1H-indazol-3-yl]cyclopentanecarboxamide;
N-[6-(2-methoxyphenyl)-1H-indazol-3-yl]acetamide;
3-cyclopentyl-N-[6-(2-methoxyphenyl)-1H-indazol-3-yl]propanamide;
N-[6-(2-methoxyphenyl)-1H-indazol-3-yl]butanamide;
N-[6-(2-methoxyphenyl)-1H-indazol-3-yl]cyclopropanecarboxamide;
N-[6-(2-methoxyphenyl)-1H-indazol-3-yl]propanamide;
N-[6-(2-methoxyphenyl)-1H-indazol-3-yl]-2-methylpropanamide;
N-[6-(2-methoxyphenyl)-1H-indazol-3-yl]-2-phenoxypropanamide;
N-[6-(2-methoxyphenyl)-1H-indazol-3-yl]cyclopentanecarboxamide;
2-methoxy-N-[6-(2-methoxyphenyl)-1H-indazol-3-yl]acetamide;
N-[6-(thiophen-2-yl)-1H-indazol-3-yl]acetamide;
3-cyclopentyl-N-[6-(thiophen-2-yl)-1H-indazol-3-yl]propanamide;
N-[6-(thiophen-2-yl)-1H-indazol-3-yl]butanamide;
N-[6-(thiophen-2-yl)-1H-indazol-3-yl]cyclopropanecarboxamide;
2-methyl-N-[6-(thiophen-2-yl)-1H-indazol-3-yl]propanamide;
N-[6-(thiophen-2-yl)-1H-indazol-3-yl]cyclopentanecarboxamide;
N-[6-(4-methoxyphenyl)-1H-indazol-3-yl]cyclobutanecarboxamide;
N-[6-(3-methoxyphenyl)-1H-indazol-3-yl]-2-phenylbutanamide;
2-(benzyloxy)-N-[6-(3-methoxyphenyl)-1H-indazol-3-yl]acetamide;
N-[6-(3-methoxyphenyl)-1H-indazol-3-yl]furan-2-carboxamide;
2-cyclopentyl-N-[6-(3-methoxyphenyl)-1H-indazol-3-yl]acetamide;
N-[6-(3-methoxyphenyl)-1H-indazol-3-yl]-2-methylbutanamide;
N-[6-(thiophen-3-yl)-1H-indazol-3-yl]cyclobutanecarboxamide
2-(3-methoxyphenyl)-N-[6-(thiophen-3-y1)-1H-indazol-3-yl]acetamide;
2,2-diphenyl-N-[6-(thiophen-3-yl)-1H-indazol-3-yl]acetamide;
2-(benzyloxy)-N-[6-(thiophen-3-yl)-1H-indazol-3-yl]acetamide;
N-[6-(thiophen-3-yl)-1H-indazol-3-yl]furan-2-carboxamide;
N-(6-phenyl-1H-indazol-3-yl)cyclobutanecarboxamide;
2,2-diphenyl-N-(6-phenyl-1H-indazol-3-yl)acetamide;
2(benzyloxy)-N-(6-phenyl-1H-indazol-3-yl)acetamide;
2-methyl-N-(6-phenyl1H-indazol-3-yl)butanamide;
N-[6-(4-methylphenyl)-1H-indazol-3-yl]cyclobutanecarboxamide;
N-[6-(4-methylphenyl)-1H-indazol-3-yl]-2,2-diphenylacetamide;
2-(benzyloxy)-N-[6-(4-methylphenyl)-1H-indazol-3-yl]acetamide;
N-[6-(4-methylphenyl-1H-indazol-3-yl]furan-2-carboxamide;
2-cyclopentyl-N-[6-(4-methylphenyl)-1H-indazol-3-yl]acetamide;

N-[6-(2-methoxyphenyl)-1H-indazol-3-yl]cyclobutan-ecarboxamide;
2-(3-methoxyphenyl)-N-[6-(2-methoxyphenyl) 1H-indazol-3-yl]acetamide;
N-[6-(2-methoxyphenyl)-1H-indazol-3-yl]-2,2-diphenylacetamide;
2-(benzyloxy)-N-[6-(2-methoxyphenyl)-1H-indazol-3-yl]acetamide;
N-[6-(2-methoxyphenyl)-1H-indazol-3-yl]furan-2-carboxamide;
2-cyclopentyl-N-[6-(2-methoxyphenyl)-1H-indazol-3-yl]acetamide;
N-[6-(thiophen-2-yl)-1H-indazol-3-yl]cyclobutanecarboxamide;
2-(3-methoxyphenyl)-N-[6-(thiophen-2-yl)-1H-indazol-3-yl]acetamide;
2,2-diphenyl-N-[6-(thiophen-2-yl)-1H-indazol-3-yl]acetamide;
2-(benzyloxy)-N-[6-(thiophen-2-yl)-1H-indazol-3-yl]acetamide;
N-[6-(thiophen-2-yl) 1H-indazol-3-yl]furan-2-carboxamide;
2-cyclopentyl-N-[6-(thiophen-3-yl)1H-indazol-3-yl]acetamide;
N-(6-phenyl-1H-indazol-3-yl)furan-2-carboxamide;
N-[6-(3-cyanophenyl)-1H-indazol-3-yl]-3-fluorobenzamide;
N-[6-(3-cyanophenyl)-1H-indazol-3-yl]-3,4,5-trimethoxybenzamide;
N-[6-(3-cyanophenyl)-1H-indazol-3-yl]-2,4-dimethoxybenzamide;
N-[6-(3-cyanophenyl)-1H-indazol-3-yl]-2,3,6-trifluorobenzamide;
3-cyclopentyl-N-[6-(2,5-dimethoxyphenyl)-1H-indazol-3-yl]propanamide;
N-[6-(2,5-dimethoxyphenyl)-1H-indazol-3-yl]cyclopropanecarboxamide;
N-[6-(2,5-dimethoxyphenyl)-1H-indazol-3-yl]-2-methylpropanamide;
N-[6-(2,5-dimethoxyphenyl)-1H-indazol-3-yl]-2-phenoxypropanamide;
N-[6-(2,5-dimethoxyphenyl)-1H-indazol-3-yl]cyclopentanecarboxamide;
N-[6-(2,5-dimethoxyphenyl)-1H-indazol-3-yl]cyclobutanecarboxamide;
N-[6-(3,5-dimethylphenyl)-1H-indazol-3-yl]acetamide;
3-cyclopentyl-N-[6-(3,5-dimethylphenyl)-1H-indazol-3-yl]propanamide;
N-[6-(3,5-dimethylphenyl)-1H-indazol-3-yl]cyclopropanecarboxamide;
N-[6-(3,5-dimethylphenyl)-1H-indazol-3-yl]-2-methylpropanamide;
N-[6-(3,5-dimethylphenyl)-1H-indazol-3-yl]cyclopentanecarboxamide
2-(benzyloxy)-N-[6-(3,4-dimethylphenyl)-1H-indazol-3-yl]acetamide;
N-[6-(3,4-dimethylphenyl)-1H-indazol-3-yl]furan-2-carboxamide;
N-[6-(3,4-dimethylphenyl)-1H-indazol-3-yl]-2-methoxybenzamide;
N-[6-(3,4-dimethylphenyl)-1H-indazol-3-yl]-3-fluorobenzamide;
N-[6-(3,4-dimethylphenyl)-1H-indazol-3-yl]-3,4,5-trimethoxybenzamide;
N-{6[4(propan-2-yl)phenyl]-1H-indazol-3-yl}furan-2carboxamide;
2-methoxy-N-{6-[4-(propan-2-yl)phenyl]-1H-indazol-3-yl}benzamide;
3,4,5-trimethoxy-N-{6-[4-(propan-2-yl)phenyl]-1H-indazol-3-yl}benzamide;
2,3,6-trifluoro-N-{6-[4-(propan-2-yl)phenyl]-1H-indazol-3-yl}benzamide;
N-{6-[4-(dimethylamino)phenyl]-1H-indazol-3-yl}-2-(3-methoxypheny)acetamide;
N-{6-[4-(dimethylamino)phenyl]-1H-indazol-3-yl}-2,2-diphenylacetamide;
2-(benzyloxy)-N-{6-[4-(dimethylamino)phenyl]-1H-indazol-3-yl}acetamide;
N-{6-[4(dimethylamino)phenyl]-1H-indazol-3-yl}furan-2-carboxamide;
2-cyclopentyl-N-{6-[4-(dimethylamino)phenyl]-1H-indazol-3-yl}acetamide;
N-{6[4-(dimethylamino)phenyl]-1H-indazol-3-yl}-2-methoxybenzamide;
3-chloro-N-{6-[4-(dimethylamino)phenyl]-1H-indazol-3-yl}benzamide;
N-{6-[4-(dimethylamino)phenyl]-1H-indazol-3-yl}-3,4,5-trimethoxybenzamide;
N-{6-[3-(trifluoromethoxy)phenyl]-1H-indazol-3-yl}furan-2carboxamide;
2-cyclopentyl-N-{6-[3-(trifluoromethoxy)phenyl]-1H-indazol-3-yl}acetamide;
3,4,5-trimethoxy-N-{6-[3-(trifluoromethoxy)phenyl]-1H-indazol-3-yl}benzamide;
2,4-dimethoxy-N-{6-[3-(trifluoromethoxy)phenyl]-1H-indazol-3-yl}benzamide;
2,3,6-trifluoro-N-{6-[3-(trifluoromethoxy)phenyl]-1H-indazol-3-yl}benzamide;
N-[6-(2,5-dimethylphenyl)-1H-indazol-3-yl]-2-(3-methoxyphenyl)acetamide;
N-[6-(2,5-dimethylphenyl)-1H-indazol-3-yl]-2,2-diphenylacetamide;
2-(benzyloxy)-N-[6-(2,5-dimethylphenyl)-1H-indazol-3-yl]acetamide;
N-[6-(2,5-dimethylphenyl)-1H-indazol-3-yl]furan-2-carboxamide;
3-chloro-N-[6-(2,5-dimethylphenyl)-1H-indazol-3-yl]benzamide;
N-[6-(2,5-dimethylphenyl)-1H-indazol-3-yl]-3,4,5-trimethoxybenzamide;
3,5-dichloro-N-[6-(2,5-dimethylphenyl)-1H-indazol-3-yl]benzamide;
N-[6-(2,5-dimethylphenyl)-1H-indazol-3-yl]-2,3,6-trifluorobenzamide;
N-[6-(2,5-difluorophenyl)-1H-indazol-3-yl]-2-(3-methoxyphenyl)acetamide;
N-[6-(2,5-difluorophenyl)-1H-indazol-3-yl]-2,2-diphenylacetamide;
N-[6-(2,5-difluorophenyl)-1H-indazol-3-yl]furan-2-carboxamide;
2-cyclopentyl-N-[6-(2,5-difluorophenyl)-1H-indazol-3-yl]acetamide;
N-[6-(2,5-difluorophenyl)-1H-indazol-3-yl]-3,4,5-trimethoxybenzamide;
N-[6-(4-methoxyphenyl)-1H-indazol-3-yl]-2,2-diphenylacetamide;
N-[6-(4-methoxyphenyl)-1H-indazol-3-yl]furan-2-carboxamide;
N-[6-(4-fluorophenyl)-1H-indazol-3-yl]cyclobutanecarboxamide;
N-[6-(4-fluorophenyl)-1H-indazol-3-yl]-2,2-diphenylacetamide;

2-(benzyloxy)-N-[6-(4-fluorophenyl)-1H-indazol-3-yl]acetamide;
N-[6-(4-fluorophenyl)-1H-indazol-3-yl]furan-2-carboxamide;
2-cyclopentyl-N-[6-(4-fluorophenyl)-1H-indazol-3-yl]acetamide;
N-[6-(3-methoxyphenyl)-1H-indazol-3-yl]cyclobutanecarboxamide;
2-(3-methoxyphenyl)-N-[6-(3-methoxyphenyl)-1H-indazol-3-yl]acetamide;
N-[6-(3-methoxyphenyl)-1H-indazol-3-yl]-2,2-diphenylacetamide;
N-[6-(4-acetylphenyl)-1H-indazol-3-yl]-2-cyclopentylacetamide;
N-[6-(4-acetylphenyl)-1H-indazol-3-yl]-3-fluorobenzamide;
N-[6-(4-acetylphenyl)-1H-indazol-3-yl]-2,4-dimethoxybenzamide;
N-[6-(3-chloro-4-fluorophenyl)-1H-indazol-3-yl]2-methoxybenzamide;
N-[6-(3-chloro-4-fluorophenyl)-1H-indazol-3-yl]-3,4,5-trimethoxybenzamide;
N-[6-(3-chloro-4-fluorophenyl)-1H-indazol-3-yl]-2,3,6-trifluorobenzamide;
N-[6-(3-chlorophenyl)-1H-indazol-3-yl]furan-2-carboxamide;
2-(benzyloxy)-N-[6-(3,4-dichlorophenyl)-1H-indazol-3-yl]acetamide;
N-{6-[4-(trifluoromethoxy)phenyl]-1H-indazol-3-yl}furan-2-carboxamide;
N-[6-(4-cyanophenyl)-1H-indazol-3-yl]-2-cyclopentylacetamide;
N-[6-(4-cyanophenyl)-1H-indazol-3-yl]-2-methoxybenzamide;
3,5-dichloro-N-[6-(4-cyanophenyl)-1H-indazol-3-yl]benzamide;
2-cyclopentyl-N-[6-(3-ethoxyphenyl)-1H-indazol-3-yl]acetamide;
N-[6-(2,6-dimethylphenyl) 1H-indazol-3-yl]-2,2-diphenylacetamide;
N-{6-[4-(ethylsulfanyl)phenyl]-1H-indazol-3-yl}-2-methoxyacetamide;
N-{6-[4-(ethylsulfanyl)phenyl]-1H-indazol-3-yl}-2,3,6-trifluorobenzamide;
N-[6-(4-methoxyphenyl)-1H-indazol-3-yl]cyclopentanecarboxamide;
2-methoxy-N-[6-(4-methylphenyl)-1H-indazol-3-yl]acetamide;
2-phenoxy-N-[6-(thiophen-2-yl)-1H-indazol-3-yl]propanamide;
2-methoxy-N-[6-(thiophen-2-yl)-1H-indazol-3-yl]acetamide;
2-(3-methoxyphenyl)-N-[6-(4-methoxyphenyl)-1H-indazol-3-yl]acetamide;
2-cyclopentyl-N-[6-(4-methoxyphenyl)-1H-indazol-3-yl]acetamide;
N-[6-(3,4-dimethylphenyl)-1H-indazol-3-yl]-2,3,4,5-tetrafluorobenzamide;
2-chloro-N-[6-(3,4-dimethylphenyl)-1H-indazol-3-yl]-6-fluorobenzamide;
N-[6-(3,4-dimethylphenyl)-1H-indazol-3-yl]-2,4-difluorobenzamide;
2,3,4,5-tetrafluoro-N-{6-[4-(propan-2-yl)phenyl]-1H-indazol-3-yl}benzamide;
2,4-(4-chlorophenoxy)-N-{6-[4(propan-2-yl)phenyl]-1H-indazol-3-yl}acetamide;
2,4-difluoro-N-{6-[4-(propan-2-yl)phenyl]-1H-indazol-3-yl}benzamide;
N-{6-[4-(dimethylamino)phenyl]-1H-indazol-3-yl}-2,3,4,5-tetrafluorobenzamide;
2-(4-chlorophenoxy)-N-{6-[4-(dimethylamino)phenyl]-1H-indazol-3-yl}acetamide;
N-{6-[4-(dimethylamino)phenyl]-1H-indazol-3-yl}-2,4-difluorobenzamide;
2-{[6-(4-cyanophenyl)-1H-indazol-3-yl]amino}-2-oxo-1-phenylethyl acetate;
N-[6-(2,4-difluorophenyl)-1H-indazol-3-yl]pentanamide;
N-[6-(2,4-difluorophenyl)-1H-indazol-3-yl]-3,4-difluorobenzamide;
N-[6-(2,4-difluorophenyl)-1H-indazol-3-yl]benzamide;
N-[6-(2,4-difluorophenyl)-1H-indazol-3-yl]-2,6-difluorobenzamide;
2-{[6-(2,4-difluorophenyl)-1H-indazol-3-yl]amino}-2-oxoethyl acetate;
2-{[6-(2,4-difluorophenyl)-1H-indazol-3-yl]amino}-2-oxo-1-phenylethyl acetate;
N-[6-(2,4-dimethoxyphenyl)-1H-indazol-3-yl]-3,4-difluorobenzamide;
3-cyano-N-[6-(2,4-dimethoxyphenyl)-1H-indazol-3-yl]benzamide;
N-[6-(2,4-dimethoxyphenyl)-1H-indazol-3-yl]-2-fluorobenzamide;
N-[6-(2,4-dimethoxyphenyl)-1H-indazol-3-yl]-2,6-difluorobenzamide;
2-{[6-(2,4-dimethoxyphenyl)-1H-indazol-3-yl]amino}-2-oxoethyl acetate;
2-{[6-(2,4-dimethoxyphenyl)-1H-indazol-3-yl]amino}-2-oxo-1-phenylethyl acetate;
N-[6-(3-cyanophenyl)-1H-indazol-3-yl]-3-phenylpropanamide;
2-{[6-(3-cyanophenyl)-1H-indazol-3-yl]amino}-2-oxoethyl acetate;
2,3,4,5-tetrafluoro-N-[6-(3-methoxyphenyl)-1H-indazol-3-yl]benzamide;
2-(4-chlorophenoxy)-N-[6-(3-methoxyphenyl)-1H-indazol-3-yl]acetamide;
N-[6-(3-methoxyphenyl)-1H-indazol-3-yl]cyclohexanecarboxamide;
2,4-difluoro-N-[6-(3-methoxyphenyl)-1H-indazol-3-yl]benzamide;
2,3,4,5-tetrafluoro-N-[6-(4-fluorophenyl)-1H-indazol-3-yl]benzamide;
2-(4-chlorophenoxy)-N-[6-(4-fluorophenyl)-1H-indazol-3-yl]acetamide;
2,4-difluoro-N-[6-(4-fluorophenyl)-1H-indazol-3-yl]benzamide;
2,4-difluoro-N-[6-(4-methoxyphenyl)-1H-indazol-3-yl]benzamide;
N-[6-(5-fluoro-2-methoxyphenyl)-1H-indazol-3-yl]-3-phenylpropanamide;
3,4-difluoro-N-[6-(5-fluoro-2-methoxyphenyl)-1H-indazol-3-yl]benzamide;
3-cyano-N-[6-(5-fluoro-2-methoxyphenyl)-1H-indazol-3-yl]benzamide;
2-fluoro-N-[6-(5-fluoro-2-methoxyphenyl)-1H-indazol-3-yl]benzamide;
2,6-difluoro-N-[6-(5-fluoro-2-methoxyphenyl)-1H-indazol-3-yl]benzamide;
2-{[6-(5-fluoro-2-methoxyphenyl)-1H-indazol-3-yl]amino}-2-oxoethyl acetate;
2-{[6-(5-fluoro-2-methoxyphenyl)-1H-indazol-3-yl]amino}-2-oxo-1-phenylethyl acetate;

N-[6-(5-fluoro-2-methoxyphenyl)-1H-indazol-3-yl]-2-(thiophen-2-yl)acetamide;
N-[6-(3-chlorophenyl)-1H-indazol-3-yl]-2,3,4,5-tetrafluorobenzamide;
2-(4-chlorophenoxy)-N-[6-(3,4-dimethylphenyl)-1H-indazol-3-yl]acetamide;
N-[6-(2,4-difluorophenyl)-1H-indazol-3-yl]-2-fluorobenzamide;
N-[6-(3-cyanophenyl)-1H-indazol-3-yl]-2-fluorobenzamide;
2-{[6-(3-cyanophenyl)-1H-indazol-3-yl]amino}-2-oxo-1-phenylethyl acetate;
2-(4-chlorophenoxy)-N-[6-(2,4-difluorophenyl)-1H-indazol-3-yl]acetamide;
N-[6-(2,5-dimethylphenyl)-1H-indazol-3-yl]-Nalpha-[(4-methylphenyl)sulfonyl]-L-phenylalaninamide;
N-[6-(3-methoxyphenyl)-1H-indazol-3-yl]-Nalpha-[4-methylphenyl)sulfonyl]-L-phenylalaninamide;
N-[6-(3,4-difluorophenyl)-1H-indazol-3-yl]-2,6-difluorobenzamide;
2,3,4,5-tetrafluoro-N-[6-(3-methylphenyl)-1H-indazol-3-yl]benzamide;
2-(4-chlorophenoxy)-N-[6-(3-methylphenyl)-1H-indazol-3-yl]acetamide;
N-[6-(3-methylphenyl)-1H-indazol-3-yl]cyclohexanecarboxamide;
N-[6-(3-methylphenyl)-1H-indazol-3-yl]-Nalpha-[(4-methylphenyl)sulfonyl]-L-phenylalaninamide;
2,4-difluoro-N-[6-(3-methylphenyl)-1H-indazol-3-yl]benzamide;
N-{6-[3-(acetylamino)phenyl]-1H-indazol-3-yl}-2-(4-chlorophenoxy)acetamide;
N-{6-[3-(acetylamino)phenyl]-1H-indazol-3-yl}-Nalpha-[(4-methylphenyl)sulfonyl]-L-phenylalaninamide;
N-[6-(4-acetylphenyl)-1H-indazol-3-yl]cyclohexanecarboxamide;
N-[6-(4-acetylphenyl)-1H-indazol-3-yl]-2,4-difluorobenzamide;
N-[6-(3-chloro-4-fluorophenyl)-1H-indazol-3-yl]-2,3,4,5-tetrafluorobenzamide;
N-[6-(3-chloro-4-fluorophenyl)-1H-indazol-3-yl]-2-(4-chlorophenoxy)acetamide;
N-[6-(3-chloro-4-fluorophenyl)-1H-indazol-3-yl]-2,4-difluorobenzamide;
2-chloro-N-[6-(3-chlorophenyl)-1H-indazol-3-yl]-6-fluorobenzamide;
2-(4-chlorophenoxy)-N-[6-(3-chlorophenyl)-1H-indazol-3-yl]acetamide;
N-[6-(3-chlorophenyl)-1H-indazol-3-yl]-2,4-difluorobenzamide;
N-[6-(3,4-dichlorophenyl)-1H-indazol-3-yl]-2,3,4,5-tetrafluorobenzamide;
2-(4-chlorophenoxy)-N-[6-(3-fluorophenyl)-1H-indazol-3-yl]acetamide;
2,4-difluoro-N-[6-(3-fluorophenyl)-1H-indazol-3-yl]benzamide;
2,3,4,5-tetrafluoro-N-{6-[4-(trifluoromethoxy)phenyl]-1H-indazol-3-yl}benzamide;
2-(4-chlorophenoxy)-N-{6-[4-(trifluoromethoxy)phenyl]-1H-indazol-3-yl}acetamide;
2,4-difluoro-N-{6-[4-(trifluoromethoxy)phenyl]-1H-indazol-3-yl}benzamide;
N-[6-(3-methylphenyl)-1H-indazol-3-yl]-3-phenylpropanamide;
3-cyano-N-[6-(3-methylphenyl)-1H-indazol-3-yl]benzamide;
2-fluoro-N-[6-(3-methylphenyl)-1H-indazol-3-yl]benzamide;
2,6-difluoro-N[6-(3-methylphenyl)-1H-indazol-3-yl]benzamide;
2-{[6-(3-methylphenyl) 1H-indazol-3-yl]amino}-2-oxoethyl acetate;
2-{[6-(3-methylphenyl)-1H-indazol-3-yl]amino}-2-oxo-1-phenylethyl acetate;
N-[6-(4-acetylphenyl)-1H-indazol-3-yl]-3-phenylpropanamide;
N-[6-(4-acetylphenyl)-1H-indazol-3-yl]-2-fluorobenzamide;
N-[6-(4-acetylphenyl)-1H-indazol-3-yl]-2,6-difluorobenzamide;
2-{[6-(4-acetylphenyl)-1H-indazol-3-yl]amino}-2-oxoethyl acetate;
2-{[6-(4-acetylphenyl)-1H-indazol-3-yl]amino}-2-oxo-1-phenylethyl acetate;
N-[6-(3-chloro-4-fluorophenyl)-1H-indazol-3-yl]pentanamide;
2-{[6-(3-chloro-4-fluorophenyl)-1H-indazol-3-yl]amino}-2-oxoethyl acetate;
2-{[6-(3-chloro-4-fluorophenyl)-1H-indazol-3-yl]amino}-2-oxo-1-phenylethyl acetate;
N-[6-(3-chlorophenyl)-1H-indazol-3-yl]pentanamide;
N-[6-(3-chlorophenyl)-1H-indazol-3-yl]-2-fluorobenzamide;
2-{[6-(3-chlorophenyl)-1H-indazol-3-yl]amino}-2-oxoethyl acetate;
2-{[6-(3-chiorophenyl)-1H-indazol-3-yl]amino}-2-oxo-1-phenylethyl acetate;
N-[6-(3,4-dichlorophenyl)-1H-indazol-3-yl]-4-phenoxybutanamide;
2-{[6-(3,4-dichlorophenyl)-1H-indazol-3-yl]amino}-2-oxoethyl acetate;
2-{[6-(3,4-dichlorophenyl)-1H-indazol-3-yl]amino}-2-oxo-1-phenylethyl acetate;
N-[6-(3-fluorophenyl)-1H-indazol-3-yl]-3-phenylpropanamide;
N-[6-(3-fluorophenyl)-1H-indazol-3-yl]pentanamide;
2-fluoro-N-[6-(3-fluorophenyl)-1H-indazol-3-yl]benzamide;
2,6-difluoro-N-[6-(3-fluorophenyl)-1H-indazol-3-yl]benzamide;
2-{[6-(3-fluorophenyl)-1H-indazol-3-yl]amino}-2-oxoethyl acetate;
2-{[6-(3-fluorophenyl)-1H-indazol-3-yl]amino}-2-oxo-1-phenylethyl acetate;
2-oxo-2-({6-[4-(trifluoromethoxy)phenyl]-1H-indazol-3-yl}amino)ethyl acetate;
2-oxo-1-phenyl-2-({6-[4-(trifluoromethoxy)pheny]-1H-indazol-3-yl}amino)ethyl acetate;
N-[6-(2,5-dimethoxyphenyl)-1H-indazol-3-yl]-2,3,4,5-tetrafluorobenzamide;
2-chloro-N-[6-(2,5-dimethoxyphenyl)-1H-indazol-3-yl]-6-fluorobenzamide;
2-(4-chlorophenoxy)-N-[6-(2,5-dimethoxyphenyl)-1H-indazol-3-yl]acetamide;
N-[6-(2,5-dimethoxyphenyl)-1H-indazol-3-yl]-2,4-difluorobenzamide;
2-chloro-N-[6-(3,5-dimethylphenyl)-1H-indazol-3-yl]-6-fluorobenzamide;
2-(4-chlorophenoxy)-N-[6-(3,5-dimethylphenyl)-1H-indazol-3-yl]acetamide;
N-[6-(3,5-dimethylphenyl)-1H-indazol-3-yl]-2,4-difluorobenzamide;

N-[6-(3-ethoxyphenyl)-1H-indazol-3-yl]-2,3,4,5-tetrafluorobenzamide;
2-chloro-N-[6-(3-ethoxyphenyl)-1H-indazol-3-yl]-6-fluorobenzamide;
2-(4-chlorophenoxy)-N-[6-(3-ethoxyphenyl)-1H-indazol-3-yl]acetamide;
N-[6-(3-ethoxyphenyl)-1H-indazol-3-yl]-2,4-difluorobenzamide;
N-[6-(2-ethoxyphenyl)-1H-indazol-3-yl]-2,3,4,5-tetrafluorobenzamide;
2-chloro-N-[6-(2-ethoxyphenyl)-1H-indazol-3-yl]-6-fluorobenzamide;
2-(4-chlorophenoxy)-N-[6-(2-ethoxyphenyl)-1H-indazol-3-yl]acetamide;
N-[6-(2-ethoxyphenyl)-1H-indazol-3-yl]-2,4-difluorobenzamide;
N-[6-(2,6-dimethylphenyl)-1H-indazol-3-yl]-2,3,4,5-tetrafluorobenzamide;
2-chloro-N-[6-(2,6-dimethylphenyl)-1H-indazol-3-yl]-6-fluorobenzamide;
2-(4-chlorophenoxy)-N-[6-(2,6-dimethylphenyl)-1H-indazol-3-yl]acetamide;
N-[6-(2,6-dimethylphenyl)-1H-indazol-3-yl]cyclohexanecarboxamide;
N-[6-(2,6-dimethylphenyl)-1H-indazol-3-yl]-2,4-difluorobenzamide;
N-[6-(2,5-dimethoxyphenyl)-1H-indazol-3-yl]-3-phenylpropanamide;
N-[6-(2,5-dimethoxyphenyl)-1H-indazol-3-yl]-3,4-difluorobenzamide;
3-cyano-N-[6-(2,5-dimethoxyphenyl)-1H-indazol-3-yl]benzamide;
N-[6-(2,5-dimethoxyphenyl)-1H-indazol-3-yl]-2-fluorobenzamide;
N-[6-(2,5-dimethoxyphenyl)-1H-indazol-3-yl]-2,6-difluorobenzamide;
2-{[6-(2,5-dimethoxyphenyl)-1H-indazol-3-yl]amino}-2-oxoethyl acetate;
2-{[6-(2,5-dimethoxyphenyl)-1H-indazol-3-yl]amino}-2-oxo-1-phenylethyl acetate;
N-[6-(2,5-dimethoxyphenyl)-1H-indazol-3-yl]-2-(thiophen-2-yl)acetamide;
3-cyano-N-[6-(3,5-dimethylphenyl)-1H-indazol-3-yl]benzamide;
N-[6-(3,5-dimethylphenyl)-1H-indazol-3-yl]-2-fluorobenzamide;
N-[6-(3,5-dimethylphenyl)-1H-indazol-3-yl]-2,6-difluorobenzamide;
2,4-dichloro-N-[6-(3,5-dimethylphenyl)-1H-indazol-3-yl]benzamide;
2-{[6-(3,5-dimethylphenyl)-1H-indazol-3-yl]amino}-2-oxoethyl acetate;
2-{[6-(3,5-dimethylphenyl)-1H-indazol-3-yl]amino}-2-oxo-1-phenylethyl acetate;
N-[6-(3,5-dimethylphenyl)-1H-indazol-3-yl]-2-(thiophen-2-yl)acetamide;
N-[6-(3-ethoxyphenyl)-1H-indazol-3-yl]-3,4-difluorobenzamide;
3-cyano-N-[6-(3-ethoxyphenyl)-1H-indazol-3-yl]benzamide;
N-[6-(3-ethoxyphenyl)-1H-indazol-3-yl]-2,6-difluorobenzamide;
2,4-dichloro-N-[6-(3-ethoxyphenyl)-1H-indazol-3-yl]benzamide;
2-{[6-(3-ethoxyphenyl)-1H-indazol-3-yl]amino}-2-oxoethyl acetate;
2-{[6-(3-ethoxyphenyl)-1H-indazol-3-yl]amino}-2-oxo-1-phenylethyl acetate;
N-[6-(3-ethoxyphenyl)-1H-indazol-3-yl]-2-(thiophen-2-yl)acetamide;
N-[6-(2-ethoxyphenyl)-1H-indazol-3-yl]-3,4-difluorobenzamide;
3-cyano-N-[6-(2-ethoxyphenyl)-1H-indazol-3-yl]benzamide;
N-[6-(2-ethoxyphenyl)-1H-indazol-3-yl]-2-fluorobenzamide;
N-[6-(2-ethoxyphenyl)-1H-indazol-3-yl]-2,6-difluorobenzamide;
2,4-dichloro-N-[6-(2-ethoxyphenyl)-1H-indazol-3-yl]benzamide;
2-{[6-(2-ethoxyphenyl)-1H-indazol-3-yl]amino}-2-oxoethyl acetate;
2-{[6-(2-ethoxyphenyl)-1H-indazol-3-yl]amino}-2-oxo-1-phenylethyl acetate;
N-[6-(2,6-dimethylphenyl)-1H-indazol-3-yl]-3-phenylpropanamide;
N-[6-(2,6-dimethylphenyl)-1H-indazol-3-yl]pentanamide;
N-[6-(2,6-dimethylphenyl)-1H-indazol-3-yl]-3,4-difluorobenzamide;
3-cyano-N-[6-(2,6-dimethylphenyl)1H-indazol-3-yl]benzamide;
N-[6-(2,6-dimethylphenyl)-1H-indazol-3-yl]benzamide;
N-[6-(2,6-dimethylphenyl)-1H-indazol-3-yl]-2-fluorobenzamide;
N-[6-(2,6-dimethylphenyl)-1H-indazol-3-yl]-2,6-difluorobenzamide;
2,4-dichloro-N-[6-(2,6-dimethylphenyl)-1H-indazol-3-yl]benzamide;
2-{[6-(2,6-dimethylphenyl)-1H-indazol-3-yl]amino}-2-oxoethyl acetate;
2-{[6-(2,6-dimethylphenyl)-1H-indazol-3-yl]amino}-2-oxo-1-phenylethyl acetate;
N-[6-(2,6-dimethylphenyl)-1H-indazol-3-yl]-2-(thiophen-2-yl)acetamide;
N-[6-(3,4-dimethylphenyl)-1H-indazol-3-yl]-3,4-difluorobenzamide;
N-[6-(3,4-dimethylphenyl)-1H-indazol-3-yl]-2-fluorobenzamide;
N-[6-(3,4-dimethylphenyl)-1H-indazol-3-yl]-2,6-difluorobenzamide;
2,4-dichloro-N-[6-(3,4-dimethylphenyl)-1H-indazol-3-yl]benzamide;
2-{[6-(3,4-dimethylphenyl)-1H-indazol-3-yl]amino}-2-oxo-1-phenylethyl acetate;
4-phenoxy-N-{6-[4-(propan-2-yl)phenyl]-1H-indazol-3-yl}butanamide;
3,4-difluoro-N-{6-[4-(propan-2-yl)phenyl]-1H-indazol-3-yl}benzamide;
3-cyano-N-{6-[4-(propan-2-yl)phenyl]-1H-indazol-3-yl}benzamide;
N-{6-[4-(propan-2-yl)phenyl]-1H-indazol-3-yl}benzamide;
2-fluoro-N-{6-[4-(propan-2-yl)phenyl]-1H-indazol-3-yl}benzamide;
2,6-difluoro-N-{6-[4-(propan-2-yl)phenyl]-1H-indazol-3-yl}benzamide;
2-oxo-2-({6-[4-(propan-2-yl)phenyl]-1H-indazol-3-yl}amino)ethyl acetate;
2-oxo-1-phenyl-2-({6-[4-(propan-2-yl)phenyl]-1H-indazol-3-yl}amino)ethyl acetate;
N-{6-[4-(dimethylamino)phenyl]-1H-indazol-3-yl}pentanamide;

N-{6-[4-(dimethylamino)phenyl]-1H-indazol-3-yl}-3,4-difluorobenzamide;
3-cyano-N-{6-[4-(dimethylamino)phenyl]-1H-indazol-3-yl}benzamide;
N-{6-[4-(dimethylamino)phenyl]-1H-indazol-3-yl}-2-fluorobenzamide;
2-({6-[4-(dimethylamino)phenyl]-1H-indazol-3-yl}amino)-2-oxoethyl acetate;
2-({6-[4-(dimethylamino)phenyl]-1H-indazol-3-yl}amino)-2-oxo-1-phenylethyl acetate;
N-{6-[4-(dimethylamino)phenyl]-1H-indazol-3-yl}-2-(thiophen-2-yl)acetamide;
N-[6-(2-fluorophenyl)-1H-indazol-3-yl]-3-phenylpropanamide;
3,4-difluoro-N-[6-(2-fluorophenyl)-1H-indazol-3-yl]benzamide;
3-cyano-N-[6-(2-fluorophenyl)-1H-indazol-3-yl]benzamide;
2-fluoro-N-[6-(2-fluorophenyl)-1H-indazol-3-yl]benzamide;
2,4-dichloro-N-[6-(2-fluorophenyl)-1H-indazol-3-yl]benzamide;
2-{[6-(2-fluorophenyl)-1H-indazol-3-yl]amino}-2-oxoethyl acetate;
2-{[6-(2-fluorophenyl)-1H-indazol-3-yl]amino}-2-oxo-1-phenylethyl acetate;
N-[6-(2-fluorophenyl)-1H-indazol-3-yl]-2-(thiophen-2-yl)acetamide;
3,4-difluoro-N-[6-(2-methylphenyl)-1H-indazol-3-yl]benzamide;
3-cyano-N-[6-(2-methylphenyl) 1H-indazol-3-yl]benzamide;
2-fluoro-N-[6-(2-methylphenyl)-1H-indazol-3-yl]benzamide;
2-{[6-(2-methylphenyl)-1H-indazol-3-yl]amino}-2-oxoethyl acetate;
2-{[6-(2-methylphenyl)-1H-indazol-3-yl]amino}-2-oxo-1-phenylethyl acetate;
N-[6-(3-acetylphenyl)-1H-indazol-3-yl]pentanamide;
N-[6-(3-acetylphenyl)-1H-indazol-3-yl]-3,4-difluorobenzamide;
N-[6-(3-acetylphenyl)-1H-indazol-3-yl]-3-cyanobenzamide;
N-[6-(3-acetylphenyl)-1H-indazol-3-yl]benzamide;
N-[6-(3-acetylphenyl)-1H-indazol-3-yl]-2-fluorobenzamide;
N-[6-(3-acetylphenyl)-1H-indazol-3-yl]-2,6-difluorobenzamide;
N-[6-(3-acetylphenyl)-1H-indazol-3-yl]2,4-dichlorobenzamide;
2-{[6-(3-acetylphenyl)-1H-indazol-3-yl]amino}-2-oxoethyl acetate;
2-{[6-(3-acetylphenyl)-1H-indazol-3-yl]amino}-2-oxo-1-phenylethyl acetate;
N-[6-(4-cyanophenyl)-1H-indazol-3-yl]-3,4-difluorobenzamide;
N-[6-(4-cyanophenyl)-1H-indazol-3-yl]benzamide;
N-[6-(4-cyanophenyl)-1H-indazol-3-yl]-2-fluorobenzamide;
N-[6-(4-cyanophenyl)-1H-indazol-3-yl]-2,6-difluorobenzamide;
2-{[6-(4-cyanophenyl)-1H-indazol-3-yl]amino}-2-oxoethyl acetate;
2,3,4,5-tetrafluoro-N-[6-(2-fluorophenyl)-1H-indazol-3-yl]benzamide;
2-(4-chlorophenoxy)-N-[6-(2-fluorophenyl)-1H-indazol-3-yl]acetamide;
2,4-difluoro-N-[6-(2-fluorophenyl)-1H-indazol-3-yl]benzamide;
2,3,4,5-tetrafluoro-N-[6-(2-methylphenyl)-1H-indazol-3-yl]benzamide;
2-(4-chlorophenoxy)-N-[6-(2-methylphenyl) 1H-indazol-3-yl]acetamide;
2,4-difluoro-N-[6-(2-methylphenyl)-1H-indazol-3-y1] benzamide;
N-[6-(3-acetylphenyl)-1H-indazol-3-yl]-2,3,4,5-tetrafluorobenzamide;
N-[6-(3-acetylphenyl)-1H-indazol-3-yl]-2-(4-chlorophenoxy)acetamide;
N-[6-(3-acetylphenyl)-1H-indazol-3-yl]-2,4-difluorobenzamide;
N-[6-(4-cyanophenyl)-1H-indazol-3-yl]-2,3,4,5-tetrafluorobenzamide;
N-[6-(4-cyanophenyl)-1H-indazol-3-yl]-2,4-difluorobenzamide;
N-[6-(2,4-difluorophenyl)-1H-indazol-3-yl]-2,3,4,5-tetrafluorobenzamide;
N-[6-(2,4-difluorophenyl)-1H-indazol-3-yl]-Nalpha-[(4-methylphenyl))sulfonyl]-L-phenylalaninamide;
N-[6-(2,4-dimethoxyphenyl)-1H-indazol-3-ylZ]-2,3,4,5-tetrafluorobenzamide;
2-chloro-N-[6-(2,4-dimethoxyphenyl)-1H-indazol-3-yl]-6-fluorobenzamide;
2-(4-chlorophenoxy)-N-[6-(2,4-dimethoxyphenyl)-1H-indazol-3-yl]acetamide;
N-[6-(2,4-dimethoxyphenyl)-1H-indazol-3-yl]cyclohexanecarboxamide;
N-[6-(2,4-dimethoxyphenyl)-1H-indazol-3-yl]-2,4-difluorobenzamide;
N-[6-(3-cyanophenyl)-1H-indazol-3-yl]-2,3,4,5-tetrafluorobenzamide;
N-[6-(3-cyanophenyl)-1H-indazol-3-yl]-2,4-difluorobenzamide;
N-{6-[4-(ethylsulfanyl)phenyl]-1H-indazol-3-yl}-2,3,4,5-tetrafluorobenzamide;
N-{6-[4-(ethylsulfanyl)phenyl]-1H-indazol-3-yl}-2,4-difluorobenzamide;
2,3,4,5-tetrafluoro-N-{6-[2-methoxy-5-(propan-2-yl)phenyl]-1H-indazol-3-yl}benzamide;
2-(4-chlorophenoxy)-N-{6-[2-methoxy-5-(propan-2-yl)phenyl]-1H-indazol-3-yl}acetamide;
N-{6-[2-methoxy-5-(propan-2-yl)phenyl]-H-indazol-3-yl}cyclohexanecarboxamide;
2,4-difluoro-N-{6-[2-methoxy-5-(propan-2-yl)phenyl]-1H-indazol-3-yl}benzamide;
2,3,4,5-tetrafluoro-N-{6-[2-(methylsulfanyl)phenyl]-1H-indazol-3-yl}benzamide;
2-(4-chlorophenoxy)-N-{6-[2-(methylsulfanyl)phenyl]-1H-indazol-3-yl}acetamide;
N-{6-[2-(methylsulfanyl)phenyl]-1H-indazol-3-yl}cyclohexanecarboxamide;
2,4-difluoro-N-{6-[2-(methylsulfanyl)phenyl]-1H-indazol-3-yl}benzamide;
2,3,4,5-tetrafluoro-N-{6-[3-(trifluoromethoxy)phenyl]-1H-indazol-3-yl}benzamide;
2-(4-chlorophenoxy)-N-{6-[3-(trifluoromethoxy)phenyl]-1H-indazol-3-yl}acetamide;
2,4-difluoro-N-{6-[3-(trifluoromethoxy)phenyl]-1H-indazol-3-yl}benzamide;
N-[6-(2,5-dimethylphenyl)-1H-indazol-3-yl]-2,3,4,5-tetrafluorobenzamide;
2-chloro-N-[6-(2,5-dimethylphenyl)-1H-indazol-3-yl]-6-fluorobenzamide;

2-(4-chlorophenoxy)-N-[6-(2,5-dimethylphenyl)-1I-1-indazol-3-yl]acetamide;
N-[6-(2,5-dimethylphenyl)-1H-indazol-3-yl]cyclohexanecarboxamide;
N-[6-(2,5-dimethylphenyl)-1H-indazol-3-yl]-2,4-difluorobenzamide;
N-[6-(2,5-difluorophenyl)-1H-indazol-3-yl]-2,3,4,5-tetrafluorobenzamide;
2-chloro-N-[6-(2,5-difluorophenyl)-1H-indazol-3-yl]-6-fluorobenzamide;
N-[6-(2,5-difluorophenyl)-1H-indazol-3-yl]-2,4-difluorobenzamide;
N-[6-(3,4-difluorophenyl)-1H-indazol-3-yl]-2,3,4,5-tetrafluorobenzamide;
2-(4-chlorophenoxy)-N-[6-(3,4-difluorophenyl)-1H-indazol-3-yl]acetamide;
N[6-(3,4-difluorophenyl)-1H-indazol-3-yl]-2,4-difluorobenzamide;
2,3,4,5-tetrafluoro-N-[6-(5-fluoro-2-methoxyphenyl)-1H-indazol-3-yl]benzamide;
2-(4-chlorophenoxy)-N-[6-(5-fluoro-2-methoxyphenyl)-1H-indazol-3-yl]acetamide;
2,4-difluoro-N-[6-(5-fluoro-2-methoxyphenyl)-1H-indazol-3-yl]benzamide;
2,3,4,5-tetrafluoro-N-[6-(thiophen-2-yl-1H-indazol-3-yl]benzamide;
2,4-difluoro-N-[6-(thiophen-2-yl)-1H-indazol-3-yl]benzamide;
2,3,4,5-tetrafluoro-N-[6-(2-methoxyphenyl)-1H-indazol-3-yl]benzamide;
2-(4-chlorophenoxy)-N-[6-(2-methoxyphenyl)-1H-indazol-3-yl]acetamide;
N-[6-(2-methoxyphenyl)-1H-indazol-3-yl]cyclohexanecarboxamide;
2,4-difluoro-N-[6-(2-methoxyphenyl)-1H-indazol-3-yl]benzamide;
2,3,4,5-tetrafluoro-N-[6-(4-methylphenyl)-1H-indazol-3-yl]benzamide;
2-(4-chlorophenoxy)-N-[6-(4-methylphenyl)-1H-indazol-3-yl]acetamide;
N-[6-(4-methylphenyl)-1H-indazol-3-yl]cyclohexanecarboxamide;
2,4-difluoro-N-[6-(4-methylphenyl-1H-indazol-3-yl]benzamide;
2,3,4,5-tetrafluoro-N-(6-phenyl-1H-indazol-3-yl)benzamide;
2-(4-chlorophenoxy)-N-(6-phenyl-1H-indazol-3-yl)acetamide;
N-(6-phenyl-1H-indazol-3-yl)cyclohexanecarboxamide;
2,4-difluoro-N-(6-phenyl-1H-indazol-3-yl)benzamide;
2,4-difluoro-N-[6-(thiophen-3-yl)-1H-indazol-3-yl]benzamide;
2-{[6-(3,4-difluorophenyl)-1H-indazol-3-yl]amino}-2-oxo-1-phenylethyl acetate;
N-{6-[4-(ethylsulfanyl)phenyl]-1H-indazol-3-yl}-2,6-difluorobenzamide;
2-({6-[4-ethylsulfanyl]phenyl-1H-indazol-3-yl}amino)-2-oxoethyl acetate;
2-({6-[4-(ethylsulfanyl)phenyl]-1H-indazol-3-yl}amino)-2-oxo-1-phenylethyl acetate;
N-{6-[2-methoxy-5-(propan-2-yl)phenyl]-1H-indazol-3-yl}-3-phenylpropanamide;
N-{6-[2-methoxy-5-(propan-2-yl)phenyl]-1H-indazol-3-yl}pentanamide;
b 3,4-difluoro-N-{6-[2-methoxy-5-(propan-2-yl)phenyl]-1H-indazol-3-yl}benzamide;
3-cyano-N-{6-[2-methoxy-5-(propan-2-yl)phenyl]-1H-indazol-3-yl}benzamide;
N-{6-[2-methoxy-5-(propan-2-yl)phenyl]-1H-indazol-3-yl}benzamide;
2-fluoro-N-{6-[2-methoxy-5-(propan-2-yl)phenyl]-1H-indazol-3-yl}benzamide;
2,6-difluoro-N-{6-[2-methoxy-5-(propan-2-yl)phenyl]-1H-indazol-3-yl}benzamide;
2,4-dichloro-N-{6-[2-methoxy-5-(propan-2-yl)phenyl]-1H-indazol-3-yl}benzamide;
2-({6-[2-methoxy-5-(propan-2-yl)phenyl]-1H-indazol-3-yl}amino)-2-oxoethyl acetate;
2-({6-[2-methoxy-5-(propan-2-yl)phenyl]-1H-indazol-3-yl}amino)-2-oxo-1-phenylethyl acetate;
N-{6-[2-methoxy-5-(propan-2-yl)phenyl]-1H-indazol-3-yl}-2-(thiophen-2-yl)acetamide;
N-{6-[2-(methylsulfanyl)phenyl]-1H-indazol-3-yl}-3-phenylpropanamide;
3,4-difluoro-N-{6-[2-(methylsulfanyl)phenyl]1H-indazol-3-yl}benzamide;
3-cyano-N-{6-[2-(methylsulfanyl)phenyl]-1H-indazol-3-yl}benzamide;
2-fluoro-N-{6-[2-(methylsulfanyl)phenyl]-1H-indazol-3-yl}benzamide;
2,6-difluoro-N-{6-[2-(methylsulfanyl)phenyl]-1H-indazol-3-yl}benzamide;
2,4-dichloro-N-{6-[2-(methylsulfanyl)phenyl]-1H-indazol-3-yl}benzamide;
2-({6-[2-(methylsulfanyl)phenyl]1H-indazol-3yl}amino)-2-oxoethyl acetate;
2-({6-[2-(methylsulfanyl)phenyl]-1H-indazol-3-yl}amino)-2-oxo-1-phenylethyl acetate;
N-{6-[2-(methylsulfanyl)phenyl]-1H-indazol-3-yl}-2-(thiophen-2-yl)acetamide;
3,4-difluoro-N-{6-[3-(trifluoromethoxy)phenyl]-1H-indazol-3-yl}benzamide;
3-cyano-N-{6-[3-(trifluoromethoxy)phenyl]-1H-indazol-3-yl}benzamide;
2-fluoro-N-{6-[3-(trifluoromethoxy)phenyl]-1H-indazol-3-yl}benzamide;
2,6-difluoro-N-{6-[3-(trifluoromethoxy)phenyl]-1H-indazol-3-yl}benzamide;
2-oxo-2-({6-[3-(trifluoromethoxy)phenyl]-1H-indazol-3-yl}amino)ethyl acetate;
2-oxo-1-phenyl-2-({6-[3(trifluoromethoxy)phenyl]-1H-indazol-3-yl}amino)ethyl acetate;
N-[6-(2,5-dimethylphenyl)-1H-indazol-3-yl]-3-phenylpropanamide;
N-[6-(2,5-dimethylphenyl)-1H-indazol-3-yl]pentanamide;
N-[6-(2,5-dimethylphenyl)-1H-indazol-3-yl]-3,4-difluorobenzamide;
3-cyano-N-[6-(2,5-dimethylphenyl)-1H-indazol-3-yl]benzamide;
N-[6-(2,5-dimethylphenyl)-1H-indazol-3-yl]benzamide;
N-[6-(2,5-dimethylphenyl)-1H-indazol-3-yl]-2-fluorobenzamide;
N-[6-(2,5-dimethylphenyl)-1H-indazol-3-yl]-2,6-difluorobenzamide;
2-{[6-(2,5-dimethylphenyl)-1H-indazol-3-yl]amino}-2-oxoethyl acetate;
2-{[6-(2,5-dimethylphenyl)-1H-indazol-3-yl]amino}-2-oxo-1-phenylethyl acetate;
N-[6-(2,5-dimethylphenyl)-1H-indazol-3-yl]-2-(thiophen-2-yl)acetamide;
N-[6-(2,5-difluorophenyl)-1H-indazol-3-yl]-3-phenylpropanamide;

N-[6-(2,5-difluorophenyl)-1H-indazol-3-yl]pentanamide;
N-[6-(2,5-difluorophenyl)-1H-indazol-3-yl]benzamide;
N-[6-(2,5-difluorophenyl)-1H-indazol-3-yl]-2-fluorobenzamide;
N-[6-(2,5-difluorophenyl)-1H-indazol-3-yl]-2,6-difluorobenzamide;
2,4-dichloro-N-[6-(2,5-difluorophenyl)-1H-indazol-3-yl]benzamide;
2-{[6-(2,5-difluorophenyl)-1H-indazol-3-yl]amino}-2-oxoethyl acetate;
2-{[6-(2,5-difluorophenyl)-1H-indazol-3-yl]amino}-2-oxo-1-phenylethyl acetate;
N-[6-(4-methoxyphenyl)-1H-indazol-3-yl]piperidine-1-carboxamide;
N-butyl-N'-[6-(4-methoxyphenyl)-1H-indazol-3-yl]urea;
1-butyl-3-[6-(4-methoxyphenyl)-1H-indazol-3-yl]urea;
1-[6-(4-methoxyphenyl)-1H-indazol-3-yl]-3-[2-(morpholin-4-yl)ethyl]urea;
1-[3-(1H-imidazol-1-yl)propyl]-3-[6-(4-methoxyphenyl)-1H-indazol-3-yl]urea;
1-[6-(4-methoxyphenyl)-1H-indazol-3-yl]-3-(tetrahydrofuran-2-ylmethyl)urea;
1-[6-(4-methoxyphenyl)-1H-indazol-3-yl]-3-(2-phenylethyl)urea;
1-[6-(4-methoxyphenyl)-1H-indazol-3-yl]-3-(3-phenylpropyl)urea;
1-[6-(4-methoxyphenyl)-1H-indazoi-3-yl]-3-propylurea;
1-[6-(4-methoxyphenyl)-1H-indazol-3-yl]-3-(2-methylpropyl)urea;
1-(cyclopropylmethyl)-3-[6-(4-methoxyphenyl)-1H-indazol-3-yl]urea;
1-[6-(4-methoxyphenyl)-1H-indazol-3-yl]-3-[2-(1-methylpyrrolidin-2-yl)ethyl]urea;
N-[6-(3-methoxyphenyl)-1H-indazol-3-yl]piperidine-1-carboxamide;
1-[6-(3-methoxyphenyl)-1H-indazol-3-yl]-3-[2-(morpholin-4-yl)ethyl]urea;
1-[3-(1H-imidazol-1-yl)propyl]-3-[6-(3-methoxyphenyl)-1H-indazol-3-yl]urea;
N-[6-(3-methoxyphenyl)-1H-indazol-3-yl]piperazine-1-carboxamide;
1-[6-(3-methoxyphenyl)-1H-indazol-3-yl]-3-(tetrahydrofuran-2-ylmethyl)urea;
1-[6-(3-methoxyphenyl)-1H-indazol-3-yl]-3-(2-phenylethyl)urea;
1-[6-(3-methoxyphenyl)-1H-indazol-3-yl]-3-(3-phenylpropyl)urea;
1-[6-(3-methoxyphenyl)-1H-indazol-3-yl]-3-(2-methylpropyl)urea;
1-(cyclopropylmethyl)-3-[6-(3-methoxyphenyl)-1H-indazol-3-yl]urea;
1-[6-(3-methoxyphenyl)-1H-indazol-3-yl]-3-[2-(1-methylpyrrolidin-2-yl)ethyl]urea;
N-[6-(thiophen-3-yl)-1H-indazol-3-yl]piperidine-1-carboxamide;
1-[2-(morpholin-4-yl)ethyl]-3[6-(thiophen-3-yl)-1H-indazol-3-yl]urea;
1-[3-(1H-imidazol-1-yl)propyl]-3-[6-(thiophen-3-yl)-1H-indazol-3-yl]urea;
N-[6-(thiophen-3-yl)-1H-indazol-3-yl]piperazine-1-carboxamide;
1-(tetrahydrofuran-2-ylmethyl)-3-[6-(thiophen-3-yl)-1H-indazol-3-yl]urea;
1-(2-phenylethyl)-3-[6-(thiophen-3-yl)-1H-indazol-3-yl]urea;
1-(3-phenylpropyl)-3-[6-(thiophen-3-yl)-1H-indazol-3-yl]urea;
1-propyl-3-[6-(thiophen-3-yl)-1H-indazol-3-yl]urea;
1-(2-methylpropyl)-3-[6-(thiophen-3-yl)-1H-indazol-3-yl]urea;
1-(cyclopropylmethyl)-3-[6-(thiophen-3-yl)-1H-indazol-3-yl]urea;
1-[2-(methylpyrrolidin-2-yl)ethyl ]-3-[6-(thiophen-3-yl)-1H-indazol-3-yl]urea;
N-[6-(4-methylphenyl)-1H-indazol-3-yl]piperidine-1-carboxamide;
1-butyl-3-[6-(4-methylphenyl)-1H-indazol-3-yl]urea;
1-[6-(4-methylphenyl)-1H-indazol-3-yl]-3-[2-(morpholin-4-yl)ethyl]urea;
1-[3-(1H-imidazol-1-yl)propyl]-3-[6-(4methylphenyl)-1H-indazol-3-yl]urea;
N-[6-(4-methylphenyl)-1H-indazol-3-yl]piperazine-1-carboxamide;
1-[6-(4-methylphenyl)-1H-indazol-3-yl]-3-(3-phenylpropyl)urea;
1-[6-(4-methylphenyl)-1H-indazol-3-yl]-3-propylurea;
1-[6-(4-methylphenyl)-1H-indazol-3-yl]-3-(2-methylpropyl)urea;
1-(cyclopropylmethyl)-3-[6-(4-methylphenyl)-1H-indazol-3-yl]urea;
1-[6-(4-methylphenyl)-1H-indazol-3-yl]-3-[2-(1-methylpyrrolidin-2-yl)ethyl]urea;
1-butyl-3-[6-(2-methoxyphenyl)-1H-indazol-3-yl]urea;
1-[6-(2-methoxyphenyl)-1H-indazol-3-yl]-3-[2-(morpholin-4-yl)ethyl]urea;
1-[3-(1H-imidazol-1-yl)propyl]-3-[6-(2-methoxyphenyl)-1H-indazol-3 -yl]urea;
N-[6-(2-methoxyphenyl)-1H-indazol-3-yl]piperazine-1-carboxamide;
1-[6-(2-rnethoxyphenyl)-1H-indazol-3-yl]-3-(tetrahydroftiran-2-ylmethyl)urea;
1-[6-(2-methoxyphenyl)-1H-indazol-3-yl]-3-(2-phenylethyl)urea;
1-[6-(2-methoxyphenyl)-1H-indazol-3-yl]-3-(3-phenylpropyl)urea;
1-[6-(2-methoxyphenyl)-1H-indazol-3-yl]-3-propylurea;
1-[6-(2-methoxyphenyl)-1H-indazol-3-yl]-3-(2-methylpropyl)urea;
1-(cyclopropylmethyl)-3-[6-(2-methoxyphenyl)-1H-indazol-3-yl]urea;
1-[6-(2-methoxyphenyl)-1H-indazol-3-yl]-3-[2-(1-methylpyrrolidin-2-yl)ethyl]urea;
N-[6-(3-methylphenyl)-1H-indazol-3-yl]piperidine-1-carboxamide;
1-butyl-3-[6-(3-methylphenyl)-1H-indazol-3-yl]urea;
1-[6-(3-methylphenyl)-1H-indazol-3-yl]-3-[2-(morpholin-4-yl)ethyl]urea;
1-[3(1H-imidazol-1-yl)propyl]-3-[6-(3-methylphenyl)-1H-indazol-3-yl]urea;
N-[6-(3-methylphenyl)-1H-indazol-3-yl]piperazine-1-carboxamide;
1-[6-(3-methylphenyl)-1H-indazol-3-yl]-3-(2-phenylethyl)urea;
1-[6-(3-methylphenyl)-1H-indazol-3-yl]-3-propylurea;
1-[6-(3-methylphenyl)-1H-indazol-3-yl]-3-(2-methylpropyl)urea;
1-[6-(3-methylphenyl)-1H-indazol-3-yl]-3-[2-(1-methylpyrrolidin-2-yl)ethyl]urea;
N-{6-[3-(acetylamino)phenyl]-1H-indazol-3-yl}piperidine-1-carboxamide;
N-[3-(3-{[(butylamino)carbonyl]amino}-1H-indazol-6-yl)phenyl]acetamide;
N-(3-{3-[(butylcarbamoyl)amino]-1H-indazol-6-yl}phenyl)acetamide;

N-{3-[3-({[2-(morpholin-4-yl)ethyl]carbamoyl}amino)-1H-indazol-6-yl]phenyl}acetamide;
N-{3-[3-({[3-(1H-imidazol-1-yl)propyl]carbamoyl}amino)-1H-indazol-6-yl]phenyl}acetamide; N-[3-(3-{[(tetrahydrofuran-2-ylmethyl)carbamoyl]amino}-1H-indazol-6-yl)phenyl]acetamide;
N-[3(3-{[(2-phenylethyl)carbamoyl]amino }-1H-indazol-6-yl)phenyl]acetamide;
N-[3-(3-{[(3-phenylpropyl)carbamoyl]amino}-1H-indazol-6-yl)phenyl]acetamide;
N-(3-{3-[(propylcarbamoyl)amino]-1H-indazol-6-yl}phenyl)acetamide;
N-[3-(3-{[(cyclopropylmethyl)carbamoyl]amino}-1H-indazol-6-yl)phenyl]aeetamide;
N-{3-[3-({[2-(1-methylpyrrolidin-2-yl)ethyl]carbamoyl}amino)-1H-indazol-6-yl]phenyl}acetamide;
N-[6-(4-methoxyphenyl)-1H-indazol-3-yl]-4-methylpiperidine-1-carboxamide;
N-[6-(4-methoxyphenyl)-1H-indazol-3-yl]-4-methylpiperazine-1-carboxamide;
1-[6-(4-methoxyphenyl)-1H-indazol-3-yl]-3-[3-(2-oxopyrrolidin-1-yl)propyl]urea;
1-(3-aminopropyl)-3-[6-(4-methoxyphenyl)-1H-indazol-3-yl]urea;
1-(2-aminoethyl)-3-[6-(4-methoxyphenyl)-1H-indazol-3-yl]urea;
4-hydroxy-N-[6-(4-methoxyphenyl)-1H-indazol-3-yl]piperidine-1-carboxamide;
1-(3-hydroxypropyl)-3-[6-(4-methoxyphenyl)-1H-indazol-3-yl]urea;
1-[6-(4-methoxyphenyl)-1H-indazol-3-yl]-3-[2-(pyridin-2-yl)ethyl]urea;
1-[6-(4-methoxyphenyl)-1H-indazol-3-yl]-3-[2-(piperidin-1-yl)ethyl]urea;
N-[6-(4-methoxyphenyl)-1H-indazol-3-yl]pyrrolidine-1-carboxamide;
N-[2-({[6-(4-methoxyphenyl)-1H-indazol-3-yl]carbamoyl}amino)ethyl]acetamide;
4-acetyl-N-[6-(4-methoxyphenyl)-1H-indazol-3-yl]piperazine-1-carboxamide;
N-[6-(3-methoxyphenyl)-1H-indazol-3-yl]-4-methylpiperidine-1-carboxamide;
N-[6-(3-methoxyphenyl)-1H-indazol-3-yl]-4-methylpiperazine-1-carboxamide;
1-[6-(3-methoxyphenyl)-1H-indazol-3-yl]-3-[3-(2-oxopyrrolidin-1-yl)propyl]urea;
4-hydroxy-N-[6-(3-methoxyphenyl)-1H-indazol-3-yl]piperidine-1-carboxamide;
1-(3-hydroxypropyl)-3-[6-(3-methoxyphenyl)-1H-indazol-3-yl]urea;
1-[6-(3-methoxyphenyl)-1H-indazol-3-yl]-3-[2-(pyridin-2-yl)ethyl]urea;
1-[6-(3-methoxyphenyl)-1H-indazol-3-yl]-3-[2-(piperidin-1-yl)ethyl]urea;
N-[6-(3-methoxyphenyl)-1H-indazol-3-yl]pyrrolidine-1-carboxamide;
N-[2-({[6-(3-methoxyphenyl)-1H-indazol-3-yl]carbamoyl}amino)ethyl]acetamide; 4-acetyl-N-[6-(3-methoxyphenyl)-1H-indazol-3-yl]piperazine-1-carboxamide;
4-methyl-N-[6-(thiophen-3-yl)-1H-indazol-3-yl]piperidine-1-carboxamide;
4-methyl-N-[6-(thiophen-3-yl)-1H-indazol-3-yl]piperazine-1-carboxamide;
1-[3-(2-oxopyrrolidin-1-yl)propyl]-3-[6-(thiophen-3-yl)-1H-indazol-3-yl]urea;
1-(3-aminopropyl)-3-[6-(thiophen-3-yl)-1H-indazol-3-yl]urea;
1-(2-aminoethyl)-3-[6-(thiophen-3-yl)-1H-indazol-3-yl]urea;
4-hydroxy-N-[6-(thiophen-3-yl)-1H-indazol-3-yl]piperidine-1-carboxamide;
1-(3-hydroxypropyl)-3-[6-(thiophen-3-yl)-1H-indazol-3-yl]urea;
1[2-(pyridin-2-yl)ethyl]-3-[6-(thiophen-3-yl)-1H-indazol-3-yl]urea;
1-[2-(piperidin-1-yl)ethyl]-3-[6-(thiophen-3-yl)-1H-indazol-3-yl]urea;
N-[6-(thiophen-3-yl)-1H-indazol-3-yl]pyrrolidine-1-carboxamide;
N-[2-({[(6-(thiophen-3-yl)-1H-indazol-3-yl]carbamoyl}amino)ethyl]acetamide;
4-acetyl-N-[6-(thiophen-3-yl)-1H-indazol-3-yl]piperazine-1-carboxamide;
4-methyl-N-[6(4-methylphenyl)-1H-indazol-3-yl]piperidine-1-carboxamide;
4-methyl-N-[6-(4-methylphenyl)1H-indazol-3-yl]piperazine-1-carboxamide;
1-[6-(4-methylphenyl)-1H-indazol-3-yl]-3-[3-(2-oxopyrrolidin-1-yl)propyl]urea;
1-(3-aminopropyl)-3-[6-(4-methylphenyl)-1H-indazol-3-yl]urea;
1-(2-aminoethyl)-3-[6-(4-methylphenyl)-1H-indazol-3-yl]urea;
4-hydroxy-N-[6-(4-methylphenyl)-1H-indazol-3-yl]piperidine-1-carboxamide;
1-(3-hydroxypropyl)-3-[6-(4-methylphenyl)-1H-indazol-3-yl]urea;
1-[6-(4-methylphenyl)-1H-indazol-3-yl]-3-[2-(pyridin-2-yl)ethyl]urea;
1-[6-(4-methylphenyl)-1H-indazol-3-yl]-3-[2-(piperidin-1-yl)ethyl]urea;
N-[6-(4-methylphenyl)-1H-indazol-3-yl]pyrrolidine-1-carboxamide;
N-[2-({[6-(4methylphenyl)-1H-indazol-3-yl]carhamoyl}amino)ethyl]acetamide;
4-acetyl-N-[6-(4-methylphenyl)-1H-indarzol-3-yl]piperazine-1-carboxamide;
N-[6-(2-methoxyphenyl)-1H-indazol-3-yl]-4-methylpiperidine-1-carboxamide;
N-[6-(2-methoxyphenyl)-1H-indazol-3-yl]-4-methylpiperazine-1-carboxarnide;
1-[6-(2-methoxyphenyl) 1H-indazol-3-yl]-3-[3-(2-oxopyrrolidin-1-yl)propyl]urea;
1-(3-aminopropyl)-3-[6-(2-methoxyphenyl)-1H-indazol-3-yl]urea;
1-(2-aminoethyl)-3-[6-(2-methoxyphenyl)-1H-indazol-3-yl]urea;
4-hydroxy-N-[6-(2-methoxyphenyl)-1H-indazol-3-yl]piperidine-1-carboxamide;
1-(3-hydroxypropyl)-3-[6-(2-methoxyphenyl)-1H-indazol-3-yl]urea;
1-[6-(2-methoxyphenyl)-1H-indazol-3-yl]-3-[2-(pyridin-2-yl)ethyl]urea;
1-[6-(2-methoxyphenyl)-1H-indazol-3-yl]-3-[2-(piperidin-1-yl)ethyl]urea;
N-[6-(2-methoxyphenyl)-1H-indazol-3-yl]pyrrolidine-1-carboxamide;
N-[2-({[6-(2-methoxyphenyl)1H-indazol-3-yl]carbamoyl}amino)ethyl]acetamide;

4-acetyl-N-[6-(2-methoxyphenyl)-1H-indazol-3-yl]piperazine-1-carboxamide;
1-(2-aminoethyl)-3-[6-(thiophen-2-yl)-1H-indazol-3-yl]urea;
4-methyl-N-[6-(3-methylphenyl)-1H-indazol-3-yl]piperidine-1-carboxamide;
4-methyl-N-[6-(3-methylphenyl)-1H-indazol-3-yl]piperazine-1-carboxamide;
1-[6-(3-methylphenyl)-1H-indazol-3-yl]-3-[3-(2-oxopyrolidin-1-yl)propyl]urea;
1-(3-aminopropyl)-3-[6-(3-methylphenyl)-1H-indazol-3-yl]urea;
1-(2-aminoethyl)-3-[6-(3-methylphenyl)-1H-indazol-3-yl]urea;
4-hydroxy-N-[6-(3-methylphenyl)-1H-indazol-3-yl]piperidine-1 -carboxamide;
1-(3-hydroxypropyl)-3-[6-(3-methylphenyl)-1H-indazol-3-yl]urea;
1-[6-(3-methylphenyl)-1H-indazol-3-yl]-3-[2-(pyridin-2-yl)ethyl]urea;
1-[6-(3-methylphenyl)-1H-indazol-3-yl]-3-[2-(piperidin-1-yl)ethyl]urea;
N-[6-(3-methylphenyl)-1H-indazol-3-yl]pyrrolidine-1-carboxamide;
N-[2-({[6-(3-methylphenyl)-1H-indazol-3-yl]carbamoyl}amino)ethyl]acetamide;
4-acetyl-N-[6-(3-methylphenyl)-1H-indazol-3-yl]piperazine-1-carboxamide;
N-{6-[3-(acetylamino)phenyl]-1H-indazol-3-yl}-4-methylpiperidine-1-carboxamide;
N-{3-[3-({[3-(2-oxopyrrolidin-1-yl)propyl]carbamoyl}(amino)-1H-indazol-6-yl]phenyl}acetamide;
N-[3-(3-{[(3-aminopropyl)carbamoyl]amino}-1H-indazol-6-yl)phenyl]acetamide;
N-[3-(3-{[(2-aminoethyl)carbamoyl]amino}-1H-indazol-6-yl)phenyl]acetamide;
N-{6-[3-(acetylamino)phenyl]-1H-indazol-3-yl}-4-hydroxypiperidine-1-carboxamide;
N-[3-(3-{[(3-hydroxypropyl)carbamoyl]amino}-1H-indazol-6-yl)phenyl]acetamide;
N-{3-[3-({[2-(pyridin-2-yl)ethyl]carbamoyl}amino)-1H-indazol-6-yl]phenyl}acetamide;
N-{3-[3-({[2-(piperidin-1-yl)ethyl]carbamoyl}amino)-1H-indazol-6-yl]phenyl}acetamide;
N-{3-[3-({[2-(acetylamino)ethyl]carbamoyl}amino)-1H-indazol-6-yl]phenyl}acetamide;
1-[6-(4-methoxyphenyl)-1H-indazol-3-yl]-3-(3-methoxypropyl)urea;
N-[6-(4-methoxyphenyl)-1H-indazol-3-yl]-3-methylpiperidine-1-carboxamide;
N-[6-(4-methoxyphenyl)-1H-indazol-3-yl]-4-(pyridin-2-yl)piperazine-1-carboxamide;
4-benzyl-N-[6-(4-methoxyphenyl)1H-indazol-3-yl]piperidine-1-carboxamide;
1-[(1-ethylpyrrolidin-2-yl)methyl]-3-[6-(4-methoxyphenyl )-1H-indazol-3-yl]urea;
4-(furan-2-ylcarbonyl)-N-[6-(4-methoxyphenyl)-1H-indazol-3-yl]piperazine-1-carboxamide;
1[6-(4-methoxyphenyl)-1H-indazol-3-yl]-3-[2-(thiophen-2-yl)ethyl]urea;
1[6-(4-methoxyphenyl)-1H-indazol-3-yl]-3-[2-(2-oxoimidazolidin-1-yl)ethyl]urea;
N-[6-(4-methoxyphenyl)-1H-indazol-3-yl]thiomorpholine-4-carboxamide;
1-[6-(3-methoxyphenyl)-1H-indazol-3-yl]-3-(3-methoxypropyl)urea;
N-[6-(3-methoxyphenyl)-1H-indazol-3-yl]-3-methylpiperidine-1-carboxamide;
1-[6-(3-methoxyphenyl)-1H-indazol-3-yl]-3-(2-methylbutyl)urea;
N[6-(3-methoxyphenyl)-1H-indazol-3-yl]-4-(pyridin-2-yl)piperazine-1-carboxamide;
4-benzyl-N-[6-(3-methoxyphenyl)-1H-indazol-3-yl]piperidine-1-carboxamide;
N~3~,N~3~-diethyl-N~1~-[6-(3methoxyphenyl)-1H-indazol-3-yl]piperidine-1,3-dicarboxamide;
N-[6-(3-methoxyphenyl)1H-indazol-3-yl]-3 ,5-dimcthylpiperidine-1-carboxamide;
1[(1-ethylpyrrolidin-2-yl)methyl]-3-[6-(3-methoxyphenyl)-1H-indazol-3-yl]urea;
4-(furan-2-ylcarbonyl)-N-[6-(3-methoxyphenyl)-1H-indazol-3-yl]piperazine-1-carboxamide;
1-[6-(3-melhoxyphenyl)-1H-indazol-3-yl]-3-[2-(thiophen-2-yl)ethyl]urea;
1-[6-(3-methoxyphenyl)-1H-indazol-3-yl]-3-[2-(2-oxoimidazolidin-1-yl)ethyl]urea;
N-[6-(3-methoxyphenyl)-1H-indazol-3-yl]thiomorpholine-4-carboxamide;
1-(3-methoxypropyl)-3-[6-(thiophen-3-yl)-1H-indazol-3-yl]urea;
3-methyl-N-[6-(thiophen-3-yl)-1H-indazol-3-yl]piperidine-1-carboxamide;
4-benzyl-N-[6-(thiophen-3-yl)-1H-indazol-3-yl]piperidine-1-carboxamide; and
1-butyl-3-[6-(3-methoxyphenyl)-1H-indazol-3-yl]urea.

\* \* \* \* \*

UNITED STATES PATENT AND TRADEMARK OFFICE
CERTIFICATE OF CORRECTION

PATENT NO. : 7,632,854 B2  Page 1 of 1
APPLICATION NO. : 10/990866
DATED : December 15, 2009
INVENTOR(S) : Martina et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1234 days.

Signed and Sealed this

Twenty-first Day of December, 2010

David J. Kappos
*Director of the United States Patent and Trademark Office*